United States Patent
Hayashi et al.

(10) Patent No.: US 10,950,797 B2
(45) Date of Patent: Mar. 16, 2021

(54) ORGANIC ELECTROLUMINESCENT DEVICE

(71) Applicant: HODOGAYA CHEMICAL CO., LTD., Tokyo (JP)

(72) Inventors: Shuichi Hayashi, Tokyo (JP); Naoaki Kabasawa, Tokyo (JP); Keigo Naito, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 293 days.

(21) Appl. No.: 15/762,360

(22) PCT Filed: Sep. 15, 2016

(86) PCT No.: PCT/JP2016/077297
§ 371 (c)(1),
(2) Date: Mar. 22, 2018

(87) PCT Pub. No.: WO2017/051765
PCT Pub. Date: Mar. 30, 2017

(65) Prior Publication Data
US 2018/0294416 A1 Oct. 11, 2018

(30) Foreign Application Priority Data

Sep. 25, 2015 (JP) .............................. JP2015-187600

(51) Int. Cl.
*H01L 51/00* (2006.01)
*H01L 51/50* (2006.01)
(Continued)

(52) U.S. Cl.
CPC ........ *H01L 51/0059* (2013.01); *C07C 211/54* (2013.01); *C07C 211/61* (2013.01);
(Continued)

(58) Field of Classification Search
None
See application file for complete search history.

(56) References Cited

U.S. PATENT DOCUMENTS 5,639,914 A 6/1997 Tomiyama et al.
5,707,747 A 1/1998 Tomiyama et al.
(Continued)

FOREIGN PATENT DOCUMENTS

EP 3 051 604 8/2016
JP 7-126615 5/1995
(Continued)

OTHER PUBLICATIONS

European Search Report issued in corresponding patent application No. 16848553.0 dated Apr. 24, 2019.
(Continued)

*Primary Examiner* — Robert S Loewe
(74) *Attorney, Agent, or Firm* — Greenblum & Bernstein, P.L.C.

(57) ABSTRACT

The present invention provides an organic EL device having at least an anode, a first hole transport layer, a second hole transport layer, a luminous layer, an electron transport layer, and a cathode in this order, wherein the second hole transport layer contains an arylamine compound represented by the following general formula (1), and the electron transport layer contains a pyrimidine derivative represented by the following general formula (2). The organic EL device of the present invention has a high efficiency, and is driven at a low driving voltage. Further, it has a particularly long lifetime.
(Continued)

9 CATHODE
8 ELECTRON INJECTION LAYER
7 ELECTRON TRANSPORT LAYER
6 LUMINOUS LAYER
5 SECOND HOLE TRANSPORT LAYER
4 FIRST HOLE TRANSPORT LAYER
3 HOLE INJECTION LAYER
2 TRANSPARENT ANODE
1 GLASS SUBSTRATE

US 10,950,797 B2
Page 2

(56) References Cited

U.S. PATENT DOCUMENTS

| | | | |
|---|---|---|---|
| 5,792,557 A | 8/1998 | Nakaya et al. | |
| 7,357,992 B2 | 4/2008 | Kato et al. | |
| 7,402,701 B2 | 7/2008 | Kato et al. | |
| 7,759,030 B2 | 7/2010 | Abe et al. | |
| 7,799,492 B2 | 9/2010 | Abe et al. | |
| 2004/0137270 A1* | 7/2004 | Seo | C09K 11/06 428/690 |
| 2006/0115680 A1 | 6/2006 | Hwang et al. | |
| 2007/0231503 A1 | 10/2007 | Hwang et al. | |
| 2008/0107919 A1 | 5/2008 | Hwang et al. | |
| 2008/0124572 A1 | 5/2008 | Mizuki et al. | |
| 2011/0175123 A1 | 7/2011 | Koh et al. | |
| 2012/0211733 A1 | 8/2012 | Hwang et al. | |
| 2013/0187137 A1 | 7/2013 | Mizuki et al. | |
| 2014/0299192 A1 | 10/2014 | Lee et al. | |
| 2015/0221872 A1 | 8/2015 | Hwang et al. | |
| 2015/0380657 A1 | 12/2015 | Yokoyama et al. | |
| 2016/0126464 A1 | 5/2016 | Yokoyama et al. | |
| 2016/0141514 A1 | 5/2016 | Lee et al. | |
| 2016/0172598 A1 | 6/2016 | Lee et al. | |
| 2016/0226000 A1 | 8/2016 | Kim et al. | |
| 2017/0005273 A1 | 1/2017 | Hwang et al. | |

FOREIGN PATENT DOCUMENTS

| | | |
|---|---|---|
| JP | 3-48656 | 2/1996 |
| JP | 3194657 | 6/2001 |
| JP | 2005-108804 | 4/2005 |
| JP | 2006-151979 | 6/2006 |
| JP | 2010-241687 | 10/2010 |
| JP | 2011-146387 | 7/2011 |
| JP | 4943840 | 3/2012 |
| JP | 2015-524797 | 8/2015 |
| KR | 10-2013-0060157 | 6/2013 |
| WO | 2008/062636 | 5/2008 |
| WO | 2014/129201 | 8/2014 |
| WO | 2014/199567 | 12/2014 |
| WO | 2014/208829 | 12/2014 |
| WO | 2014/209028 | 12/2014 |

OTHER PUBLICATIONS

International Search Report issued in International Bureau of WIPO Patent Application No. PCT/JP2016/077297, dated Nov. 22, 2016.

\* cited by examiner

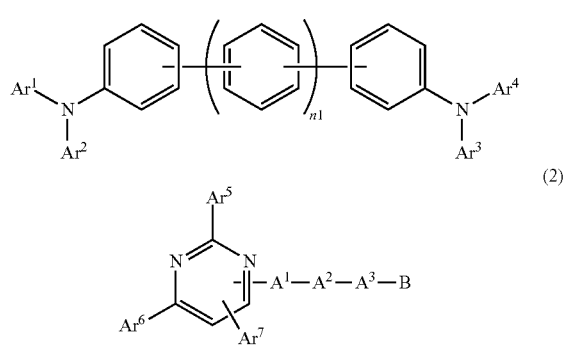

(1)

(2)

12 Claims, 38 Drawing Sheets

(51) Int. Cl.
C07C 211/54 (2006.01)
C07C 211/61 (2006.01)
C07D 401/10 (2006.01)
C09K 11/06 (2006.01)
H01L 51/56 (2006.01)

(52) U.S. Cl.
CPC ............ *C07D 401/10* (2013.01); *C09K 11/06* (2013.01); *H01L 51/006* (2013.01); *H01L 51/0052* (2013.01); *H01L 51/0067* (2013.01); *H01L 51/50* (2013.01); *H01L 51/5064* (2013.01); *C07C 2603/18* (2017.05); *C07C 2603/42* (2017.05); *C09K 2211/1007* (2013.01); *C09K 2211/1011* (2013.01); *C09K 2211/1014* (2013.01); *C09K 2211/1018* (2013.01); *H01L 51/001* (2013.01); *H01L 51/0054* (2013.01); *H01L 51/0058* (2013.01); *H01L 51/5012* (2013.01); *H01L 51/5072* (2013.01); *H01L 51/56* (2013.01); *H01L 2251/558* (2013.01)

9 CATHODE

8 ELECTRON INJECTION LAYER

7 ELECTRON TRANSPORT LAYER

6 LUMINOUS LAYER

5 SECOND HOLE TRANSPORT LAYER

4 FIRST HOLE TRANSPORT LAYER

3 HOLE INJECTION LAYER

2 TRANSPARENT ANODE

1 GLASS SUBSTRATE (1-47)
 (1-48)
 (1-49)
 (1-50)
 (1-51)
 (1-52)
 (1-53)
 (1-54)
 (1-55)
 (1-56)

(1-57)

(1-58)

(1-59)

(1-60)

(1-61)

(1-62)

(1-63)

(1-64)

(1-65)

(1-66)

(2-47)

(2-48)

(2-49)

(2-50)

(2-51)

(2-52)

(2-53)

(2-54)

(2-81)　(2-82)

(2-83)　(2-84)

(2-85)　(2-86)

(2-87)　(2-88)

(2-115)

(2-116)

(2-117)

(2-118)

(2-119)

(2-120)

(2-121)

(2-122)

(2-123)

(2-124)

(2-125)   (2-126)

(3-1)

(3-2)

(3-3)

(3-4)

(3-5)

(3-6)

(3-7)

(3-8)

(3-14)

(3-15)

(3-16)

(3-17)

(3'-1)　　　(3'-2)

ORGANIC ELECTROLUMINESCENT DEVICE

TECHNICAL FIELD

This invention relates to an organic electroluminescent device (will hereinafter be referred to simply as an organic EL device) which is a self light-emitting device preferred for various displays. More specifically, the invention relates to an organic EL device using a specific arylamine compound and a specific pyrimidine derivative.

BACKGROUND ART

Since an organic EL device is a self light-emitting device, it is brighter, better in visibility, and capable of clearer display, than a liquid crystal device. Hence, energetic researches have been conducted on organic EL devices.

In 1987, C. W. Tang et al. of Eastman Kodak developed a laminated structure device sharing various roles among different materials, thereby imparting practical applicability to organic EL devices using organic materials. Such an organic EL device is formed by laminating a layer of a fluorescent body capable of transporting electrons, and a layer of an organic substance capable of transporting holes. Because of this configuration, the organic EL device injected positive charges and negative charges into the layer of the fluorescent body to perform light emission, thereby obtaining a high luminance of 1,000 cd/m$^2$ or more at a voltage of 10V or less (see Patent Document 1 and Patent Document 2).

Many improvements have been made to date for commercialization of organic EL devices. For example, high efficiency and high durability have been achieved by an electroluminescent device, in which the roles of the respective layers in a laminated structure are rendered more diverse, and an anode, a hole injection layer, a hole transport layer, a luminous layer, an electron transport layer, an electron injection layer, and a cathode are provided sequentially on a substrate.

For a further increase in the luminous efficiency, it has been attempted to utilize triplet excitons, and the utilization of phosphorescent compounds has been considered. Furthermore, devices utilizing light emission by thermally activated delayed fluorescence (TADF) have been developed. In 2011, Adachi et al. of Kyushu University realized an external quantum efficiency of 5.3% by a device using a thermally activated delayed fluorescence material.

The luminous layer can also be prepared by doping a charge transporting compound, generally called a host material, with a fluorescent compound, a phosphorescent compound, or a material radiating delayed fluorescence. The selection of the organic material in the organic EL device greatly affects the characteristics of the device, such as efficiency and durability.

With the organic EL device, the charges injected from both electrodes recombine in the luminous layer to obtain light emission. For this purpose, how efficiently the charges of the holes and the electrons are passed on to the luminous layer is of importance in the organic EL device, and the device needs to be excellent in carrier balance. Moreover, the hole injecting properties are enhanced, and the electron blocking properties of blocking electrons injected from the cathode are enhanced, whereby the probability of the holes and the electrons recombining is increased. Besides, excitons generated within the luminous layer are confined. By so doing, a high luminous efficiency can be obtained. Thus, the role of the hole transport material is so important that there has been a desire for a hole transport material having high hole injection properties, allowing marked hole mobility, possessing high electron blocking properties, and having high durability to electrons.

From the viewpoint of device lifetime, heat resistance and amorphousness of the material are also important. A material with low thermal resistance is thermally decomposed even at a low temperature by heat produced during device driving, and the material deteriorates. With a material having low amorphousness, crystallization of a thin film occurs even in a short time, and the device deteriorates. Thus, high resistance to heat and satisfactory amorphousness are required of the material to be used.

As hole transport materials for organic EL devices, N,N'-diphenyl-N,N'-di($\alpha$-naphthyl)benzidine (NPD) and various aromatic amine derivatives have been known (see Patent Documents 1 and 2). NPD has satisfactory hole transport capability, but its glass transition point (Tg) serving as an index of heat resistance is as low as 96° C. Under high temperature conditions, it causes decline in device characteristics due to crystallization. Among the aromatic amine derivatives described in Patent Documents 1 and 2 are compounds having excellent hole mobility of 10$^{-3}$ cm$^2$/Vs or more. Since the electron blocking properties of such aromatic amine derivatives are insufficient, however, some of electrons pass through the luminous layer, and an increase in the luminous efficiency cannot be expected. Thus, there has been a desire for a material having higher electron blocking properties, more stable in the form of a thin film, and possessing higher resistance to heat, in order to achieve an even higher efficiency. Patent Document 3 reports aromatic amine derivatives with high durability. However, the aromatic amine derivatives of Patent Document 3 are used as charge transport materials for electrophotographic photoreceptors, and there have been no examples of their use in organic EL devices.

As compounds improved in characteristics such as heat resistance and hole injection properties, arylamine compounds having substituted carbazole structures have been proposed (see Patent Documents 4 and 5). In devices using these compounds as hole injection layers or hole transport layers, heat resistance and luminous efficiency have been improved. However, the improved characteristics have been still insufficient, and an even lower driving voltage and an even higher luminous efficiency are desired.

In the field of organic EL devices, as noted above, it is desired to combine materials excellent in hole injection/transport performance, electron injection/transport performance, thin film stability, durability, etc., thereby improving the device characteristics, increasing the yield of device preparation, and enabling holes and electrons to be recombined with high efficiency. Realization of a device with a high luminous efficiency, a low driving voltage, and a long lifetime through these efforts is desired.

It is also desired to combine materials excellent in hole injection/transport performance, electron injection/transport performance, thin film stability, durability, etc., thereby realizing an organic EL device improved in device characteristics, offering a good carrier balance, and having a high efficiency, a low driving voltage, and a long lifetime.

PRIOR ART DOCUMENTS

Patent Documents

Patent Document 1: JP-A-H-8-048656
Patent Document 2: Japanese Patent No. 3194657
Patent Document 3: Japanese Patent No. 4943840
Patent Document 4: JP-A-2006-151979
Patent Document 5: WO2008/62636
Patent Document 6: KR-A-2013-060157
Patent Document 7: JP-A-H-7-126615
Patent Document 8: JP-A-H-8-048656
Patent Document 9: JP-A-2005-108804

SUMMARY OF THE INVENTION

Problems to be Solved by the Invention

The present invention involves combining various materials for an organic EL device, which are excellent in hole injection/transport performance, electron injection/transport performance, electron blocking capability, stability in a thin film state, durability, etc. The present invention has as its object to provide, by so doing, an organic EL device which effectively exhibits the characteristics of the respective materials, and which (1) is high in luminous efficiency and power efficiency, (2) is low in light emission starting voltage, (3) is low in practical driving voltage, and (4) has a long lifetime.

Means for Solving the Problems

In an attempt to attain the above object, the present inventors focused on the facts that arylamine-based materials were excellent in hole injection/transport performance, thin film stability and durability, and that pyrimidine derivatives were excellent in electron injection/transport performance, thin film stability, and durability. They selected an arylamine compound having a specific structure, as a material for the hole transport layer (second hole transport layer) adjacent to the luminous layer, in order to make holes injectable and transportable efficiently into the luminous layer. The inventors also selected a pyrimidine derivative having a specific structure, as a material for the electron transport layer, in order to make electrons injectable and transportable efficiently into the luminous layer. The inventors combined various materials with these compounds to prepare organic EL devices, and energetically evaluated their device characteristics.

In order that holes could be injected and transported into the luminous layer more efficiently, the inventors combined a triarylamine compound having a specific structure, as a material for the first hole transport layer, with the above material for the second hole transport layer and the above material for the electron transport layer. That is, the inventors selected combinations of the materials with elaborated carrier balance. Combining these materials and various materials, the inventors prepared various organic EL devices, and energetically evaluated their device characteristics.

As a result, the present invention has been accomplished. That is, according to the present invention, 1) There is provided an organic EL device having at least an anode, a first hole transport layer, a second hole transport layer, a luminous layer, an electron transport layer, and a cathode in this order, wherein the second hole transport layer contains an arylamine compound represented by the following general formula (1), and the electron transport layer contains a pyrimidine derivative represented by the following general formula (2):

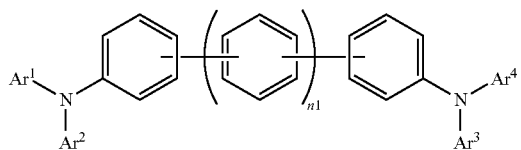

where $Ar^1$ to $Ar^4$ may be identical or different, and each represents an aromatic hydrocarbon group, an aromatic heterocyclic group, or a condensed polycyclic aromatic group, and n1 denotes an integer of 1 to 4.

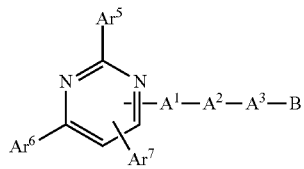

where $Ar^5$ and $Ar^6$ may be identical or different, and each represents an aromatic hydrocarbon group, an aromatic heterocyclic group, or a condensed polycyclic aromatic group, Ar⁷ represents a hydrogen atom, an aromatic hydrocarbon group, an aromatic heterocyclic group, or a condensed polycyclic aromatic group, A¹ and A² may be identical or different, and each represents a divalent group of an aromatic hydrocarbon, or a divalent group of a condensed polycyclic aromatic, A³ represents a divalent group of an aromatic hydrocarbon, a divalent group of a condensed polycyclic aromatic, or a single bond, and B represents an aromatic heterocyclic group.

Preferred embodiments of the organic EL device according to the present invention are as follows:

2) The first hole transport layer contains a hole transporting arylamine compound.

3) The first hole transport layer contains a triarylamine compound having 3 to 6 triarylamine structures in the molecule, the triarylamine structures being linked together by a single bond or a heteroatom-free divalent group.

4) The triarylamine compound having 3 to 6 triarylamine structures in the molecule is a triarylamine compound having 4 triarylamine structures in the molecule, the triarylamine compound being represented by the following general formula (3):

L¹ to L³ may be identical or different, and each represents a divalent group represented by any of the following structural formulas (B) to (G), or a single bond.

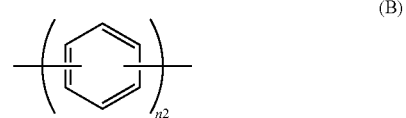
(B)

(C)

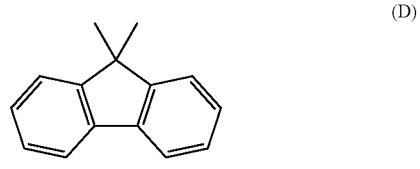
(D)

—CH₂— (E)

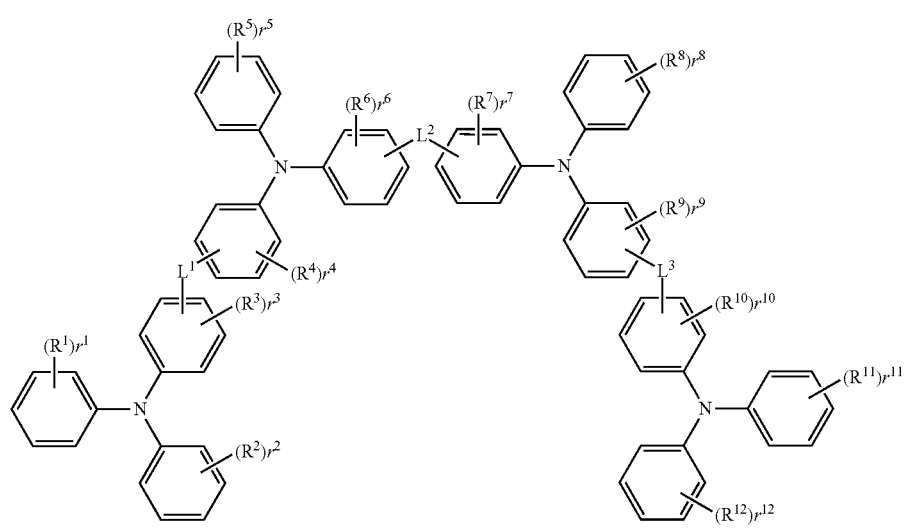
(3)

where
r¹, r², r⁵, r⁸, r¹¹ and r¹² each denotes an integer of 0 to 5,
r³, r⁴, r⁶, r⁷, r⁹ and r¹⁰ each denotes an integer of 0 to 4,
R¹ to R¹² may be identical or different, and each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxyl group and, if a plurality of these groups are bound to the same aromatic ring, the plurality of groups bound may be identical or different, and may bind to each other via a single bond, a methylene group, an oxygen atom, or a sulfur atom to form a ring, and -continued —CH— (F)

(G)

where n2 denotes an integer of 1 to 3.

5) The first hole transport layer contains a triarylamine compound having 2 triarylamine structures in the molecule, the triarylamine structures being linked together by a single bond or a heteroatom-free divalent group.

6) The triarylamine compound having 2 triarylamine structures in the molecule is represented by the following general formula (4):

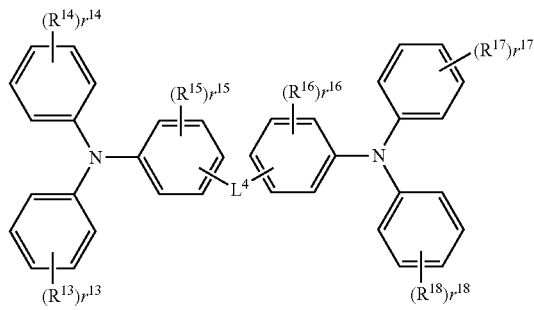

(4)

where $r^{13}$, $r^{14}$, $r^{17}$ and $r^{18}$ each denotes an integer of 0 to 5, while $r^{15}$ and $r^{16}$ each denotes an integer of 0 to 4, $R^{13}$ to $R^{18}$ may be identical or different, and each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxyl group and, if a plurality of these groups are bound to the same aromatic ring, the plurality of groups bound may be identical or different, and may bind to each other via a single bond, a methylene group, an oxygen atom, or a sulfur atom to form a ring, and $L^4$ represents a divalent group represented by any of the following structural formulas (C) to (G), or a single bond.

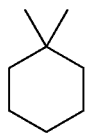
(C)

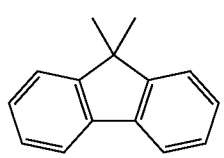
(D)

—CH₂—
(E)

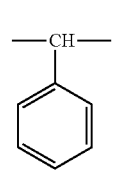
(F)

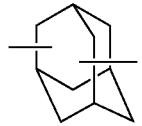
(G)

7) The pyrimidine derivative is represented by the following general formula (2a):

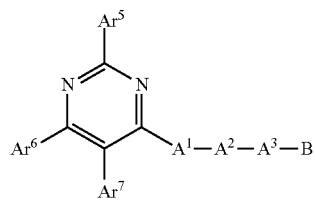

(2a)

where $Ar^5$ to $Ar^7$, $A^1$ to $A^3$, and B are as defined in the general formula (2).

8) The pyrimidine derivative is represented by the following general formula (2b):

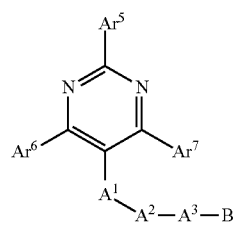

(2b)

where $Ar^5$ to $Ar^7$, $A^1$ to $A^3$, and B are as defined in the general formula (2).

9) The luminous layer contains a blue light emitting dopant.

10) The blue light emitting dopant is a pyrene derivative.

11) The luminous layer contains an anthracene derivative.

12) The luminous layer contains the anthracene derivative as a host material.

Effects of the Invention

The arylamine compound represented by the general formula (1) expresses high hole mobility, and is thus preferred as a material for the hole transport layer of an organic EL device. The pyrimidine derivative represented by the general formula (2) is excellent in electron injection/transport performance, and is preferred as a material for the electron transport layer of an organic EL device.

In a case of the organic EL device of the present invention, the materials for use in the respective layers are selected, with the carrier balance taken into consideration, from the viewpoints of hole injection/transport performance, electron injection/transport performance, thin film stability, and durability. Concretely, an arylamine compound having a specific structure and a pyrimidine derivative having a specific structure are combined. By so doing, the efficiency of hole transport from the hole transport layer to the luminous layer, and the efficiency of electron transport from the electron transport layer to the luminous layer are improved as compared with conventional organic EL devices. As a result, the organic EL device of the present invention is improved in the luminous efficiency, and is improved in durability because of a decrease in the driving voltage.

Moreover, the triarylamine compound represented by the general formula (3) or the general formula (4) expresses high hole mobility. In a preferred embodiment of the present invention, therefore, such a triarylamine compound having a specific structure is combined, as a material for the first hole transport layer, with a material for the second hole transport layer, whereby holes can be injected and transported more efficiently into the luminous layer, and a more elaborate carrier balance is achieved. Consequently, the luminous efficiency is further improved, and the driving voltage further declines, so that the durability is further improved.

According to the present invention, as described above, an organic EL device having a high efficiency, working at a low driving voltage, and possessing a particularly long lifetime has been realized.

MODE FOR CARRYING OUT THE INVENTION

The organic EL device of the present invention has a basic structure in which an anode, a first hole transport layer, a second hole transport layer, a luminous layer, an electron transport layer, and a cathode are provided in this order on a substrate such as a glass substrate or a transparent plastic substrate (e.g., polyethylene terephthalate substrate).

Figure 1:
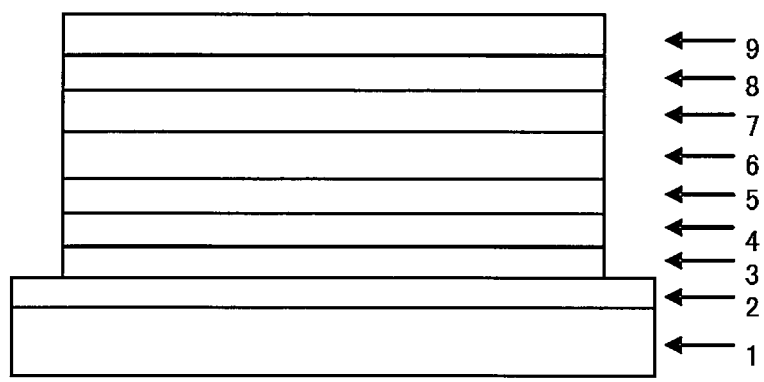
FIG. 1 is a view showing the configuration of organic EL devices of Device Examples 1 to 2 and Device Comparative Examples 1 to 2.
Figure 2:
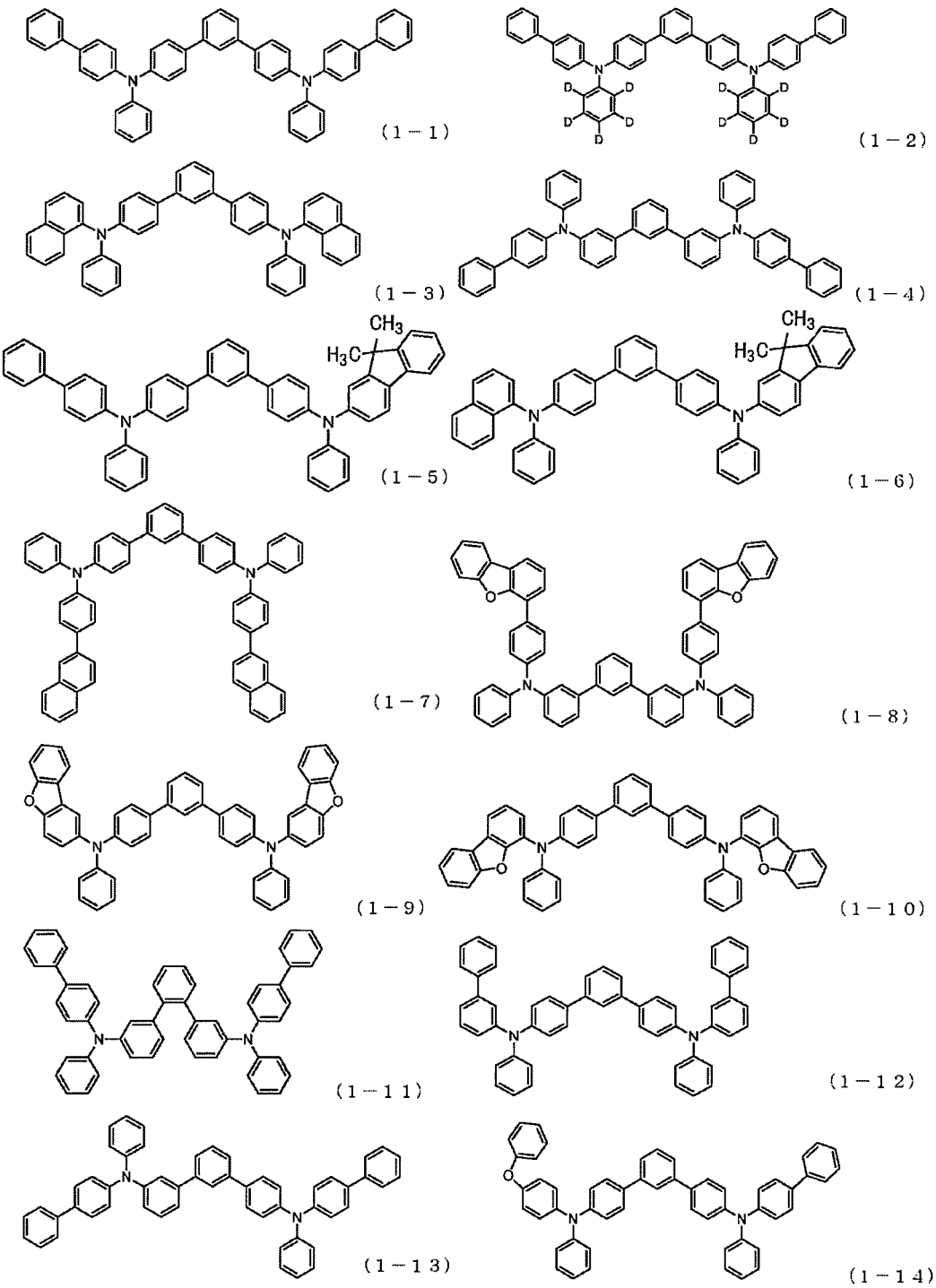
FIG. 2 is a view showing the structural formulas of Compounds 1-1 to 1-14 which are arylamine compounds I.
Figure 3:
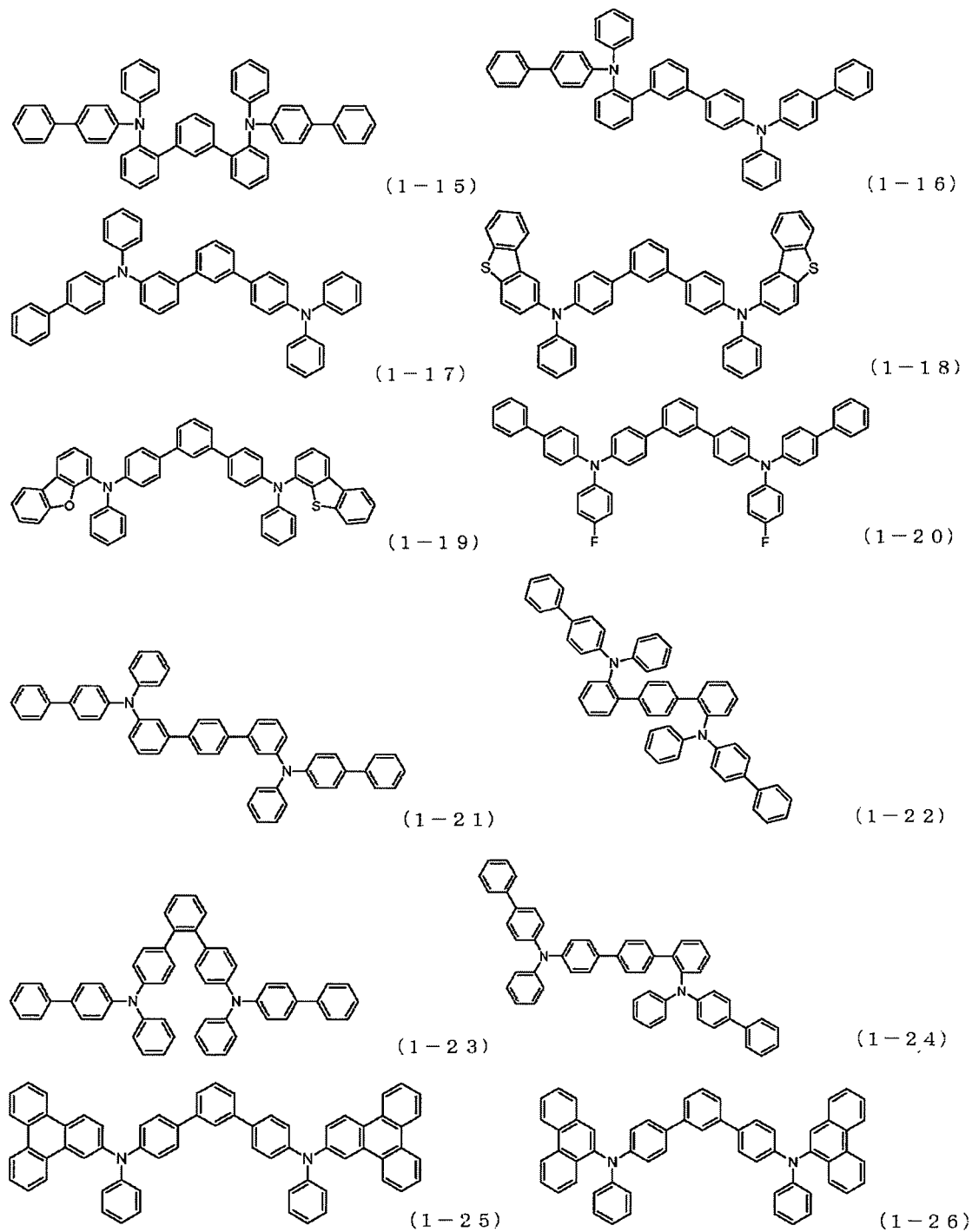
FIG. 3 is a view showing the structural formulas of Compounds 1-15 to 1-26 which are arylamine compounds I.
Figure 4:
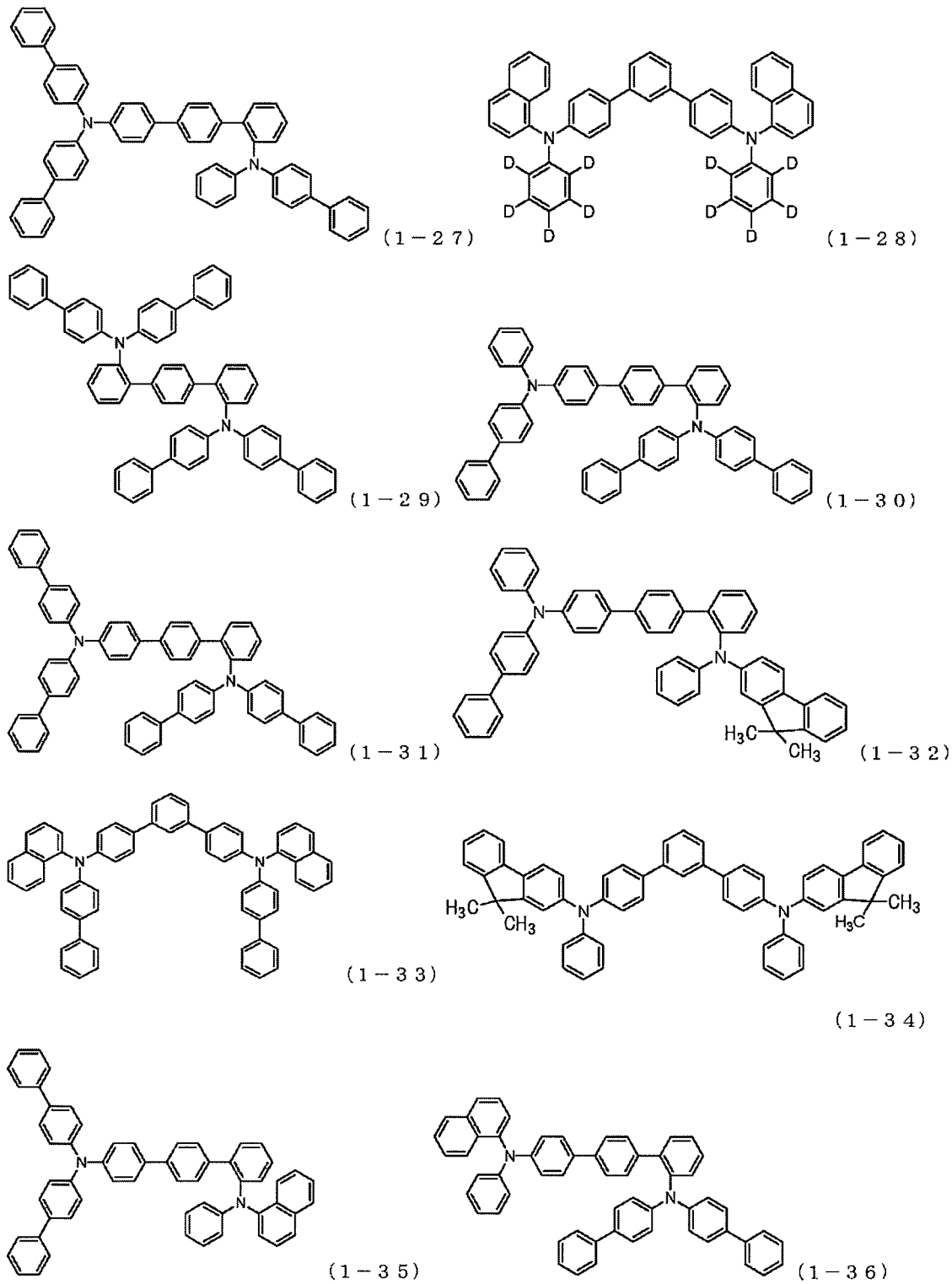
FIG. 4 is a view showing the structural formulas of Compounds 1-27 to 1-36 which are arylamine compounds I.
Figure 5:
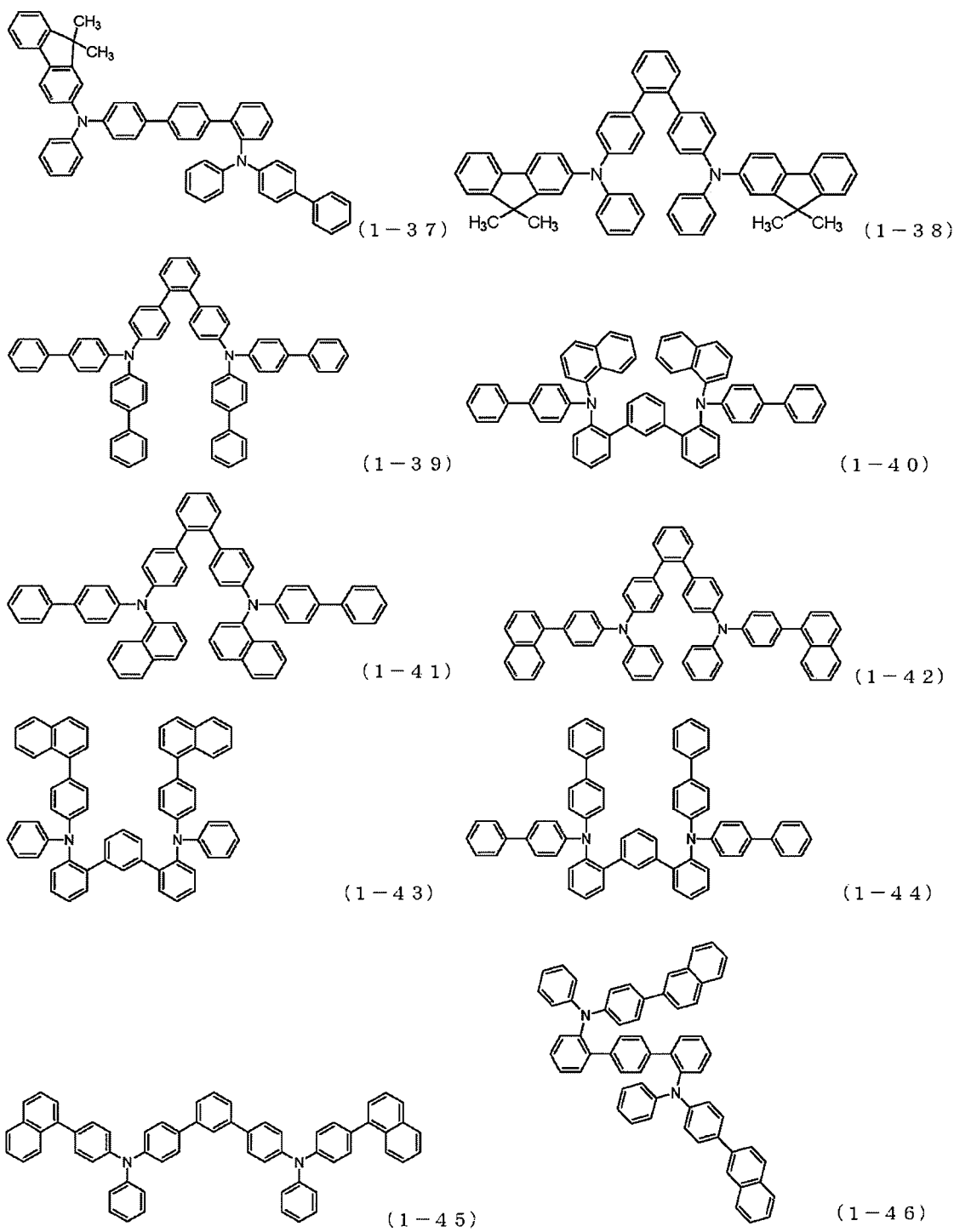
FIG. 5 is a view showing the structural formulas of Compounds 1-37 to 1-46 which are arylamine compounds I.
Figure 6:
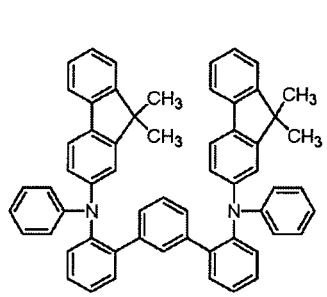
FIG. 6 is a view showing the structural formulas of Compounds 1-47 to 1-56 which are arylamine compounds I.
Figure 6:
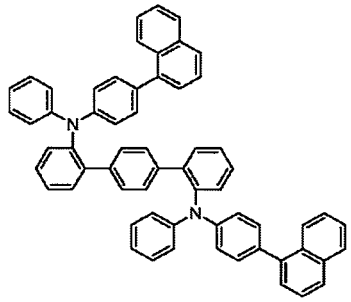
Figure 6:
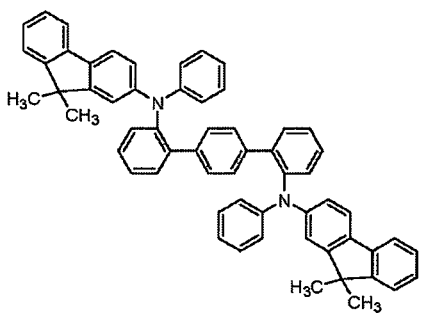
Figure 6:
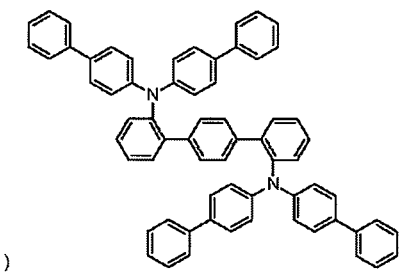
Figure 6:
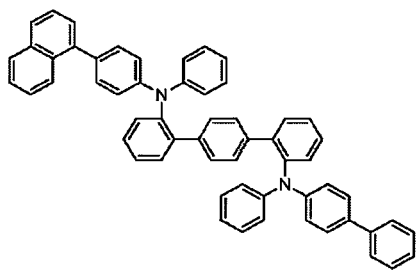
Figure 6:
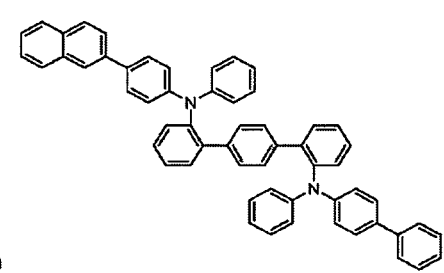
Figure 6:
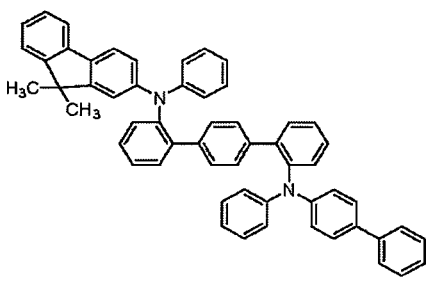
Figure 6:
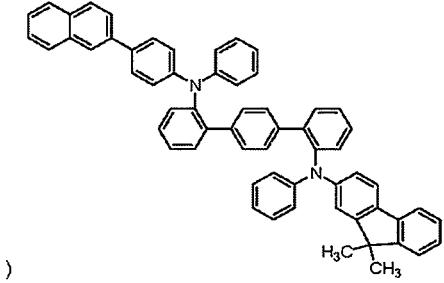
Figure 6:
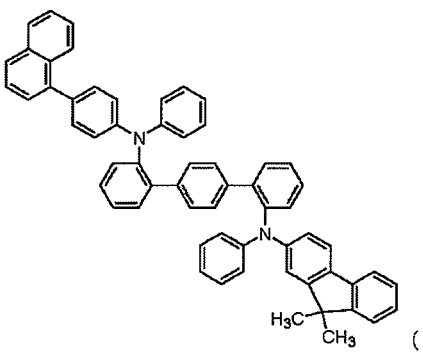
Figure 6:
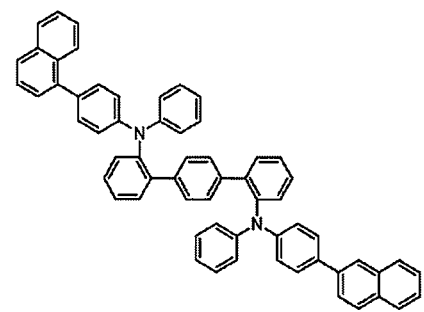
Figure 7:
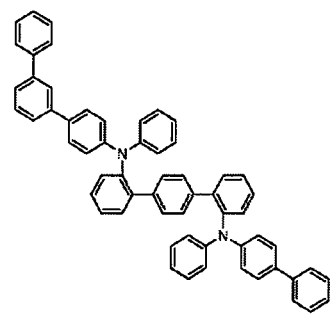
FIG. 7 is a view showing the structural formulas of Compounds 1-57 to 1-66 which are arylamine compounds I.
Figure 7:
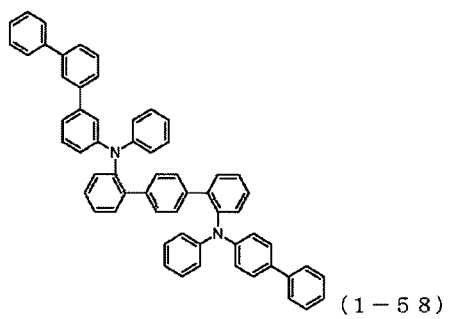
Figure 7:
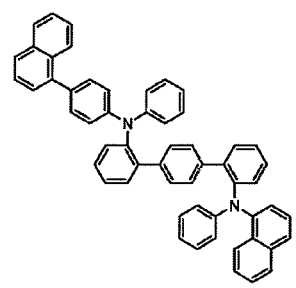
Figure 7:
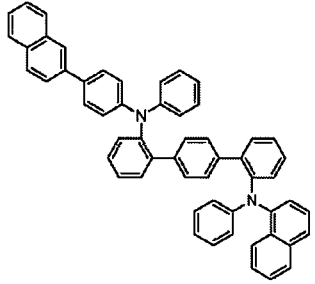
Figure 7:
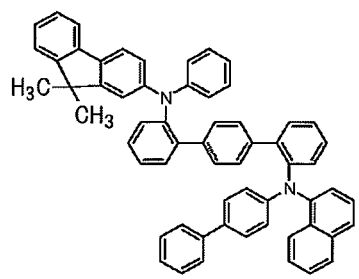
Figure 7:
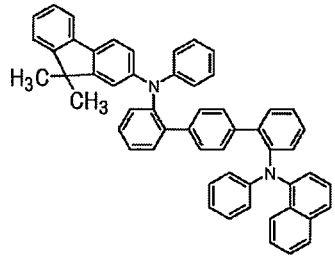
Figure 7:
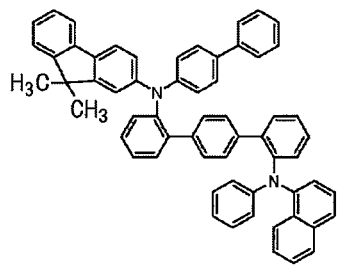
Figure 7:
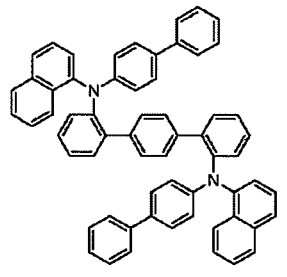
Figure 7:
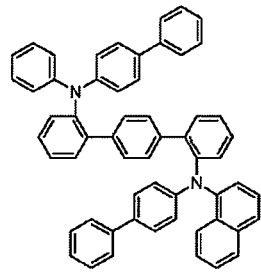
Figure 7:
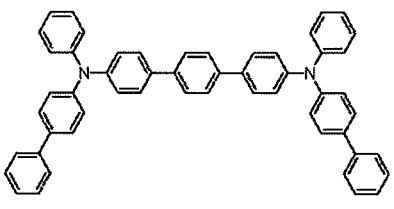
Figure 8:
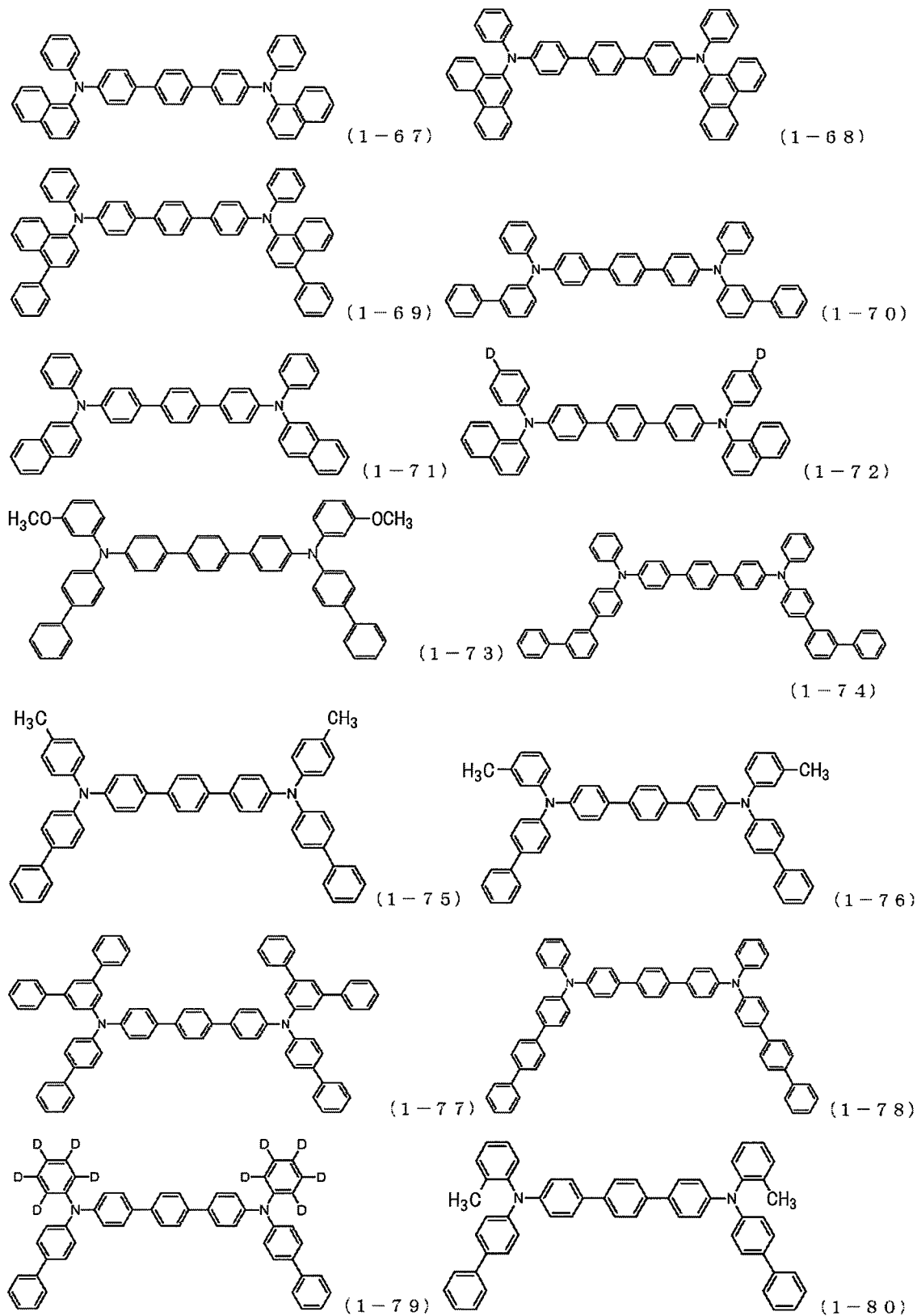
FIG. 8 is a view showing the structural formulas of Compounds 1-67 to 1-80 which are arylamine compounds I.
Figure 9:
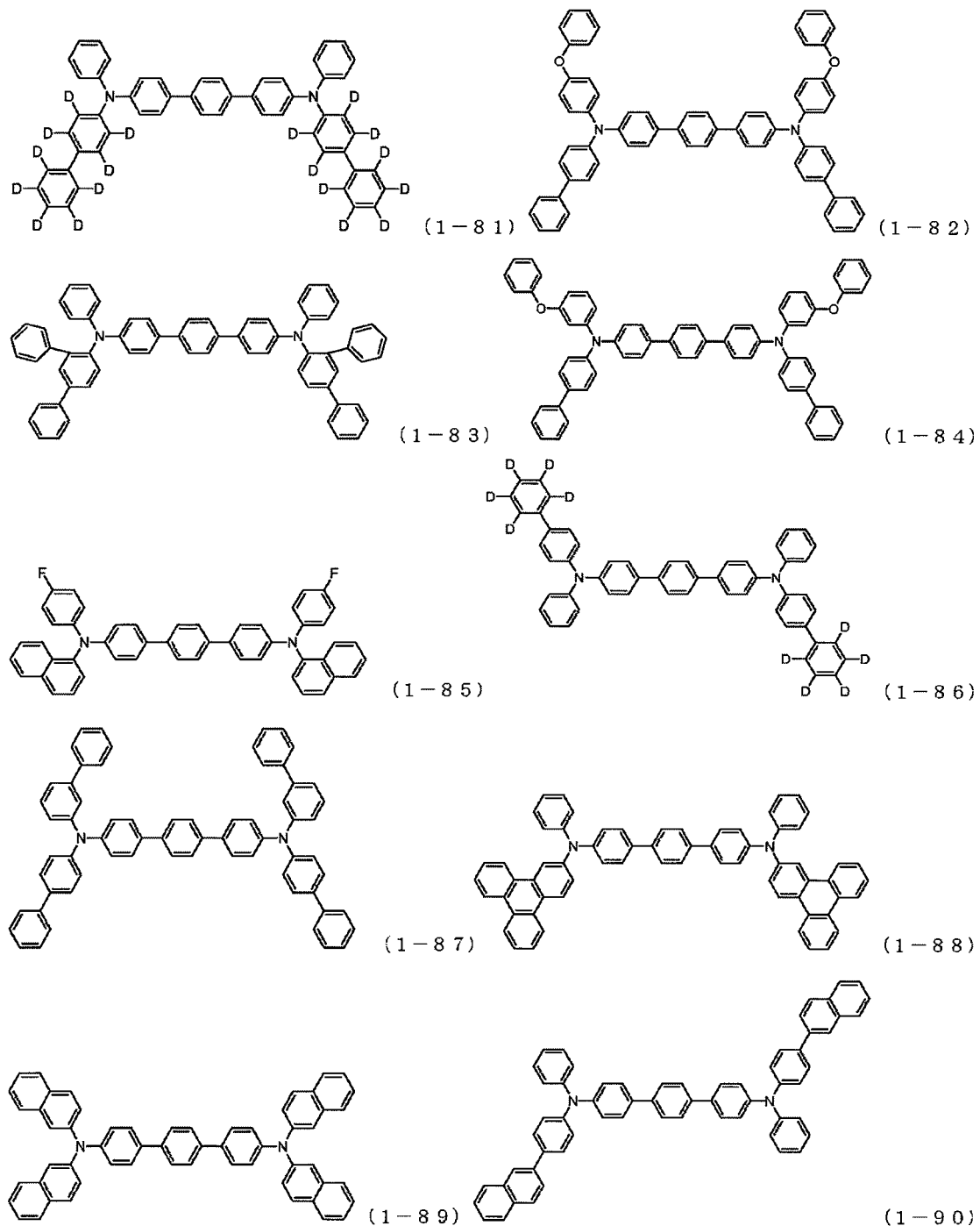
FIG. 9 is a view showing the structural formulas of Compounds 1-81 to 1-90 which are arylamine compounds I.
Figure 10:
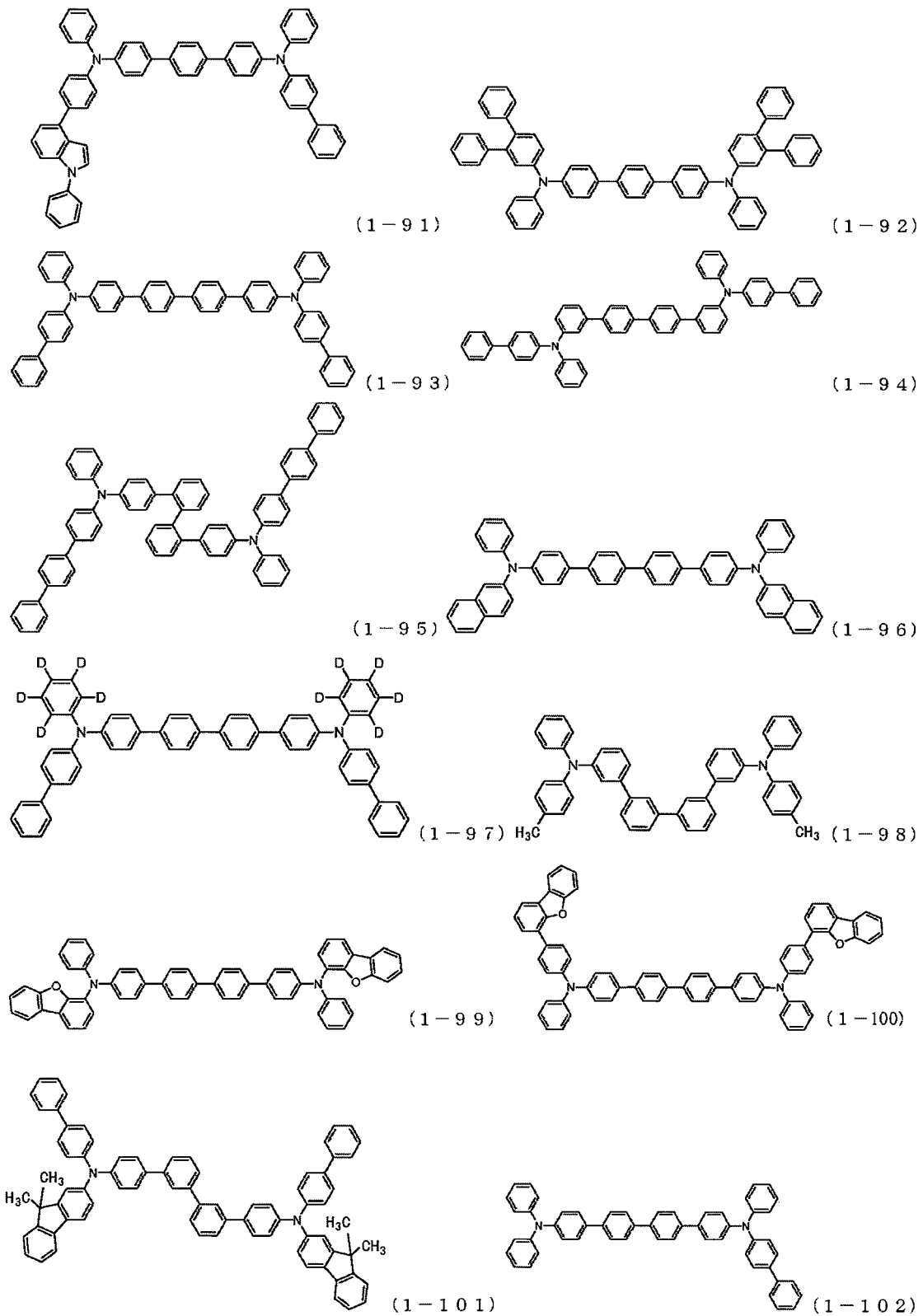
FIG. 10 is a view showing the structural formulas of Compounds 1-91 to 1-102 which are arylamine compounds I.
Figure 11:
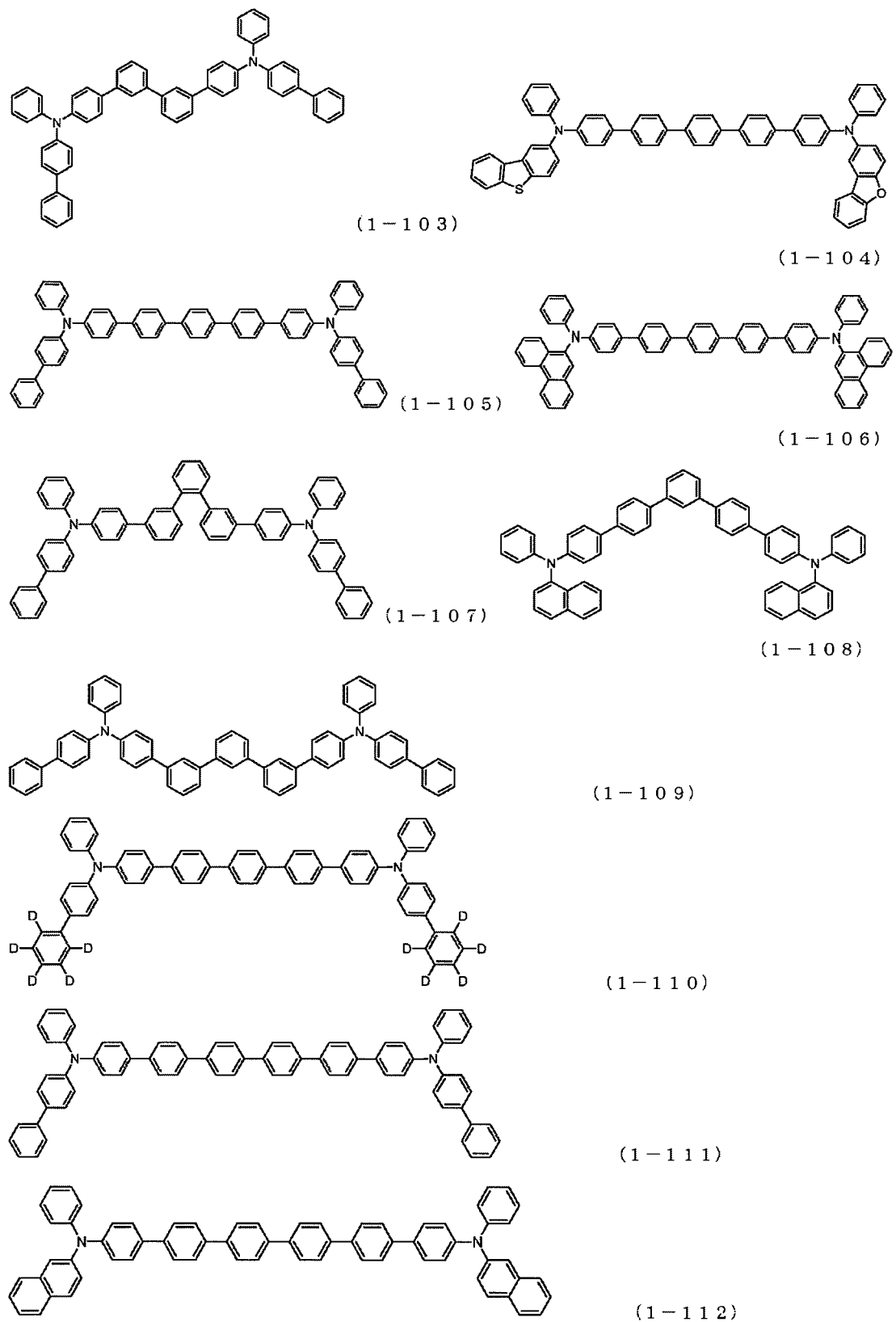
FIG. 11 is a view showing the structural formulas of Compounds 1-103 to 1-112 which are arylamine compounds I.
Figure 12:
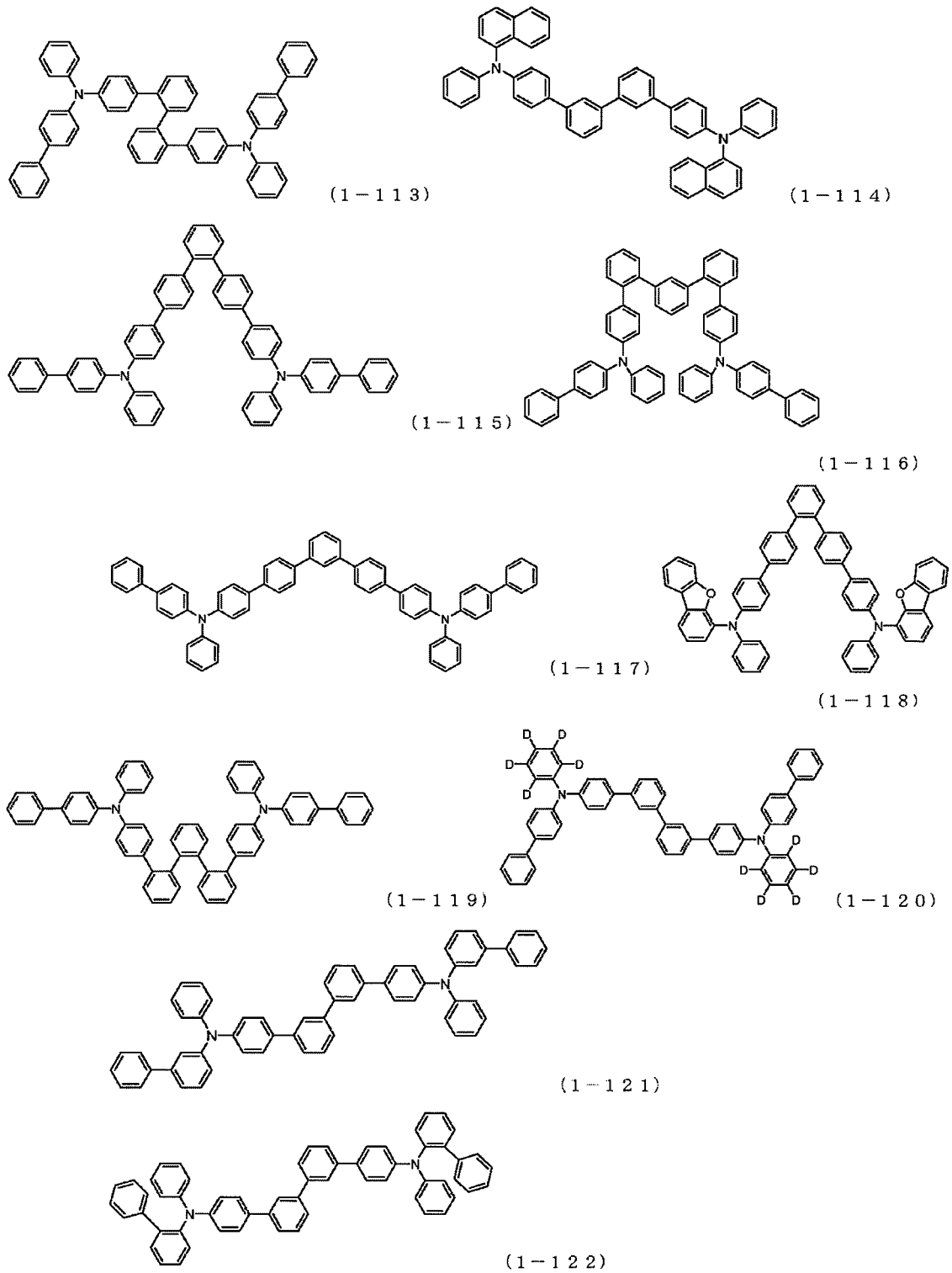
FIG. 12 is a view showing the structural formulas of Compounds 1-113 to 1-122 which are arylamine compounds I.
Figure 13:
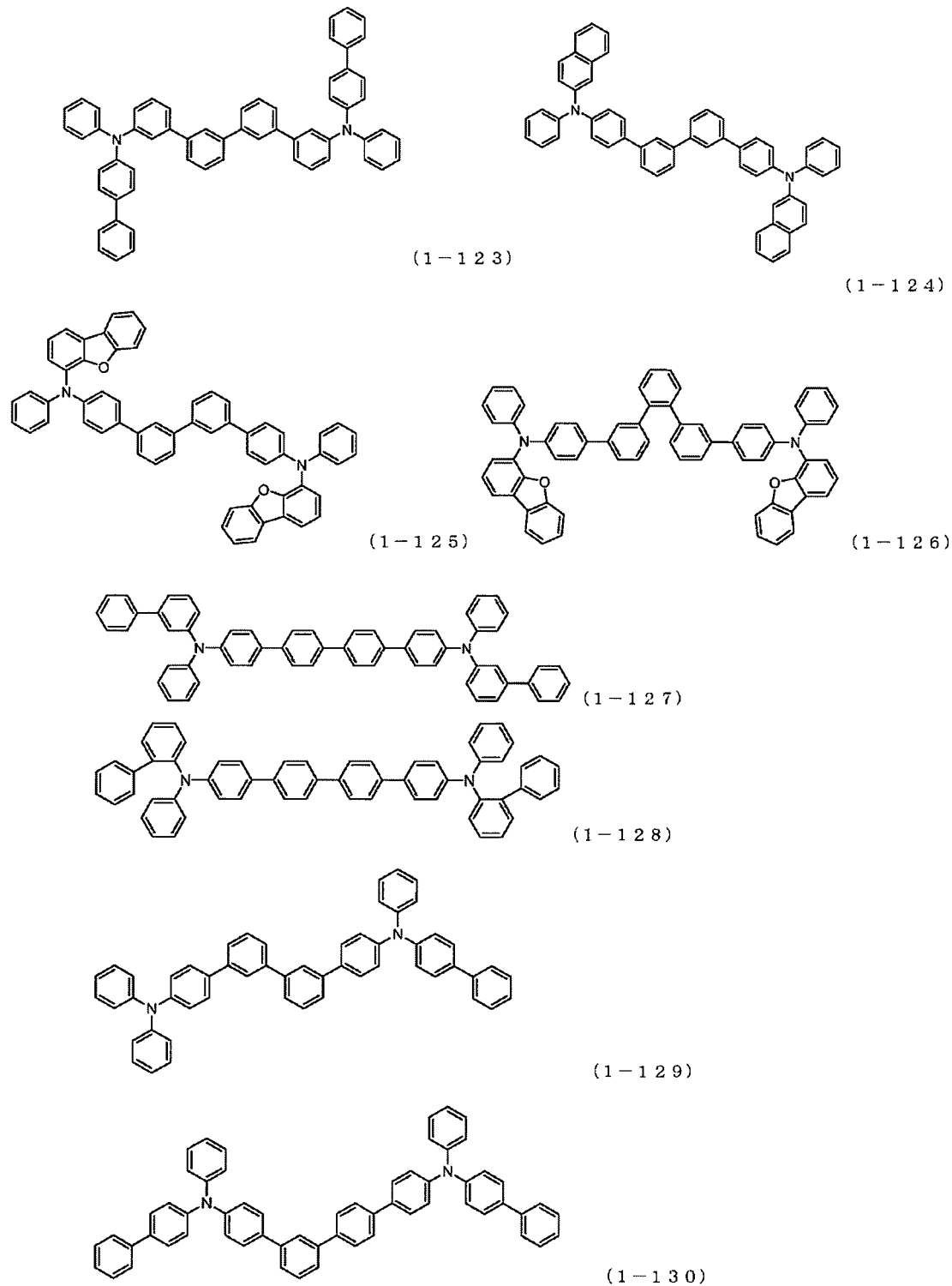
FIG. 13 is a view showing the structural formulas of Compounds 1-123 to 1-130 which are arylamine compounds I.
Figure 14:
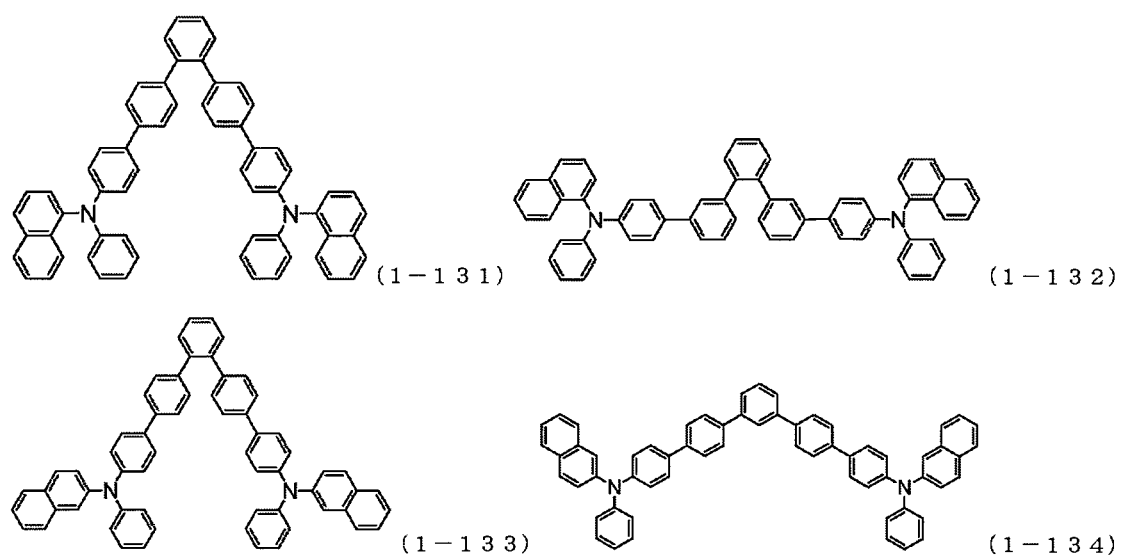
FIG. 14 is a view showing the structural formulas of Compounds 1-131 to 1-134 which are arylamine compounds I.
Figure 15:
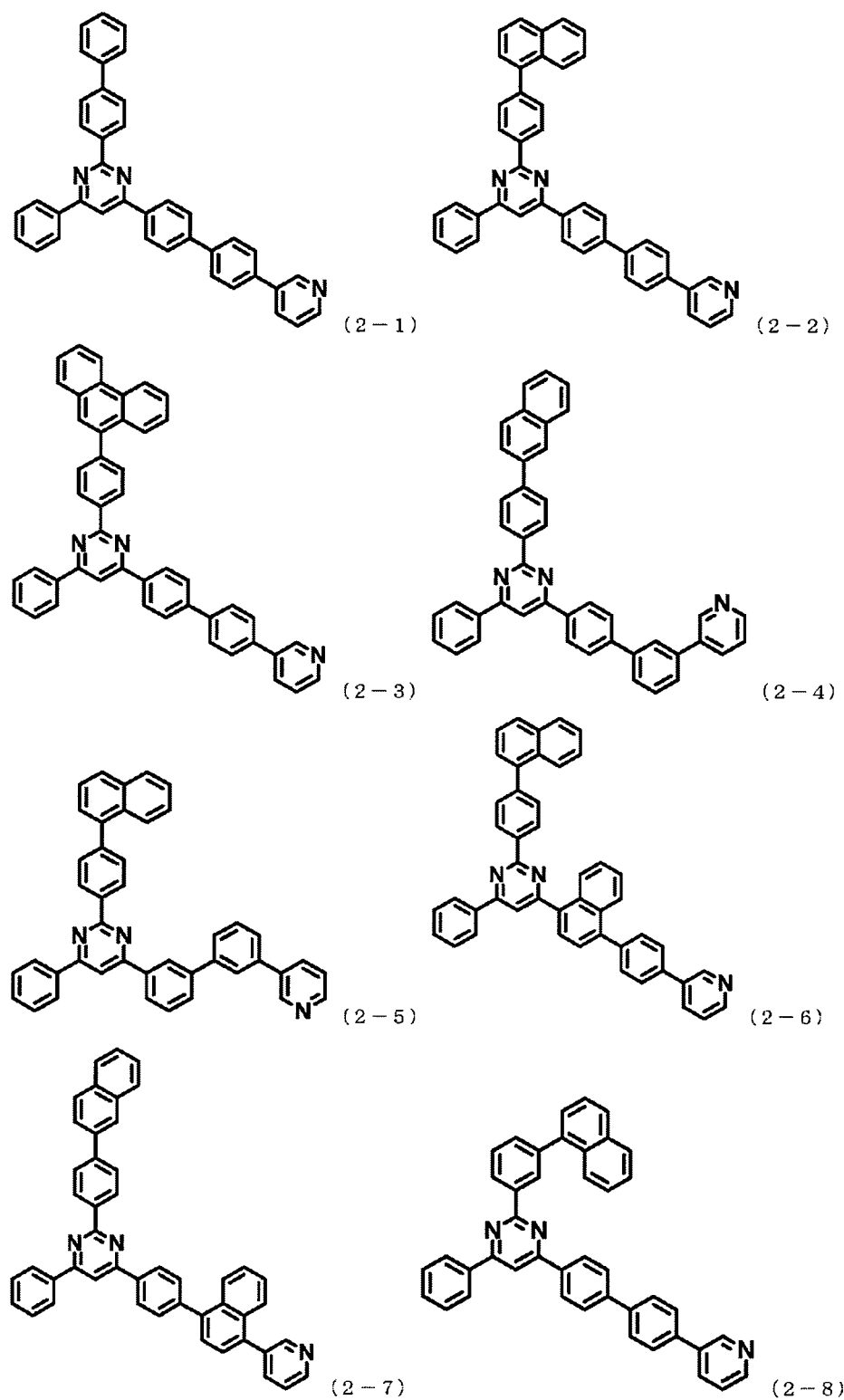
FIG. 15 is a view showing the structural formulas of Compounds 2-1 to 2-8 which are pyrimidine derivatives II.
Figure 16:
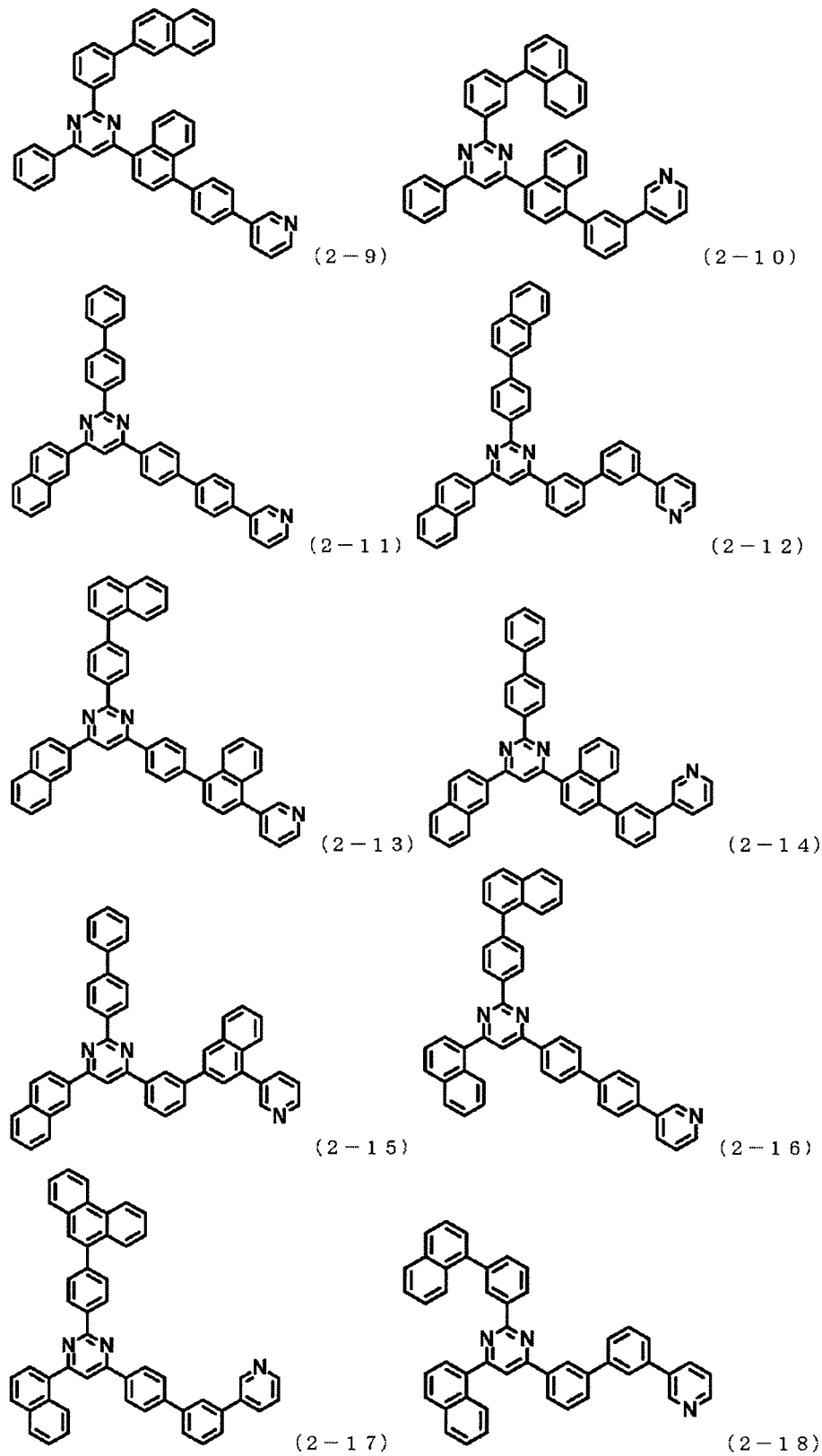
FIG. 16 is a view showing the structural formulas of Compounds 2-9 to 2-18 which are pyrimidine derivatives II.
Figure 17:
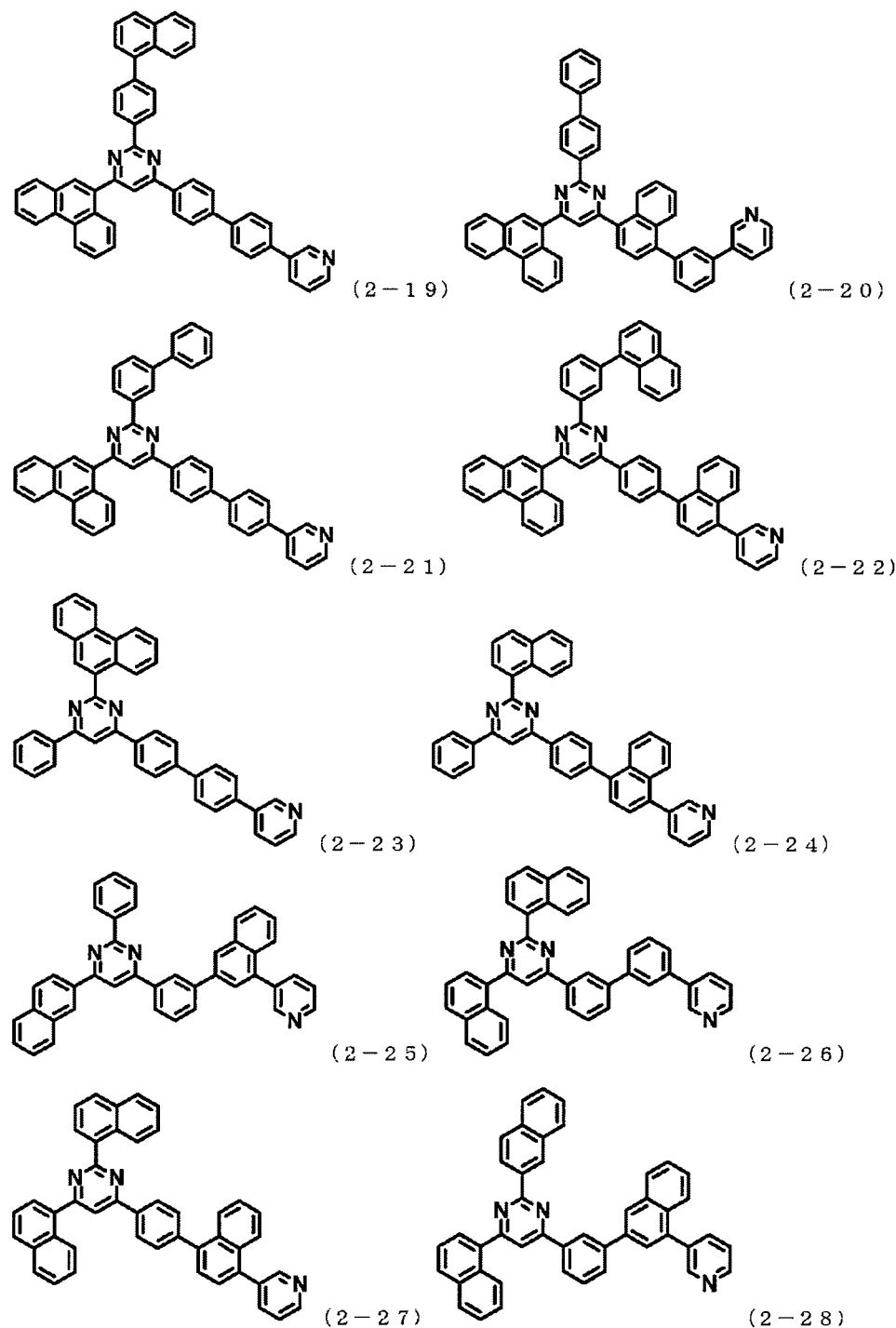
FIG. 17 is a view showing the structural formulas of Compounds 2-19 to 2-28 which are pyrimidine derivatives II.
Figure 18:
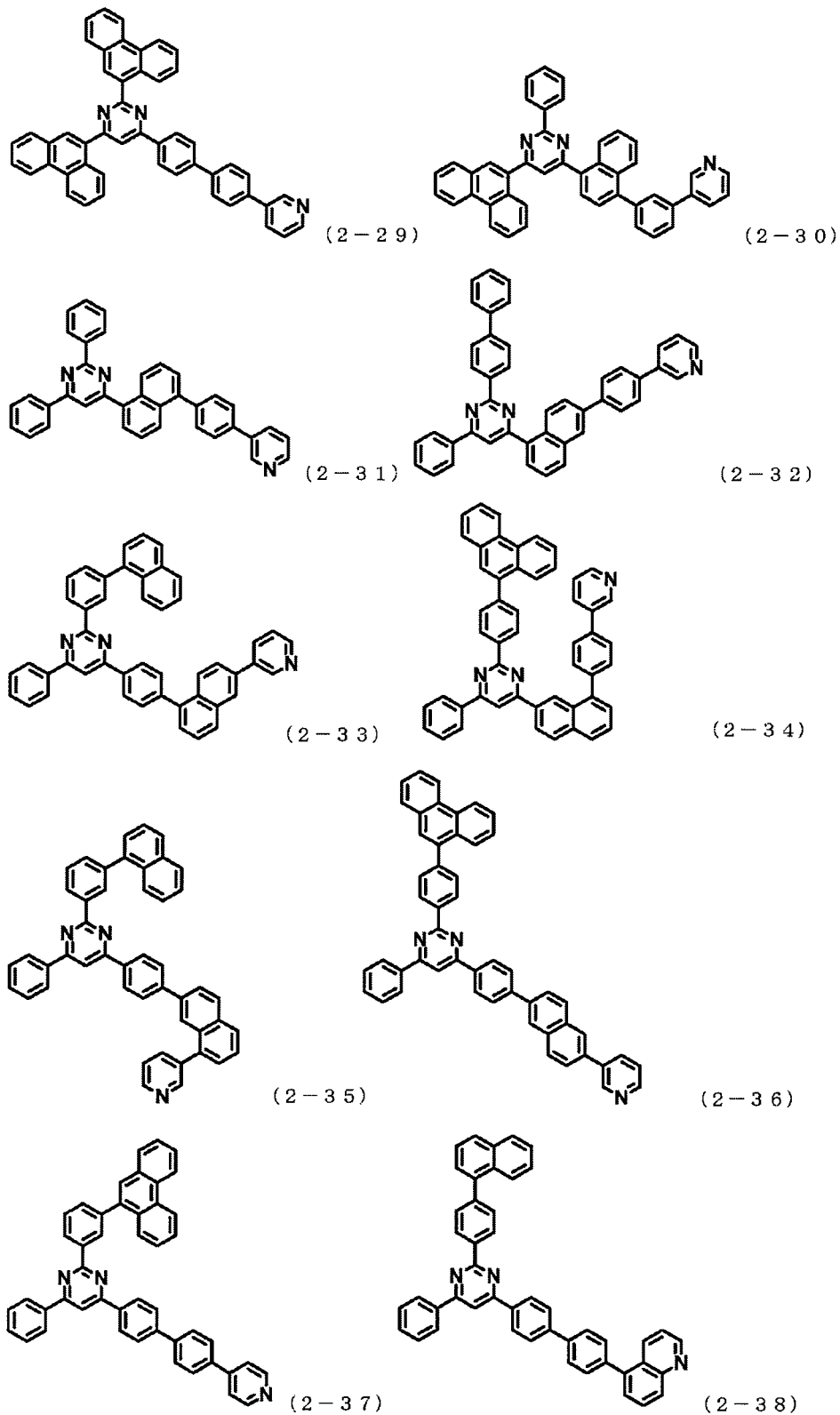
FIG. 18 is a view showing the structural formulas of Compounds 2-29 to 2-38 which are pyrimidine derivatives II.
Figure 19:
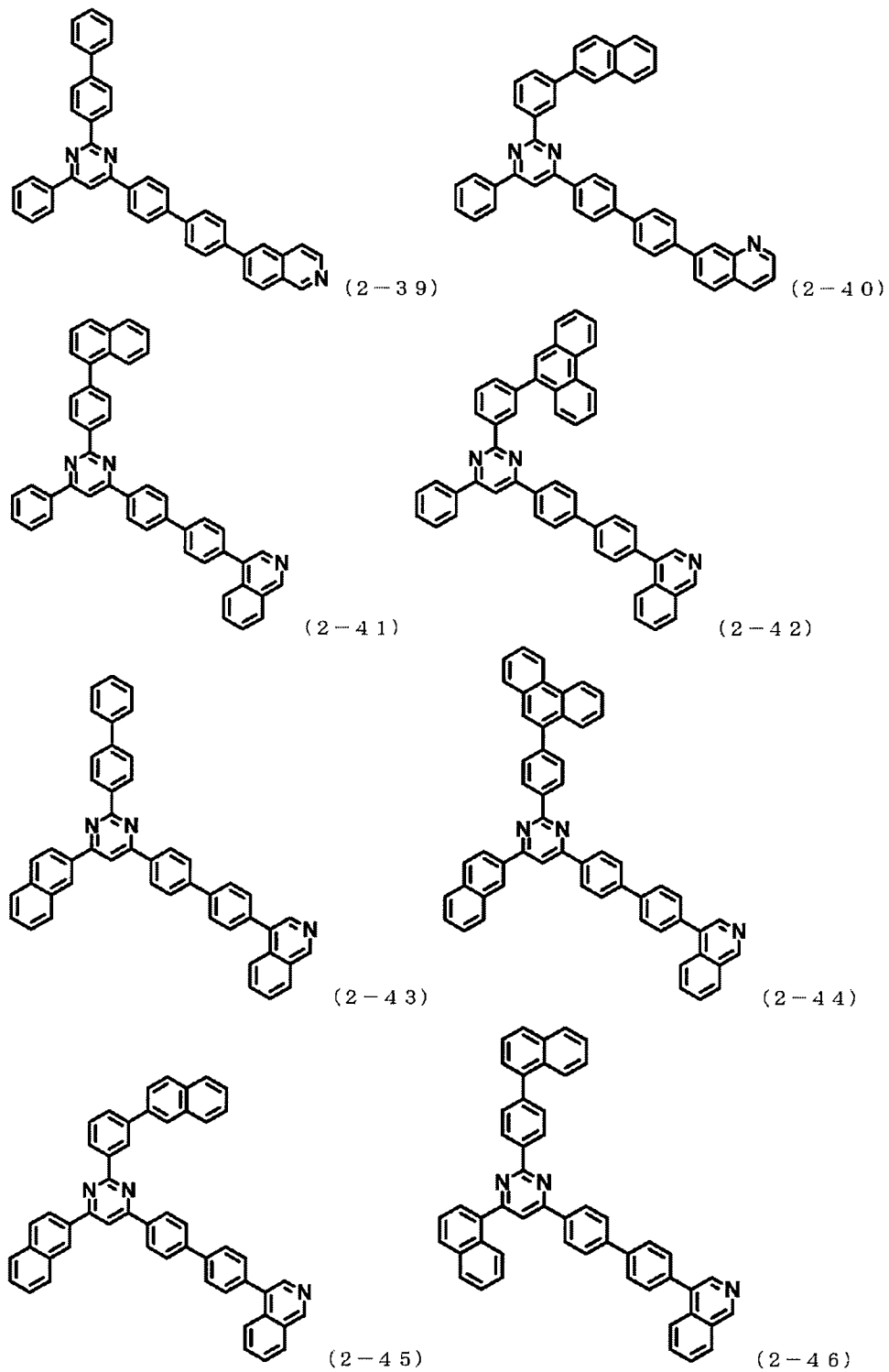
FIG. 19 is a view showing the structural formulas of Compounds 2-39 to 2-46 which are pyrimidine derivatives II.
Figure 20:
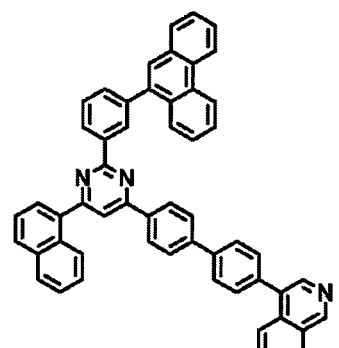
FIG. 20 is a view showing the structural formulas of Compounds 2-47 to 2-54 which are pyrimidine derivatives II.
Figure 20:
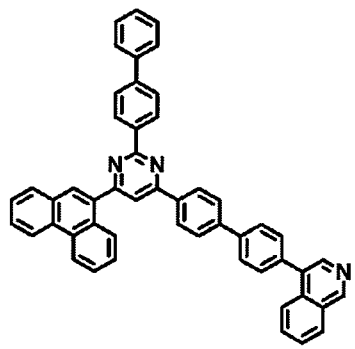
Figure 20:
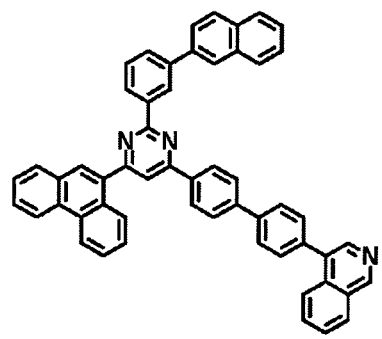
Figure 20:
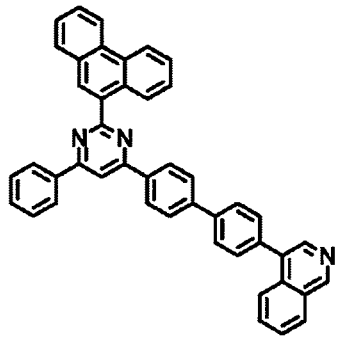
Figure 20:
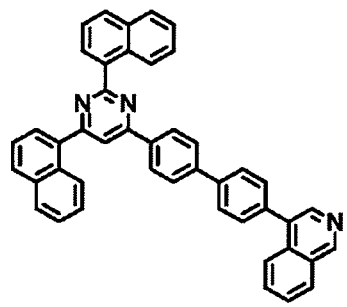
Figure 20:
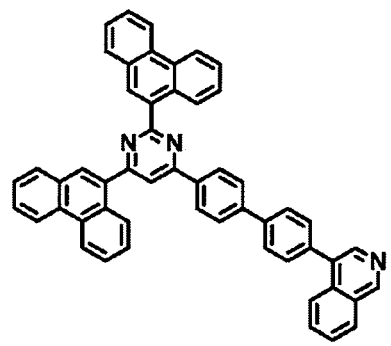
Figure 20:
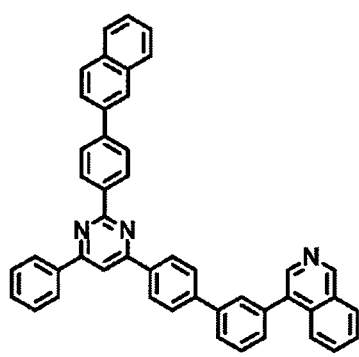
Figure 20:
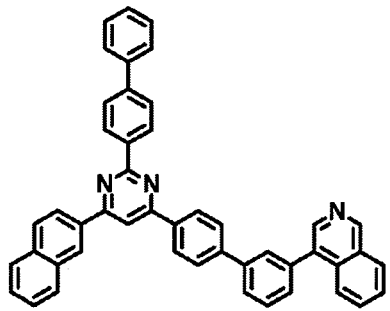
Figure 21:
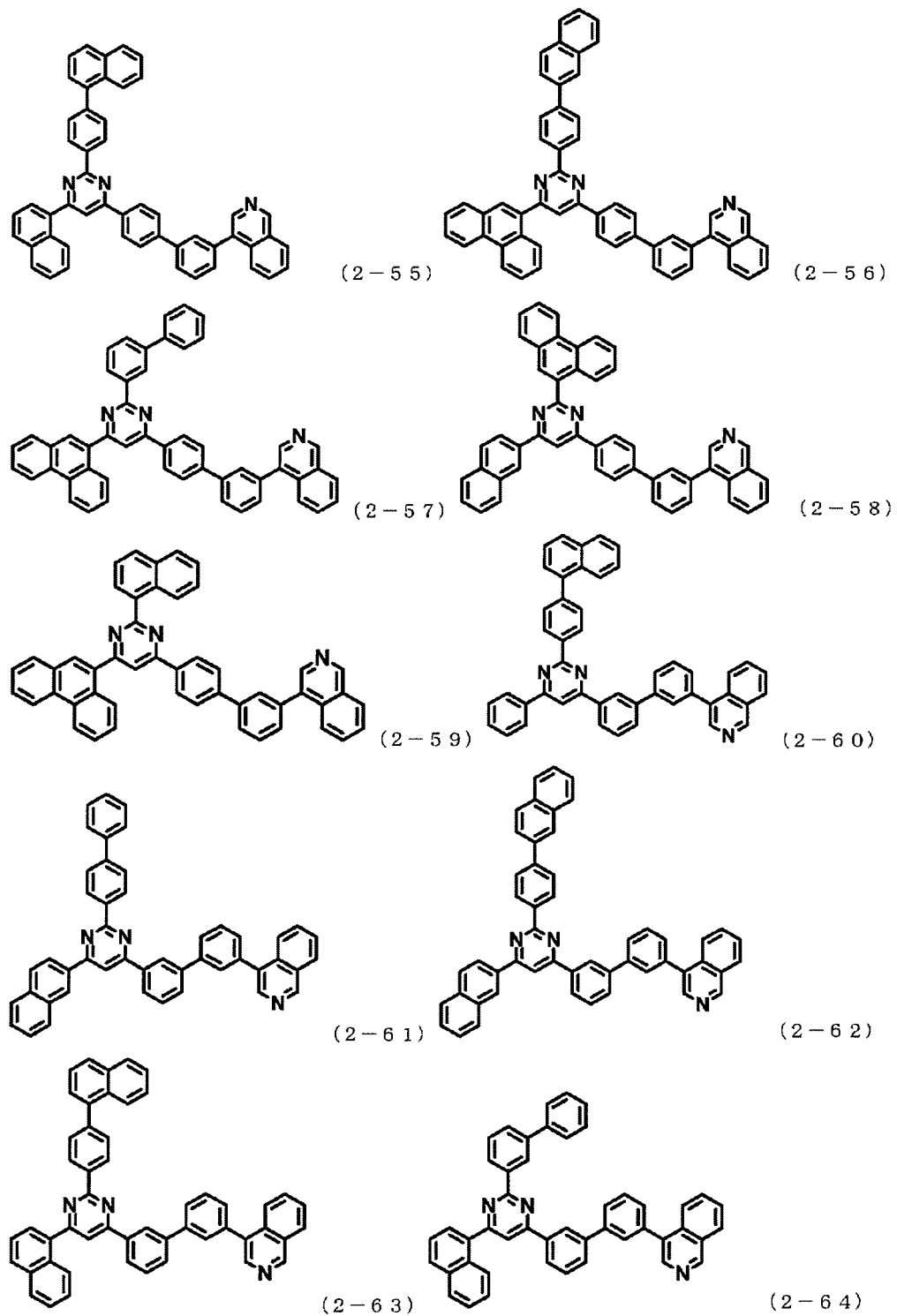
FIG. 21 is a view showing the structural formulas of Compounds 2-55 to 2-64 which are pyrimidine derivatives II.
Figure 22:
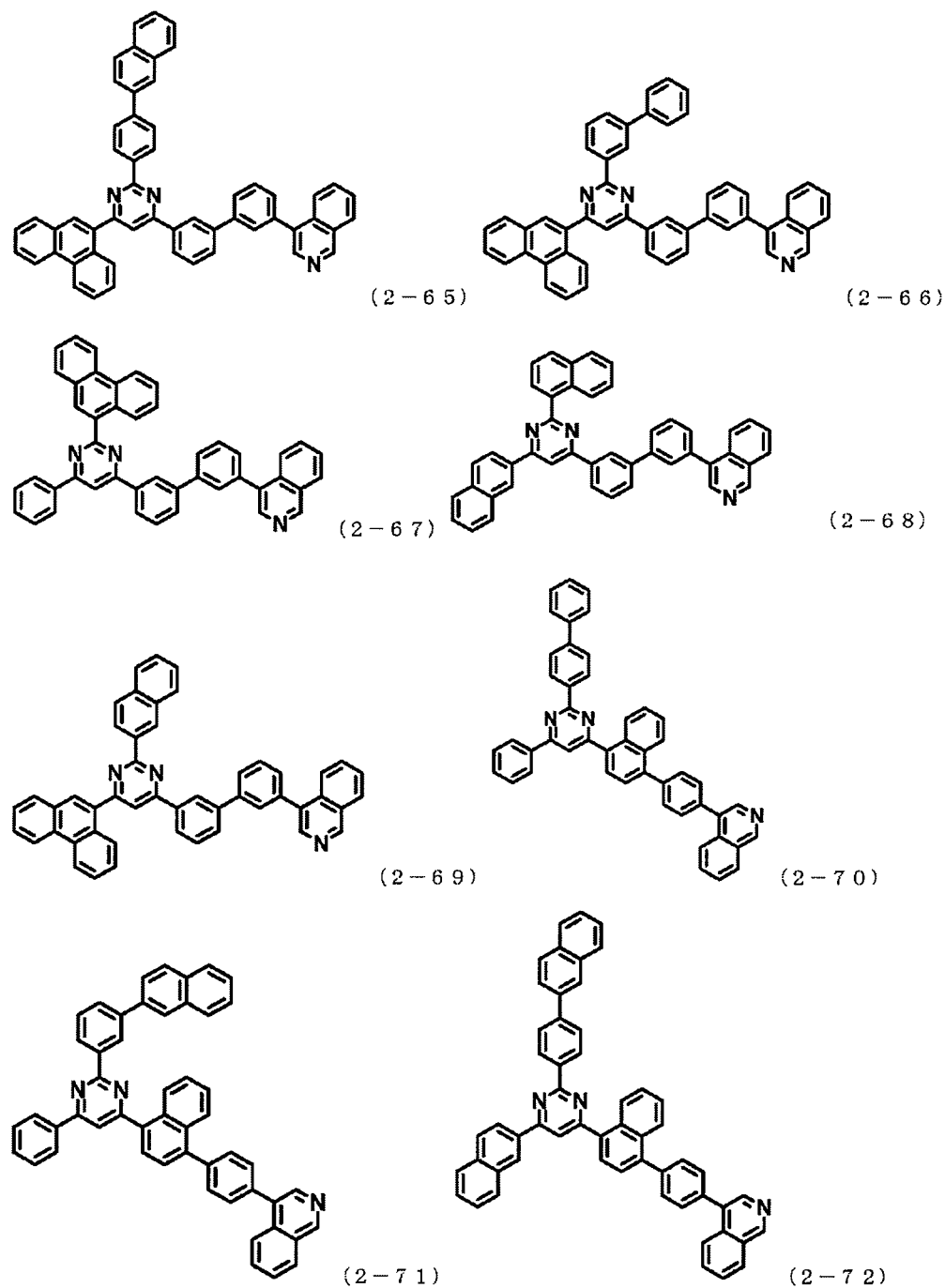
FIG. 22 is a view showing the structural formulas of Compounds 2-65 to 2-72 which are pyrimidine derivatives II.
Figure 23:
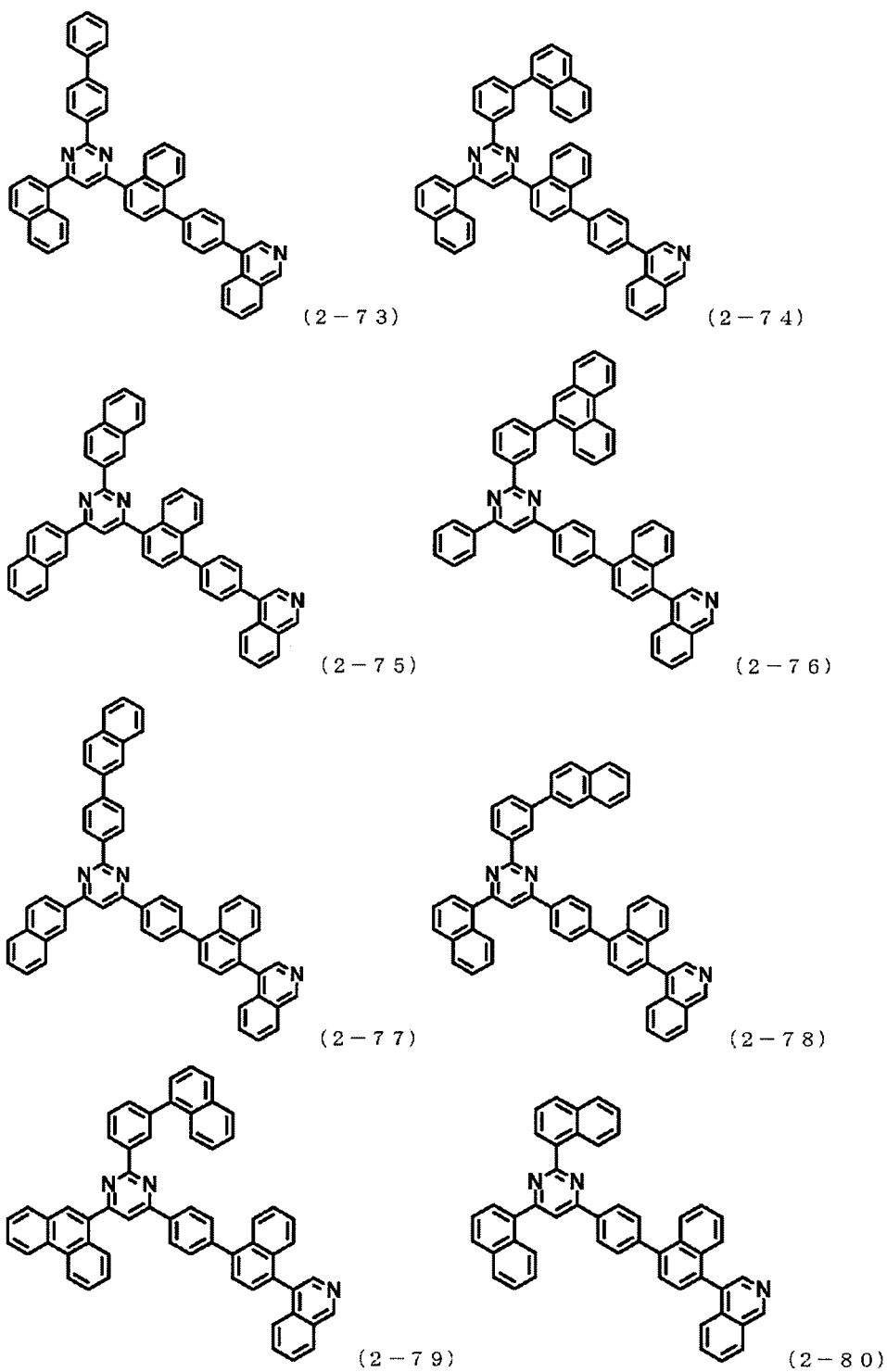
FIG. 23 is a view showing the structural formulas of Compounds 2-73 to 2-80 which are pyrimidine derivatives II.
Figure 24:
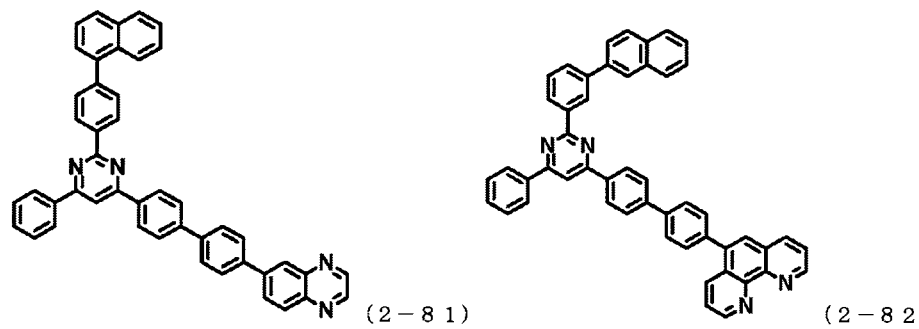
FIG. 24 is a view showing the structural formulas of Compounds 2-81 to 2-88 which are pyrimidine derivatives II.
Figure 24:
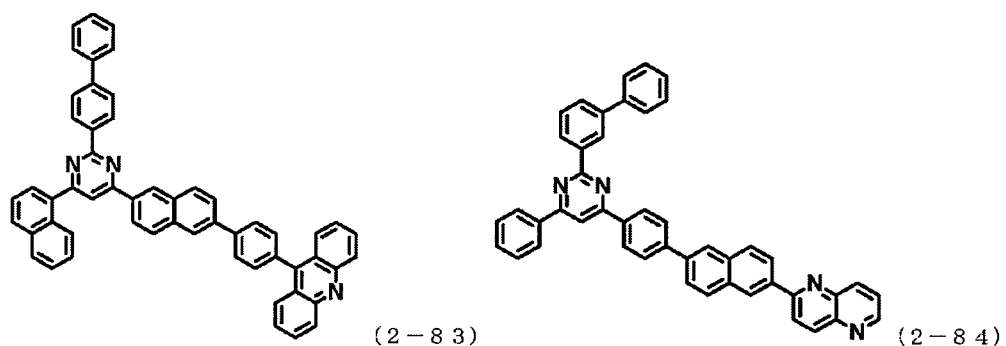
Figure 24:
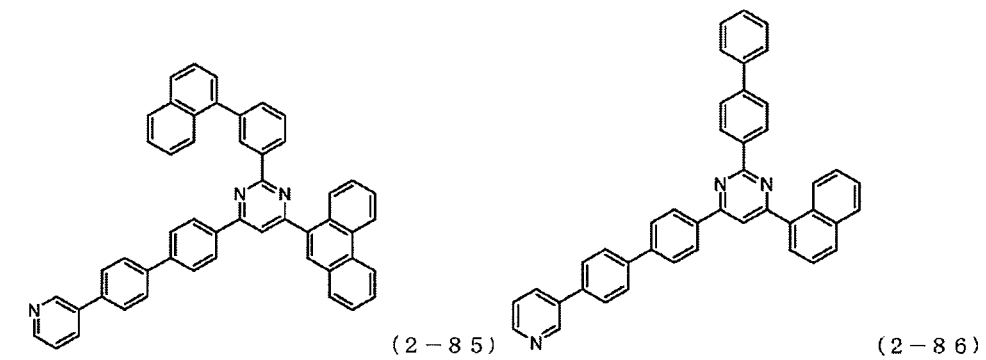
Figure 24:
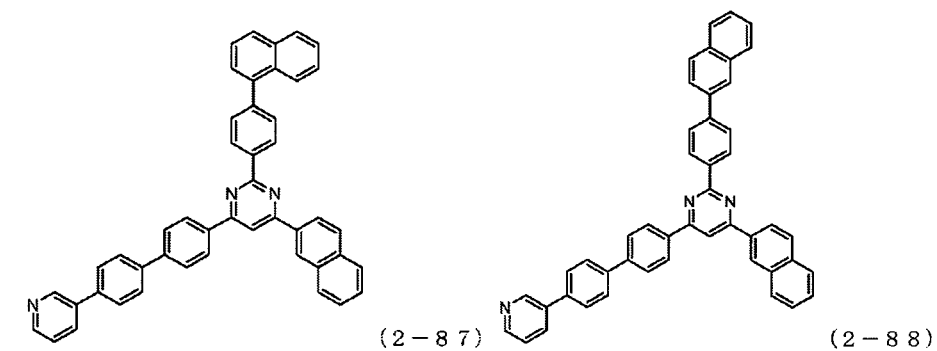
Figure 25:
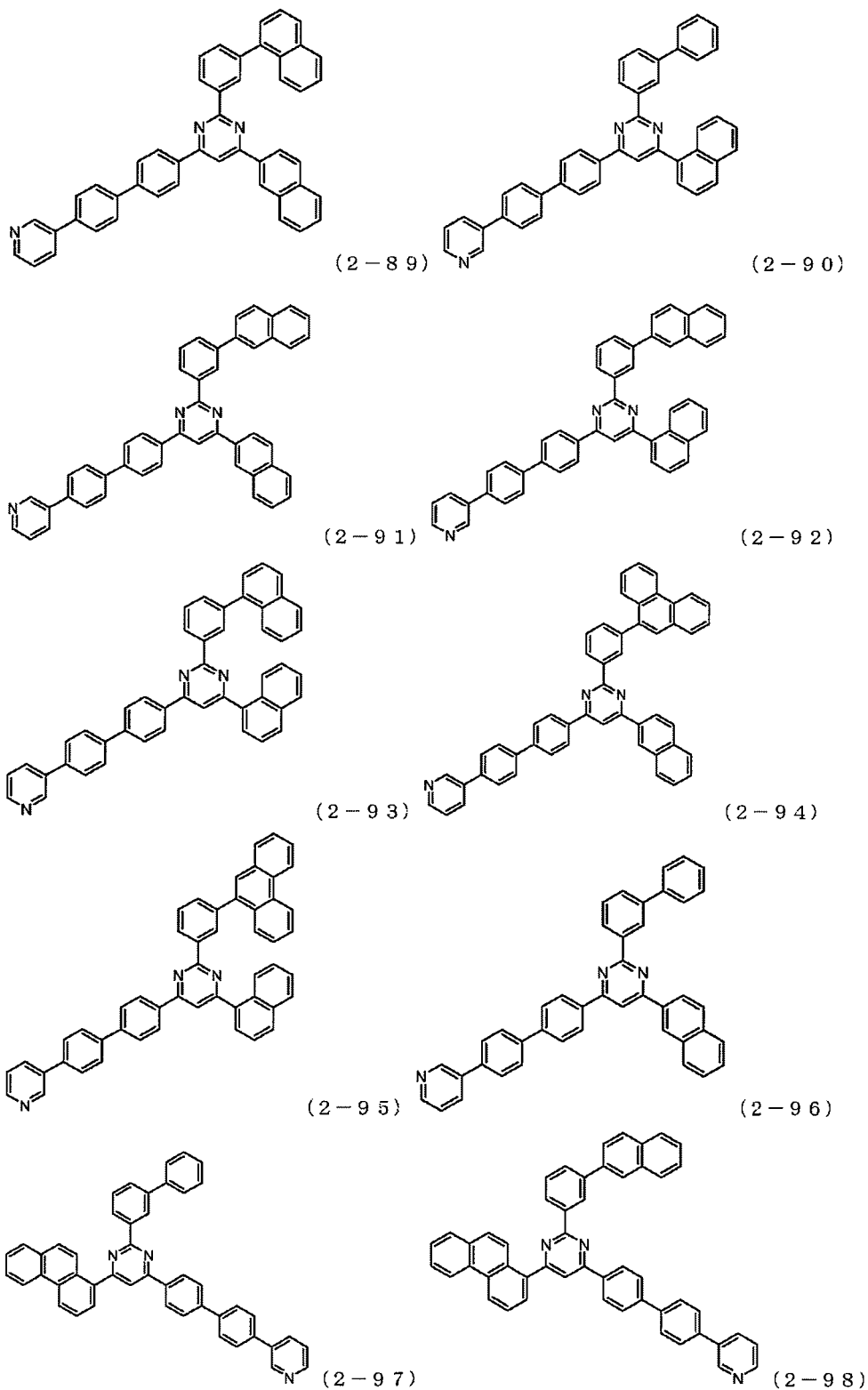
FIG. 25 is a view showing the structural formulas of Compounds 2-89 to 2-98 which are pyrimidine derivatives II.
Figure 26:
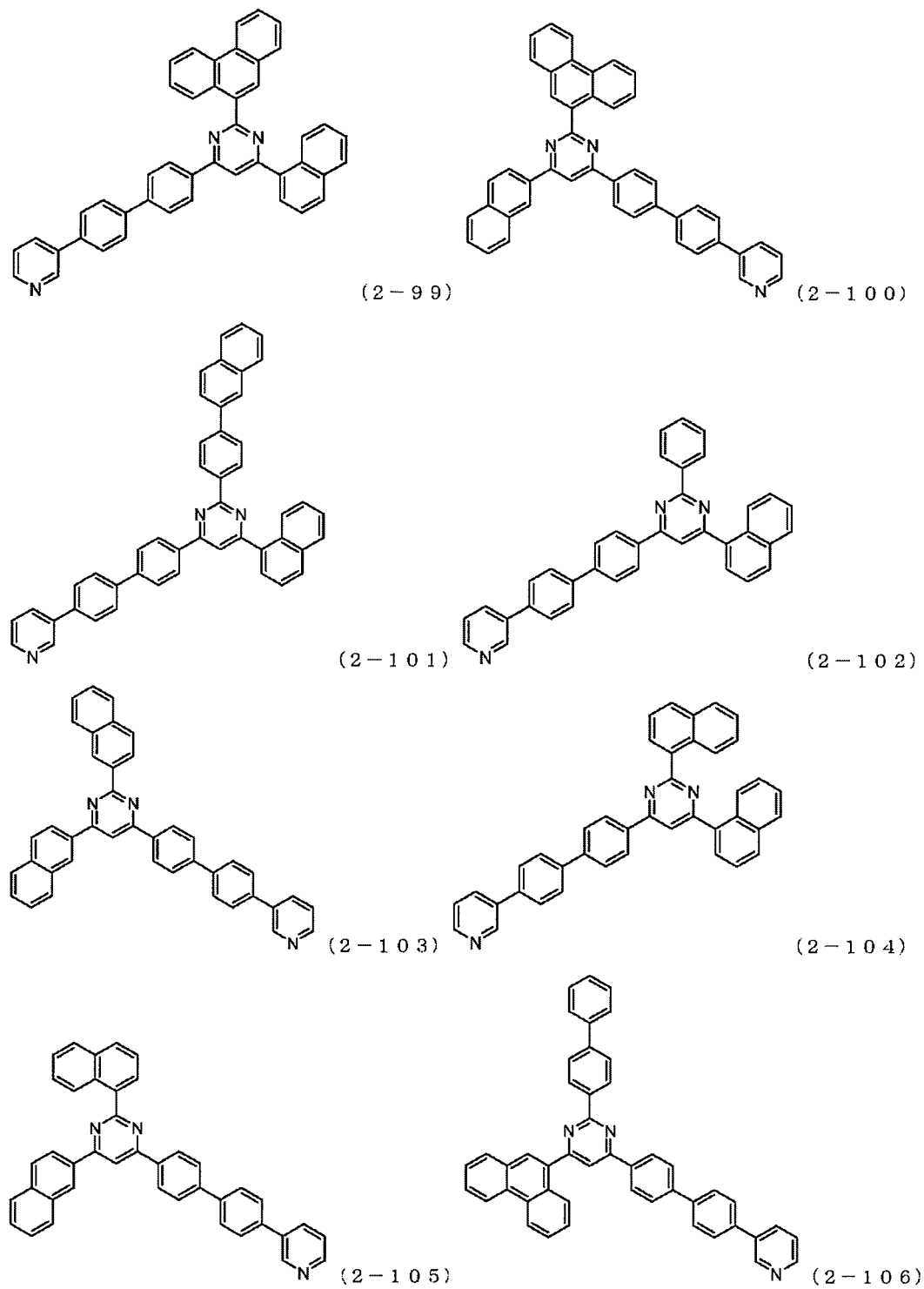
FIG. 26 is a view showing the structural formulas of Compounds 2-99 to 2-106 which are pyrimidine derivatives II.
Figure 27:
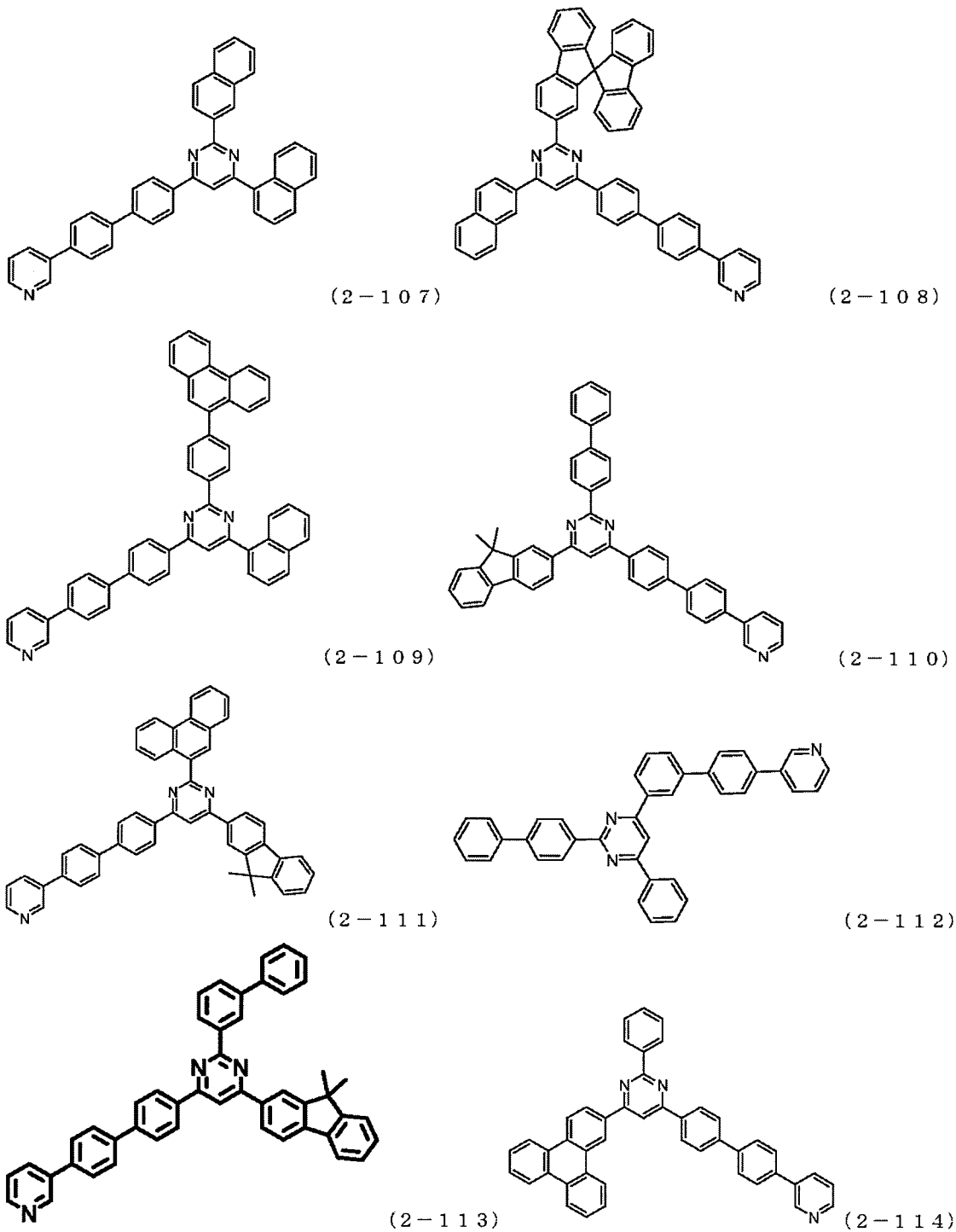
FIG. 27 is a view showing the structural formulas of Compounds 2-107 to 2-114 which are pyrimidine derivatives II.
Figure 28:
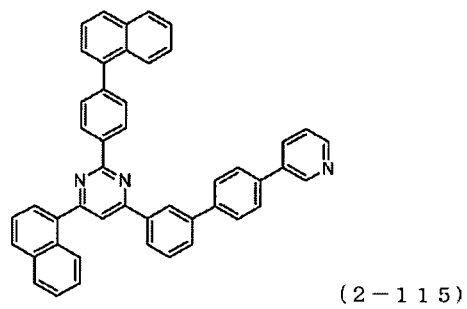
FIG. 28 is a view showing the structural formulas of Compounds 2-115 to 2-124 which are pyrimidine derivatives II.
Figure 28:
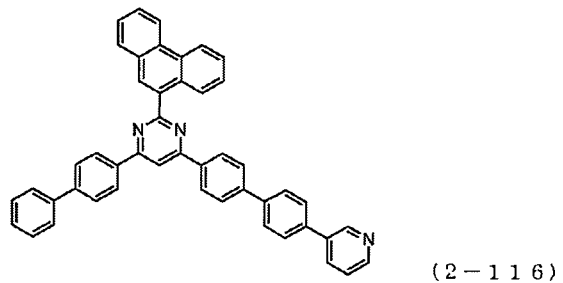
Figure 28:
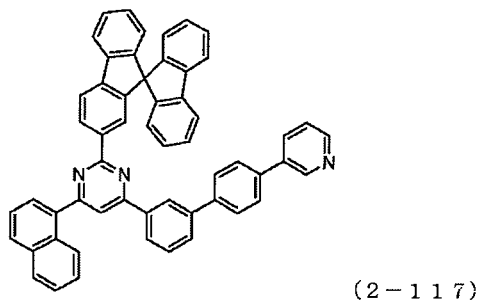
Figure 28:
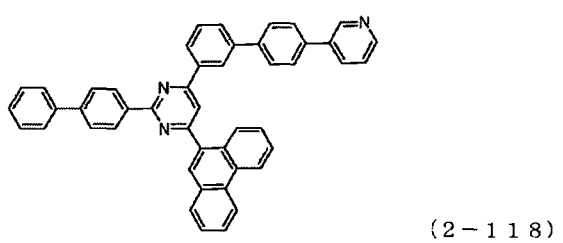
Figure 28:
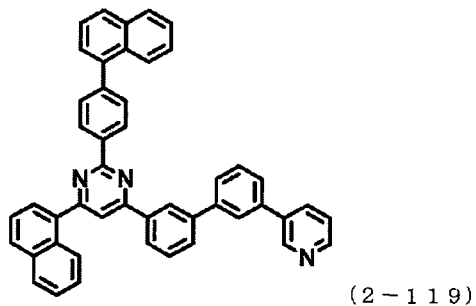
Figure 28:
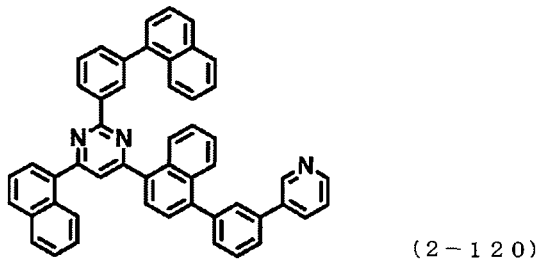
Figure 28:
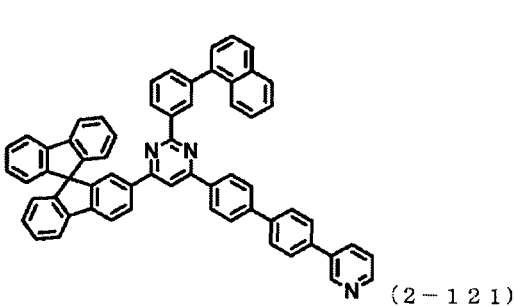
Figure 28:
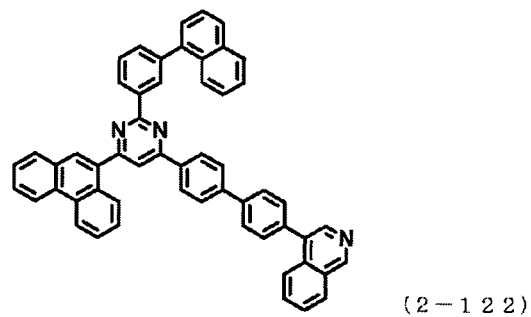
Figure 28:
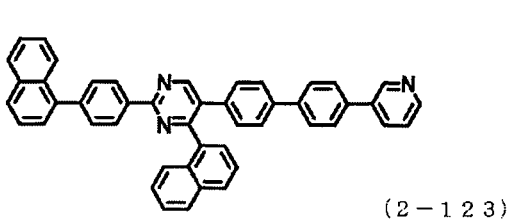
Figure 28:
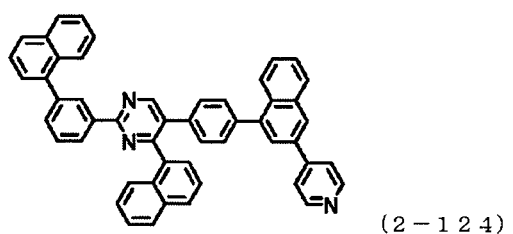
Figure 29:
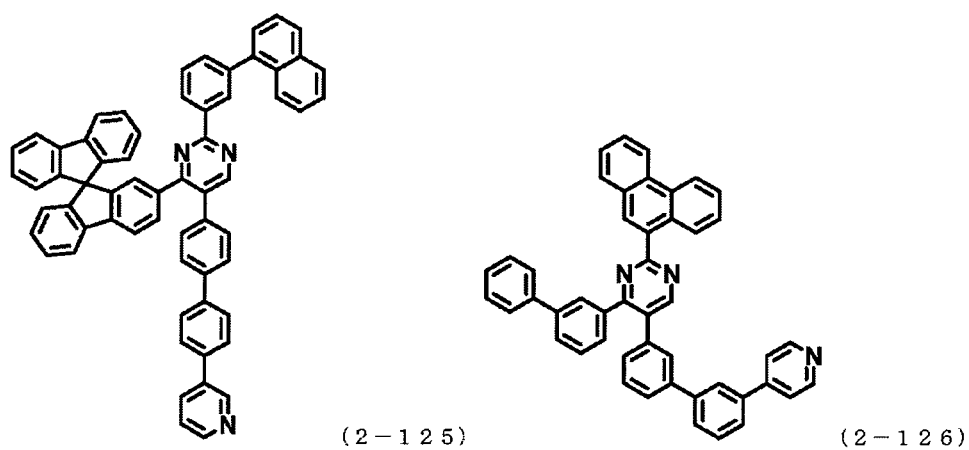
FIG. 29 is a view showing the structural formulas of Compounds 2-125 to 2-126 which are pyrimidine derivatives II.
Figure 30:
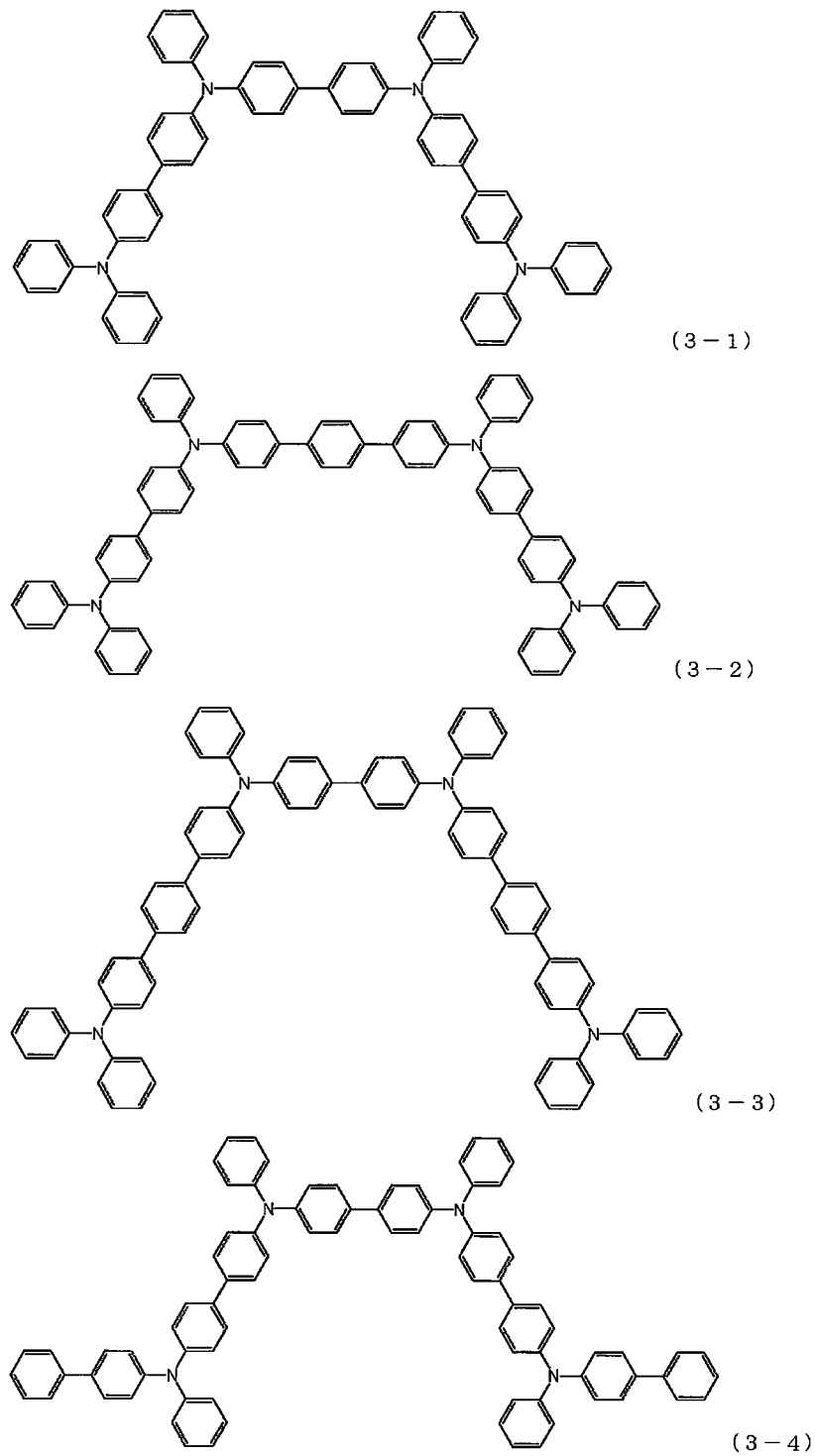
FIG. 30 is a view showing the structural formulas of Compounds 3-1 to 3-4 which are triarylamine compounds III.

As long as the organic EL device of the present invention has such a basic structure, its layer structure can take various forms. For example, it is possible to provide a hole injection layer between the anode and the first hole transport layer, provide an electron blocking layer between the second hole transport layer and the luminous layer, provide a hole blocking layer between the luminous layer and the electron transport layer, or provide an electron injection layer between the electron transport layer and the cathode. Moreover, some organic layers can be omitted, or the roles of some organic layers can be fulfilled by any other layer. For example, a layer concurrently serving as the hole injection layer and the first hole transport layer can be formed, or a layer concurrently serving as the electron injection layer and the electron transport layer can be formed. Furthermore, a configuration in which two or more organic layers having the same function are laminated can be adopted. For example, it is also possible to adopt a configuration in which two luminous layers are laminated, or a configuration in which two electron transport layers are laminated. FIG. 1 shows a layer configuration adopted in the Examples to be described later, namely, a layer configuration in which a transparent anode 2, a hole injection layer 3, a first hole transport layer 4, a second hole transport layer 5, a luminous layer 6, an electron transport layer 7, an electron injection layer 8, and a cathode 9 are formed in this order on a glass substrate 1.

As the respective layers will be described in detail later, the present invention is prominently characterized in that the second hole transport layer contains an arylamine compound represented by the general formula (1) (may hereinafter be referred to as "arylamine compound I"), and that the electron transport layer contains a pyrimidine derivative represented by the general formula (2) (may hereinafter be referred to as "pyrimidine derivative II"). The arylamine compound I and the pyrimidine derivative II will be described below.

<Arylamine Compound I>

The arylamine compound I contained in the second hole transport layer has a structure represented by the following general formula (1):

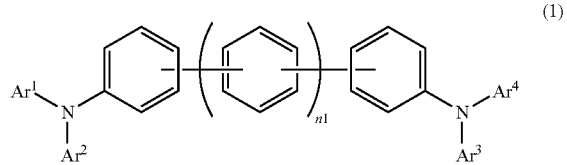

(1)

(n1)

n1 denotes an integer of 1 to 4.

($Ar^1$ to $Ar^4$)

$Ar^1$, $Ar^2$, $Ar^3$ and $Ar^4$ may be identical or different, and each represents an aromatic hydrocarbon group, an aromatic heterocyclic group, or a condensed polycyclic aromatic group. Herein, the condensed polycyclic aromatic group does not have a heteroatom (e.g., a nitrogen atom, an oxygen atom, or a sulfur atom) in its skeleton.

Examples of the aromatic hydrocarbon group, the aromatic heterocyclic group, or the condensed polycyclic aromatic group, represented by $Ar^1$ to $Ar^4$, include a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, and a carbolinyl group. $Ar^1$ to $Ar^4$ may be present independently of each other without forming a ring. However, $Ar^1$ and $Ar^2$, or $Ar^3$ and $Ar^4$ may bind to each other via a single bond, a substituted or unsubstituted methylene group, an oxygen atom, or a sulfur atom to form a ring.

Preferred as the aromatic heterocyclic group, represented by $Ar^1$ to $Ar^4$, is a sulfur-containing aromatic heterocyclic group such as a thienyl group, a benzothienyl group; a benzothiazolyl group, or a dibenzothienyl group; an oxygen-containing aromatic heterocyclic group such as a furyl group, a pyrrolyl group, a benzofuranyl group, a benzoxazolyl group, or a dibenzofuranyl group; or an N-substituted carbazolyl group. As a substituent which the N-substituted carbazolyl group has, the aromatic hydrocarbon group or condensed polycyclic aromatic group illustrated above is preferred.

The aromatic hydrocarbon group, the aromatic heterocyclic group, or the condensed polycyclic aromatic group, represented by $Ar^1$ to $Ar^4$, may be unsubstituted or may have a substituent. The substituent can be exemplified by the following groups, in addition to a deuterium atom, a cyano group, and a nitro group:

a halogen atom, for example, a fluorine atom, a chlorine atom, a bromine atom, or an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, or an n-hexyl group;

an alkyloxy group having 1 to 6 carbon atoms, for example, a methyloxy group, an ethyloxy group, or a propyloxy group;

an alkenyl group having 2 to 6 carbon atoms, for example, a vinyl group or an allyl group;

an aryloxy group, for example, a phenyloxy group or a tolyloxy group;

an arylalkyloxy group, for example, a benzyloxy group or a phenethyloxy group;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, or a triphenylenyl group;

an aromatic heterocyclic group, for example, a pyridyl group, a furyl group, a thienyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, or a carbolinyl group;

an arylvinyl group, for example, a styryl group, or a naphthylvinyl group; and an acyl group, for example, an acetyl group, or a benzoyl group;

where the alkyl group having 1 to 6 carbon atoms, the alkenyl group having 2 to 6 carbon atoms, and the alkyloxy group having 1 to 6 carbon atoms may be straight-chain or branched. Any of these substituents may be unsubstituted or may be further substituted by the above exemplary substituent. These substituents may be present independently of each other without forming a ring. However, they may bind to each other via a single bond, a substituted or unsubstituted methylene group, an oxygen atom, or a sulfur atom to form a ring.

Preferred Embodiments

Preferred embodiments of the arylamine compound I will be described below. In the description of the preferred embodiments, the groups without the designation of "substituted" or "unsubstituted" may have a substituent or may be unsubstituted.

As $Ar^1$ to $Ar^4$, an aromatic hydrocarbon group, an oxygen-containing aromatic heterocyclic group, or a condensed polycyclic aromatic group is preferred, and a phenyl group, a biphenylyl group, a terphenylyl group, a naphthyl group, a phenanthrenyl group, a triphenylenyl group, a fluorenyl group, a dibenzofuranyl group, or a fluoranthenyl group is more preferred.

It is preferred that $Ar^1$ and $Ar^2$ be different groups, or that $Ar^3$ and $Ar^4$ be different groups. It is more preferred that $Ar^1$ and $Ar^2$ be different groups, and that $Ar^3$ and $Ar^4$ be different groups.

As the substituent optionally possessed by the aromatic hydrocarbon group, aromatic heterocyclic group, or condensed polycyclic aromatic group, represented by $Ar^1$ to $Ar^4$, a deuterium atom, an alkyl group having 1 to 6 carbon atoms, an alkenyl group having 2 to 6 carbon atoms, an aryloxy group, an aromatic hydrocarbon group, a nitrogen-containing aromatic heterocyclic group, an oxygen-containing aromatic heterocyclic group, or a condensed polycyclic aromatic group is preferred, and a deuterium atom, a phenyl group, a biphenylyl group, a naphthyl group, a dibenzofuranyl group, or a vinyl group is more preferred. Formation of a condensed aromatic ring upon binding of the substituents via a single bond is also preferred.

As n1, 1 to 3 is preferred, and 1 or 2 is more preferred.

As the mode of binding of the phenylene groups in the general formula (1), a mode in which all the bonds are 1,4-bonds is not preferred, but a mode in which at least one 1,2-bond or 1,3-bond is contained is preferred, from the viewpoint of thin film stability which influences the device lifetime. For example, compounds in which phenylene groups are not linearly coupled, as shown below, are preferred as the arylamine compounds I having 3 phenylene groups (n1=1), 4 phenylene groups (n1=2), or 5 phenylene groups (n1=3) coupled together:

1,1': 2',1"-terphenyldiamine
1,1': 3',1"-terphenyldiamine
1,1': 2',1": 3",1'''-quaterphenyldiamine
1,1': 3',1": 2",1''': 3''', 1''''-quinquephenyldiamine
1,1': 3',1": 3",1''': 3''', 1''''-quinquephenyldiamine
1,1': 2',1": 2",1'''-quaterphenyldiamine
1,1': 3',1": 3",1'''-quaterphenyldiamine
1,1': 4',1": 2",1''': 4''', 1''''-quinquephenyldiamine
1,1': 2',1": 3",1''': 2''', 1''''-quinquephenyldiamine
1,1': 4',1": 3",1''': 4''', 1''''-quinquephenyldiamine
1,1': 2',1": 2",1''': 2''', 1''''-quinquephenyldiamine If the phenylene groups are all bound by 1,4-bonds, it is preferred, as in Compound 1-94, that the phenylene group be bound at the ortho-position or the meta-position with respect to $-NAr^1Ar^2$ in the benzene ring to which the $-NAr^1Ar^2$ is bound, and that the phenylene group be bound at the ortho-position or the meta-position with respect to $-NAr^3Ar^4$ in the benzene ring to which the $-NAr^3Ar^4$ is bonded.

The arylamine compound I with n1=1 preferably has the following skeleton:
4,4"-diamino-[1,1';3',1"]terphenyl skeleton;
3,3"-diamino-[1,1';3',1"]terphenyl skeleton;
2,2"-diamino-[1,1';3',1"]terphenyl skeleton;
4,4"-diamino-[1,1';2',1"]terphenyl skeleton;
3,3"-diamino-[1,1';2',1"]terphenyl skeleton;
2,2"-diamino-[1,1';2',1"]terphenyl skeleton;
2,4"-diamino-[1,1';4',1"]terphenyl skeleton;
2,2"-diamino-[1,1';4',1"]terphenyl skeleton;
3,3"-diamino-[1,1';4',1"]terphenyl skeleton.

Of the arylamine compounds I, the compounds suitably used in the organic EL device of the present invention are concretely exemplified in FIGS. 2 to 14. However, the arylamine compounds I are not limited to these compounds. D stands for deuterium.

The arylamine compound I can be produced by a publicly known method such as Suzuki coupling.

<Pyrimidine Derivative II>

The pyrimidine derivative II contained in the electron transport layer is represented by the following general formula (2):

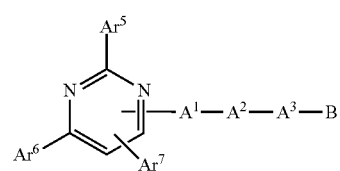

(2)

The pyrimidine derivative II is broadly classified into the following two forms in accordance with the positional relationship between -$Ar^7$ and -$A^1$-$A^2$-$A^3$-B:

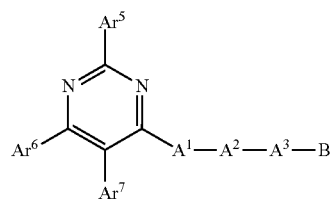

(2a)

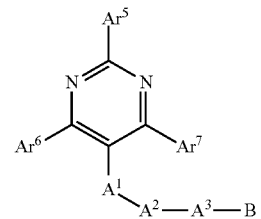

(2b)

($Ar^5$ to $Ar^7$)

$Ar^5$ and $Ar^6$ may be identical or different, and each represents an aromatic hydrocarbon group, an aromatic heterocyclic group, or a condensed polycyclic aromatic group. $Ar^7$ represents a hydrogen atom, an aromatic hydrocarbon group, an aromatic heterocyclic group, or a condensed polycyclic aromatic group. $Ar^5$ and $Ar^7$ may be identical or different, and $Ar^6$ and $Ar^7$ may be identical or different.

Examples of the aromatic hydrocarbon group, the aromatic heterocyclic group, or the condensed polycyclic aromatic group, represented by $Ar^5$ to $Ar^7$, include a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, a spirobifluorenyl group, a furyl group, a thienyl group, a benzofuranyl group, a benzothienyl group, a dibenzofuranyl group, and a dibenzothienyl group.

The aromatic hydrocarbon group, the aromatic heterocyclic group, or the condensed polycyclic aromatic group, represented by $Ar^5$ to $Ar^7$, may be unsubstituted or may have a substituent. The substituent can be exemplified by the following groups, in addition to a deuterium atom, a cyano group, and a nitro group:

a halogen atom, for example, a fluorine atom, a chlorine atom, a bromine atom, or an iodine atom;

an alkyl group having 1 to 6 carbon atoms, for example, a methyl group, an ethyl group, an n-propyl group, an isopropyl group, an n-butyl group, an isobutyl group, a tert-butyl group, an n-pentyl group, an isopentyl group, a neopentyl group, or an n-hexyl group;

an alkyloxy group having 1 to 6 carbon atoms, for example, a methyloxy group, an ethyloxy group, or a propyloxy group;

an alkenyl group, for example, a vinyl group or an allyl group;

an aryloxy group, for example, a phenyloxy group or a tolyloxy group;

an arylalkyloxy group, for example, a benzyloxy group or a phenethyloxy group;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a spirobifluorenyl group, or an acenaphthenyl group;

an aromatic heterocyclic group, for example, a pyridyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a carbolinyl group, an azaspirobifluorenyl group, or a diazaspirobifluorenyl group;

an arylvinyl group, for example, a styryl group, or a naphthylvinyl group; and an acyl group, for example, an acetyl group, or a benzoyl group.

The alkyl group having 1 to 6 carbon atoms, the alkenyl group, and the alkyloxy group having 1 to 6 carbon atoms may be a straight-chain or branched. Any of these substituents may be unsubstituted or may be further substituted by the above exemplary substituent. Furthermore, these substituents may be present independently of each other so as not to form a ring. However, they may bind to each other via a single bond, a substituted or unsubstituted methylene group, an oxygen atom, or a sulfur atom to form a ring. Any of these substituents, and $Ar^5$, $Ar^6$ or $Ar^7$ to which the substituent is bound may bind to each other via an oxygen atom or a sulfur atom to form a ring.

($A^1$ to $A^3$)

$A^1$ and $A^2$ may be identical or different, and each represents a divalent group of an aromatic hydrocarbon, or a divalent group of a condensed polycyclic aromatic. $A^3$ represents a divalent group of an aromatic hydrocarbon, a divalent group of a condensed polycyclic aromatic, or a single bond.

The divalent group of an aromatic hydrocarbon, or the divalent group of a condensed polycyclic aromatic represents a divalent group formed by removing two hydrogen atoms from an aromatic hydrocarbon or a condensed polycyclic aromatic. Examples of the aromatic hydrocarbon or the condensed polycyclic aromatic include benzene, biphenyl, terphenyl, tetrakisphenyl, styrene, naphthalene, anthracene, acenaphthalene, fluorene, phenanthrene, indane, pyrene, triphenylene, and spirobifluorene.

The divalent group of an aromatic hydrocarbon, or the divalent group of a condensed polycyclic aromatic, represented by $Ar^1$ to $Ar^3$, may be unsubstituted or may have a substituent. Examples of the substituent are the same as those shown as the substituents that may be possessed by the aromatic hydrocarbon group, the aromatic heterocyclic group, or the condensed polycyclic aromatic group represented by $Ar^5$ to $Ar^7$ above. The same holds true of the embodiments that the substituents can adopt.

(B)

B represents an aromatic heterocyclic group. Examples of the aromatic heterocyclic group represented by B include a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a naphthyridinyl group, a phenanthrolinyl group, an acridinyl group, a carbolinyl group, an azaspirobifluorenyl group, a diazaspirobifluorenyl group, a bipyridyl group, a terpyridyl group, a pyrazinyl group, an imidazolyl group, a quinazolinyl group, a benzotriazolyl group, a benzothiadiazolyl group, a pyridopyrrolyl group, a pyridoimidazolyl group, a pyridotriazolyl group, a phenazinyl group, a phenoxazinyl group, and a phenothiazinyl group.

The aromatic heterocyclic group, represented by B, may be unsubstituted or may have a substituent. Examples of the substituent are the same as those shown as the substituents that may be possessed by the aromatic hydrocarbon group, the aromatic heterocyclic group, or the condensed polycyclic aromatic group represented by $Ar^5$ to $Ar^7$. The same holds true of the embodiments that the substituent can adopt.

Preferred Embodiments

Preferred embodiments of the pyrimidine derivative II will be described below. In the description of the preferred embodiments, the groups without the designation of "substituted" or "unsubstituted" may have a substituent or may be unsubstituted.

As $Ar^5$, preferred is a phenyl group; a biphenylyl group; a naphthyl group; an anthracenyl group; an acenaphthenyl group; a phenanthrenyl group; a fluorenyl group; an indenyl group; a pyrenyl group; a perylenyl group; a fluoranthenyl group; a triphenylenyl group; a spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group. More preferred is a phenyl group, a biphenylyl group, a naphthyl group, a phenanthrenyl group, a fluorenyl group, a pyrenyl group, a fluoranthenyl group, a triphenylenyl group, a spirobifluorenyl group, a dibenzofuranyl group, or a dibenzothienyl group.

If $Ar^5$ is a phenyl group, such a phenyl group preferably has, as a substituent, a condensed polycyclic aromatic group or an unsubstituted phenyl group, and more preferably has, as a substituent, a naphthyl group, a phenanthrenyl group, a pyrenyl group, a fluoranthenyl group, a triphenylenyl group, a spirobifluorenyl group, or an unsubstituted phenyl group. It is also preferred for the substituent and the phenyl group to bind to each other via an oxygen atom or a sulfur atom, thereby forming a ring.

As $Ar^6$, a phenyl group having a substituent is preferred. As the substituent that the phenyl group has, preferred is an aromatic hydrocarbon group, for example, a phenyl group, a biphenylyl group, or a terphenyl group; a condensed polycyclic aromatic group, for example, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, or a spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group. More preferred is a phenyl group, a naphthyl group, an anthracenyl group, a phenanthrenyl group, a fluorenyl group, a pyrenyl group, a fluoranthenyl group, a triphenylenyl group, a spirobifluorenyl group, a dibenzofuranyl group, or a dibenzothienyl group. It is also preferred for the substituent and the phenyl group to bind to each other via an oxygen atom or a sulfur atom, thereby forming a ring.

Alternatively, a preferred example of $Ar^6$ is a spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group.

As $Ar^7$, preferred is a hydrogen atom; a spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group; or a phenyl group having a substituent, and a hydrogen atom is more preferred. As the substituent that the phenyl group has, preferred is an aromatic hydrocarbon group, for example, a phenyl group, a biphenylyl group, or a terphenyl group; a condensed polycyclic aromatic group, for example, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, or a spirobifluorenyl group; an oxygen-containing aromatic heterocyclic group, for example, a furyl group, a benzofuranyl group, or a dibenzofuranyl group; or a sulfur-containing aromatic heterocyclic group, for example, a thienyl group, a benzothienyl group, or a dibenzothienyl group. More preferred is a phenyl group, a naphthyl group, an anthracenyl group, a phenanthrenyl group, a fluorenyl group, a pyrenyl group, a fluoranthenyl group, a triphenylenyl group, a spirobifluorenyl group, a dibenzofuranyl group, or a dibenzothienyl group. It is also preferred for the substituent and the phenyl group to bind to each other via an oxygen atom or a sulfur atom, thereby forming a ring.

From the viewpoint of thin film stability, it is preferred that $Ar^5$ and $Ar^6$ be different groups. Since good symmetry of the entire molecule may facilitate crystallization, it is preferred, from the viewpoint of thin film stability, that $Ar^6$ and $Ar^7$ be different groups. Cases where "$Ar^5$ and $Ar^6$ are different groups" and cases where "$Ar^6$ and $Ar^7$ are different groups" include an embodiment in which the positions of binding to the pyrimidine ring are different, an embodiment in which different substituents are present, and an embodiment in which the positions of binding of the substituents are different.

As $A^1$ and $A^2$, a divalent group formed by removing two hydrogen atoms from benzene, biphenyl, naphthalene, anthracene, fluorene, or phenanthrene is preferred, and a divalent group formed by removing two hydrogen atoms from benzene or naphthalene is more preferred.

Preferred is an embodiment in which one of $A^1$ and $A^2$ is a divalent group formed by removing two hydrogen atoms from benzene (namely, a phenylene group), and the other is a divalent group formed by removing two hydrogen atoms from naphthalene (namely, a naphthylene group), or an embodiment in which both of $A^1$ and $A^2$ are phenylene groups. In such an embodiment, the sublimation temperature does not become too high when an organic EL device is produced by the vacuum deposition method.

As $A^3$, a phenylene group or a single bond is preferred, and a single bond is more preferred, because the sublimation temperature does not become too high when an organic EL device is produced by vacuum deposition.

As B, a nitrogen-containing aromatic heterocyclic group, for example, a triazinyl group, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzimidazolyl group, a pyrazolyl group, an azafluorenyl group, a diazafluorenyl group, a naphthyridinyl group, a phenanthrolinyl group, an acridinyl group, a carbolinyl group, an azaspirobifluorenyl group, or a diazaspirobifluorenyl group is preferred; a triazinyl group, a pyridyl group, a pyrimidinyl group, a quinolyl group, an isoquinolyl group, an indolyl group, a quinoxalinyl group, an azafluorenyl group, a diazafluorenyl group, a benzimidazolyl group, a naphthyridinyl group, a phenanthrolinyl group, an acridinyl group, an azaspirobifluorenyl group, or a diazaspirobifluorenyl group is more preferred; and a pyridyl group, a pyrimidinyl group, a quinolyl group, an isoquinolyl group, an indolyl group, an azafluorenyl group, a diazafluorenyl group, a quinoxalinyl group, a benzimidazolyl group, a naphthyridinyl group, a phenanthrolinyl group, an acridinyl group, an azaspirobifluorenyl group, or a diazaspirobifluorenyl group is particularly preferred.

Particularly preferred embodiments of the respective groups are as follows:

1) $Ar^5$ and $Ar^6$ each represents an aromatic hydrocarbon group or a condensed polycyclic aromatic group, and $Ar^7$ represents a hydrogen atom, an aromatic hydrocarbon group, or a condensed polycyclic aromatic group.

2) $Ar^5$ is a phenyl group having a substituent.

3) $Ar^5$ is a phenyl group having a substituent, and the substituent is a condensed polycyclic aromatic group.

4) $Ar^5$ is a phenyl group having a substituent, and the substituent is an unsubstituted condensed polycyclic aromatic group.

5) $Ar^5$ is a condensed polycyclic aromatic group.

6) $Ar^5$ is an unsubstituted condensed polycyclic aromatic group.

7) $Ar^6$ is an unsubstituted phenyl group.

8) $Ar^6$ is a phenyl group having a substituent, and the substituent is an aromatic hydrocarbon group or a condensed polycyclic aromatic group.

9) $Ar^6$ is a phenyl group having a substituent, and the substituent is an aromatic hydrocarbon group.

10) $Ar^6$ is a phenyl group having a substituent, and the substituent is a condensed polycyclic aromatic group.

11) $Ar^6$ is a condensed polycyclic aromatic group.

12) $Ar^6$ is a naphthyl group.

13) $Ar^6$ is a phenanthrenyl group.

14) One of $A^1$ and $A^2$ is a phenylene group.

Preferred examples of the pyrimidine derivative II are shown in FIGS. 15 to 29, but the pyrimidine derivative II is not limited to these compounds. In the concrete examples, Compounds 2-1 to 2-122 correspond to the aforementioned general formula (2a). Compounds 2-123 to 2-126 correspond to the aforementioned general formula (2b).

The pyrimidine derivative II can be synthesized in accordance with a publicly known method (see Patent Document 6).

The purification of the arylamine compound I and the pyrimidine derivative II can be performed, for example, by purification using a column chromatograph, adsorption purification using silica gel, activated carbon, activated clay, or the like, or recrystallization or crystallization using a solvent. Purification by sublimation purification or the like may be performed in the final stage. The identification of the compounds can be made by NMR analysis. As the physical properties, the glass transition point (Tg) and the work function can be measured.

The glass transition point (Tg) serves as an index to stability in a thin film state. The glass transition point (Tg) can be measured using a powder and a high sensitivity differential scanning calorimeter (DSC3100S, produced by Bruker AXS).

The work function serves as an index to hole transport properties. The work function can be measured by preparing a 100 nm thin film on an ITO substrate, and making a measurement using an ionization potential measuring device (PYS-202, produced by Sumitomo Heavy Industries, Ltd.).

Compounds for use in the organic EL device of the present invention, which are other than the arylamine compound I and the pyrimidine derivative II, (concretely, triarylamine compounds III, IV to be described later), can also be purified and subjected to various measurements by similar methods after their synthesis.

In the organic EL device of the present invention, the respective layers can take various forms, as long as they fulfill the conditions that the arylamine compound I is contained in the second hole transport layer and that the pyrimidine derivative II is contained in the electron transport layer. The respective layers will be described in detail below by reference to FIG. 1.

<Anode 2>

In the organic EL device of the present invention, the anode 2 is provided on the transparent substrate 1. An electrode material having a high work function, such as ITO or gold, is used as the anode 2.

<Hole Injection Layer 3>

The hole injection layer 3 may be provided, if necessary, between the anode 2 and the hole transport layer 4. For the hole injection layer 3, a publicly known material may be used. The aforementioned arylamine compound I, a triarylamine compound III represented by a general formula (3) described later, or a triarylamine compound IV represented by a general formula (4) described later may be used, because their hole mobility is high. If the triarylamine compound III or IV is used in the hole injection layer 3, the composition of the hole injection layer 3 and the composition of the first hole transport layer 4 to be described later have to be different.

Examples of usable and publicly known materials are materials such as starburst triphenylamine derivatives and various triphenylamine tetramers; porphyrin compounds typified by copper phthalocyanine; acceptor type heterocyclic compounds such as hexacyanoazatriphenylene; and coating type polymeric materials.

These materials may each be subjected to film formation, or any of them may be mixed with other of them and the resulting mixture may be subjected to film formation. Moreover, the materials for general use in the hole injection layer may be further p-doped with tris(bromophenyl) aminium hexachloroantimonate or radialene derivatives (see WO2014/009310), and may be used in the hole injection layer. Polymeric compounds containing the structures of benzidine derivatives such as TPD in their partial structures may also be used in the hole injection layer.

When thin film formation is performed by a publicly known method such as vapor deposition, spin coating or ink jetting with the use of any of the above materials, the hole injection layer 3 can be obtained. Each of the layers described below can similarly be obtained by thin film formation performed using a publicly known method such as vapor deposition, spin coating, or ink jetting.

<First Hole Transport Layer 4>

The first hole transport layer 4 is provided between the above anode 2 (or hole injection layer 3) and the second hole transport layer 5. In the present invention, a publicly known material as exemplified below can be incorporated into the first hole transport layer 4.

benzidine derivatives, for example,
N,N'-diphenyl N'-di(m-tolyl)benzidine (TPD),
N,N'-diphenyl N'-di(α-naphthyl)benzidine (NPD),
and
N,N,N',N'-tetrabiphenylylbenzidine;
1,1-bis[4-(di-4-tolylamino)phenyl]cyclohexane (TAPC);
and
hole transporting triarylamine compounds, for example,
triarylamine compounds having 3 to 6 triarylamine structures in the molecule, the triarylamine structures being linked together by a heteroatom-free divalent group or a single bond, and
triarylamine compounds having 2 triarylamine structures in the molecule, the triarylamine structures being linked together by a heteroatom-free divalent group or a single bond.

Of the above-mentioned publicly known materials, the triarylamine compounds having 3 to 6 triarylamine structures in the molecule, the triarylamine structures being linked together by a heteroatom-free divalent group or a single bond (may hereinafter be referred to simply as triarylamine compounds having 3 to 6 triarylamine structures); and the triarylamine compounds having 2 triarylamine structures in the molecule, the triarylamine structures being linked together by a heteroatom-free divalent group or a single bond (may hereinafter be referred to simply as triarylamine compounds having 2 triarylamine structures) are used preferably.

Figure 38:
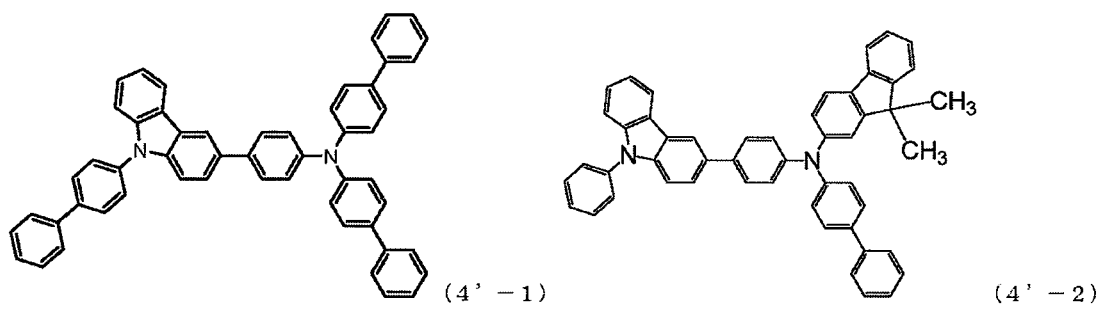
FIG. 38 is a view showing the structural formulas of triarylamine compounds having 2 triarylamine structures which are other than triarylamine compounds IV.

The triarylamine compounds having 2 triarylamine structures include an embodiment in which the two benzene rings in the triarylamine structure are linked via a single bond, namely, an embodiment having a carbazole ring structure, as in 4'-1 and 4'-2 of FIG. 38.

As the triarylamine compounds having 3 to 6 triarylamine structures, triarylamine compounds III having 4 triarylamine structures, represented by the general formula (3) described below, are preferred. The reason is that they are excellent in thin film stability and heat resistance in addition to hole transport properties, and they are can be synthesized easily.

As the triarylamine compounds having 2 triarylamine structures, triarylamine compounds IV represented by the general formula (4) described below are preferred, because they are excellent in thin film stability and heat resistance in addition to hole transport properties, and they can be synthesized easily.

Triarylamine Compound III Represented by the Following General Formula (3):

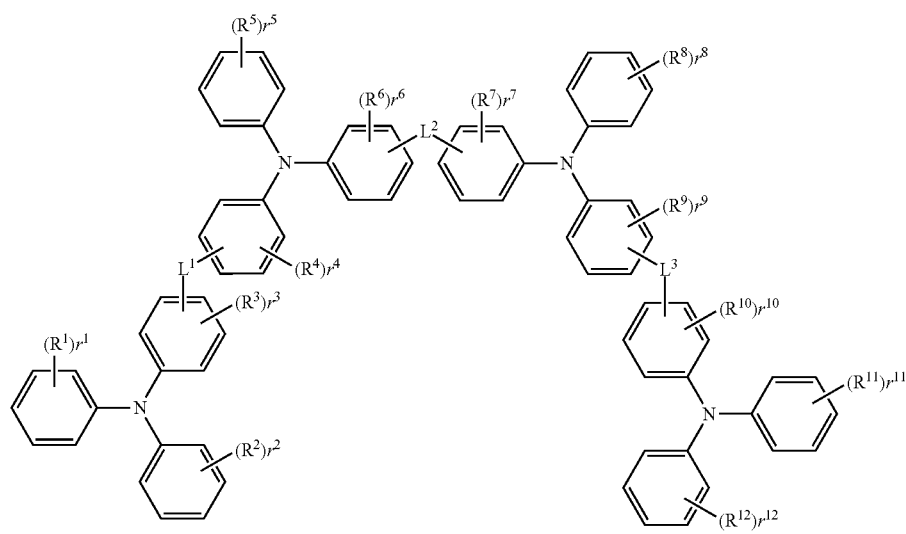

(3)

($R^1$ to $R^{12}$)

$R^1$ to $R^{12}$ may be identical or different, and each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxyl group. The alkyl group having 1 to 6 carbon atoms, the alkenyl group having 2 to 6 carbon atoms, and the alkyloxy group having 1 to 6 carbon atoms may be a straight-chain or branched.

The alkyl group having 1 to 6 carbon atoms, the cycloalkyl group having 5 to 10 carbon atoms, or the alkenyl group having 2 to 6 carbon atoms, represented by $R^1$ to $R^{12}$, can be exemplified by a methyl group, an ethyl group, an n-propyl group, an isopropyl group, an n-butyl group, an isobutyl group, a tert-butyl group, an n-pentyl group, an isopentyl group, a neopentyl group, an n-hexyl group, a cyclopentyl group, a cyclohexyl group, a 1-adamantyl group, a 2-adamantyl group, a vinyl group, an allyl group, an isopropenyl group, or a 2-butenyl group.

The alkyl group having 1 to 6 carbon atoms, the cycloalkyl group having 5 to 10 carbon atoms, or the alkenyl group having 2 to 6 carbon atoms, represented by $R^1$ to $R^{12}$, may be unsubstituted or may have a substituent. The substituent can be exemplified by the following groups, in addition to a deuterium atom, a cyano group, and a nitro group:

a halogen atom, for example, a fluorine atom, a chlorine atom, a bromine atom, or an iodine atom;

an alkyloxy group having 1 to 6 carbon atoms, for example, a methyloxy group, an ethyloxy group, or a propyloxy group;

an alkenyl group, for example, a vinyl group or an allyl group;

an aryloxy group, for example, a phenyloxy group or a tolyloxy group;

an arylalkyloxy group, for example, a benzyloxy group or a phenethyloxy group;

an aromatic hydrocarbon group or a condensed polycyclic aromatic group, for example, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, or a triphenylenyl group; and an aromatic heterocyclic group, for example, a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, or a carbolinyl group.

The alkenyl group and the alkyloxy group having 1 to 6 carbon atoms may be a straight-chain or branched. Any of these substituents may be unsubstituted or may be further substituted by the above exemplary substituent. Moreover, these substituents may be present independently of each other without forming a ring. However, they may bind to each other via a single bond, a substituted or unsubstituted methylene group, an oxygen atom, or a sulfur atom to form a ring.

The alkyloxy group having 1 to 6 carbon atoms or the cycloalkyloxy group having 5 to 10 carbon atoms, represented by $R^1$ to $R^{12}$, can be exemplified by a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group.

These groups may be unsubstituted or may have a substituent. Examples of the substituent are the same as those shown as the substituents that may be possessed by the alkyl group having 1 to 6 carbon atoms, the cycloalkyl group having 5 to 10 carbon atoms, or the alkenyl group having 2 to 6 carbon atoms, represented by $R^1$ to $R^{12}$. The same holds true of the forms that the substituents can take.

The aromatic hydrocarbon group, the aromatic heterocyclic group, or the condensed polycyclic aromatic group, represented by $R^1$ to $R^{12}$, can be the same as those exemplified as the aromatic hydrocarbon group, the aromatic heterocyclic group, or the condensed polycyclic aromatic group represented by $Ar^1$ to $Ar^4$ in the aforementioned general formula (1).

These groups may be unsubstituted or may have a substituent. The substituent can be exemplified by the same ones as those shown as the substituents that may be possessed by the aromatic hydrocarbon group, the aromatic heterocyclic group, or the condensed polycyclic aromatic group represented by $Ar^1$ to $Ar^4$ in the general formula (1). The same holds true of the forms that the substituents can take.

The aryloxy group represented by $R^1$ to $R^{12}$ can be exemplified by a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group.

The aryloxy group may be unsubstituted or may have a substituent. The substituent can be exemplified by the same ones as those shown as the substituents that may be possessed by the aromatic hydrocarbon group, the aromatic heterocyclic group, or the condensed polycyclic aromatic group, represented by $Ar^1$ to $Ar^4$ in the general formula (1). The same holds true of the forms that the substituents can take.

($r^1$ to $r^{12}$)

$r^1$ to $r^{12}$ respectively show the numbers of the groups $R^1$s to $R^{12}$s bound to the aromatic ring. $r^1$, $r^2$, $r^5$, $r^8$, $r^{11}$ and $r^{12}$ each denotes an integer of 0 to 5, while $r^3$, $r^4$, $r^6$, $r^7$, $r^9$ and $r^{10}$ each denotes an integer of 0 to 4. If $r^1$ to $r^{12}$ are 0, this means that none of $R^1$ to $R^{12}$ is present on the aromatic rings. That is, the aromatic rings are not substituted by the groups represented by $R^1$ to $R^{12}$.

Figure 31:
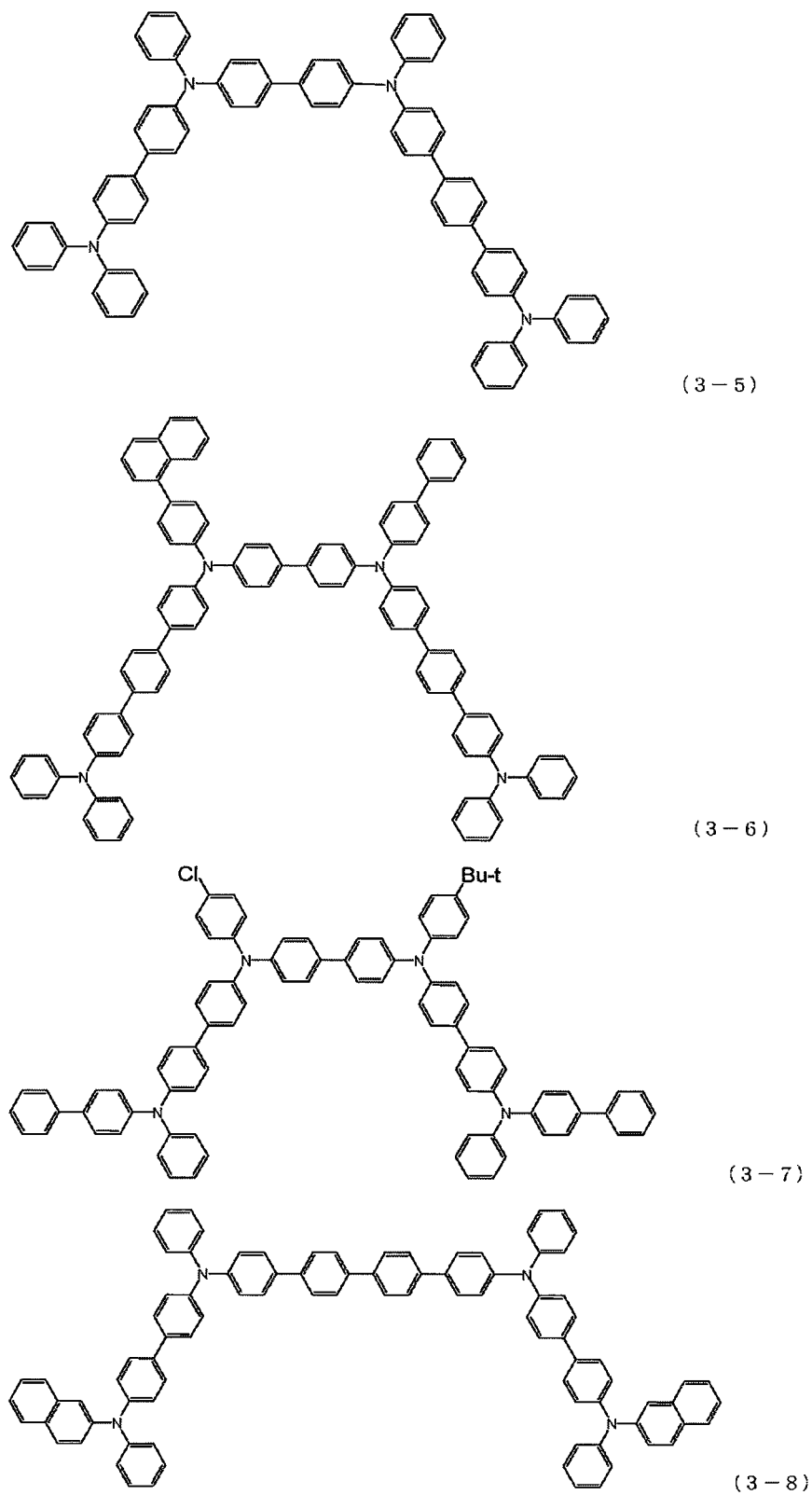
FIG. 31 is a view showing the structural formulas of Compounds 3-5 to 3-8 which are triarylamine compounds III.
Figure 32:
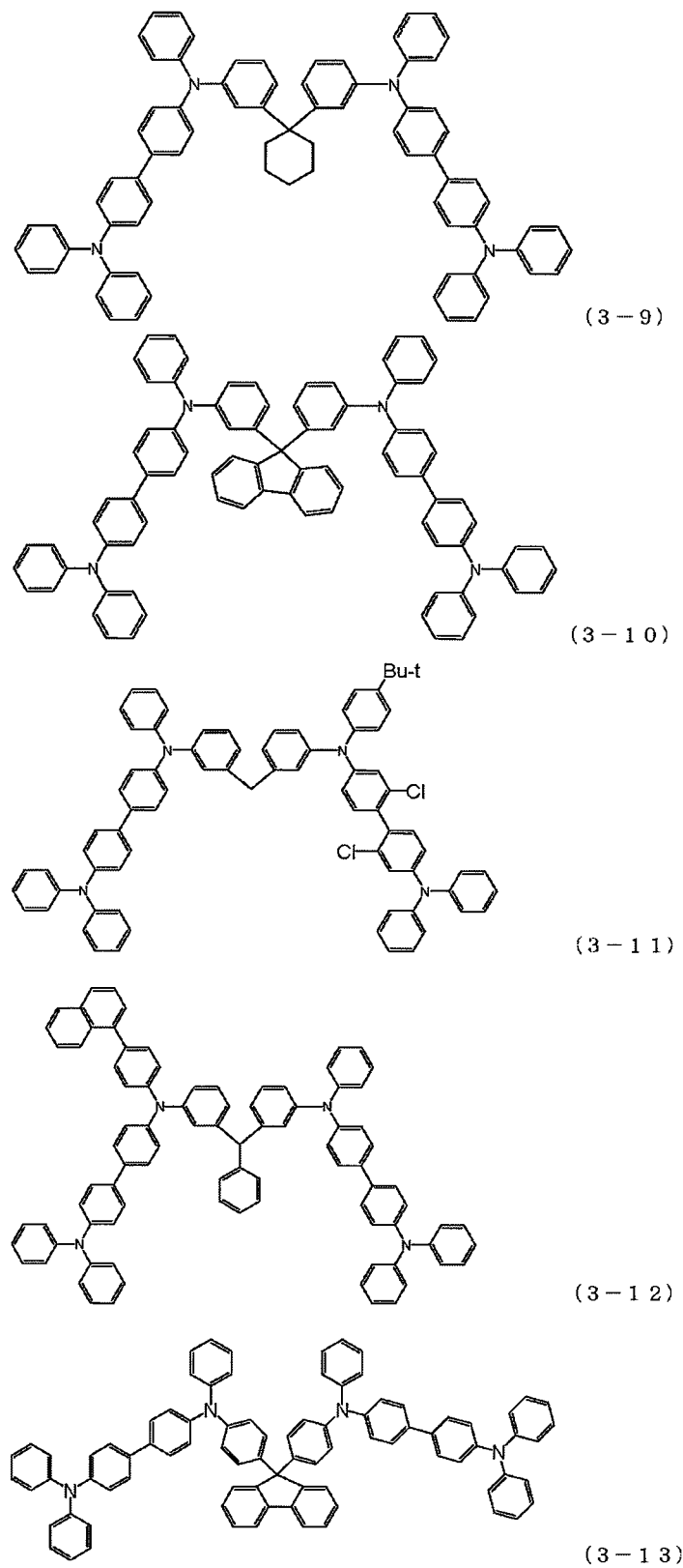
FIG. 32 is a view showing the structural formulas of Compounds 3-9 to 3-13 which are triarylamine compounds III.
Figure 33:
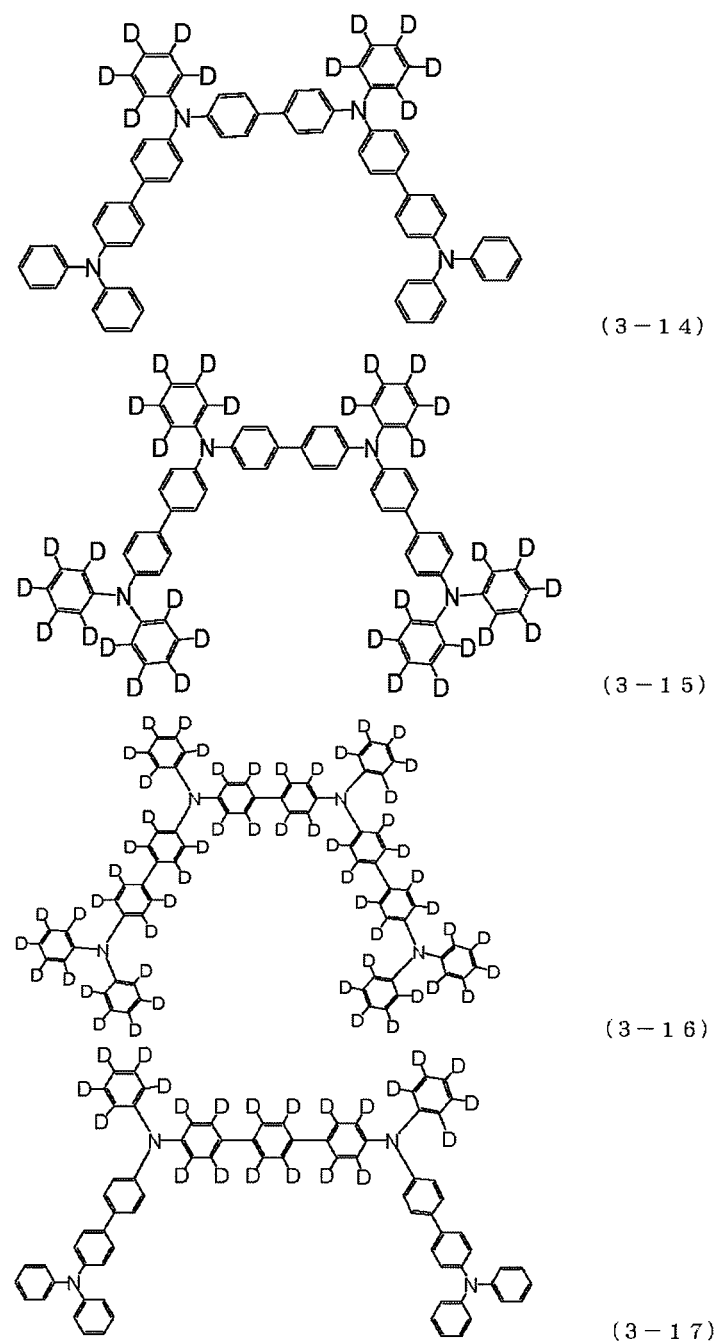
FIG. 33 is a view showing the structural formulas of Compounds 3-14 to 3-17 which are triarylamine compounds III.

If $r^1$, $r^2$, $r^5$, $r^8$, $r^{11}$ and $r^{12}$ each is an integer of 2 to 5, or if $r^3$, $r^4$, $r^6$, $r^7$, $r^9$ and $r^{10}$ each is an integer of 2 to 4, a plurality of $R^1$s to $R^{12}$s are bound to the same aromatic ring. In this case, the bound groups may be identical or different. Moreover, they may be present independently of each other without forming a ring, but they may bind to each other via a single bond, a substituted or unsubstituted methylene group, an oxygen atom, or a sulfur atom to form a ring. In Compound 3-8 of FIG. 31, for example, a plurality of substituents (2 vinyl groups) are bound together via a single bond to form a naphthalene ring.

($L^1$ to $L^3$)

In the general formula (3), $L^1$ to $L^3$ each is a bridge group linking the two triarylamine structures. $L^1$ to $L^3$ may be identical or different, and each represents a single bond, or a divalent group represented by any of the following structural formulas (B) to (G):

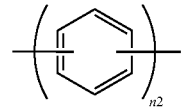
(B)

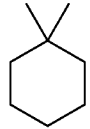
(C)

(D)

—$CH_2$— (E)

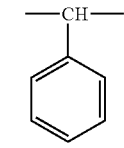
(F)

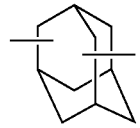
(G)

In the structural formula (B), n2 denotes an integer of 1 to 3. The divalent groups represented by the structural formulas (B) to (G) each may be unsubstituted or may be substituted by deuterium.

(Preferred Embodiments of Triarylamine Compound III)

Preferred embodiments of the triarylamine compound III will be described below. In the description of the preferred embodiments, the groups without the designation of "substituted" or "unsubstituted" may have a substituent or may be unsubstituted.

As $R^1$ to $R^{12}$, a deuterium atom, an alkyl group having 1 to 6 carbon atoms, an alkenyl group having 2 to 6 carbon atoms, an aromatic hydrocarbon group, or a condensed polycyclic aromatic group is preferred, and a deuterium atom, a phenyl group, a biphenylyl group, a naphthyl group, or a vinyl group is more preferred. Formation of a condensed aromatic ring upon binding of these groups via a single bond is also preferred, as in 3-8 of FIG. 31. A deuterium atom, a phenyl group, or a biphenylyl group is preferred in particular.

As $r^1$ to $r^{12}$, an integer of 0 to 3 is preferred, and an integer of 0 to 2 is more preferred.

As $L^1$ to $L^3$, a divalent group represented by the structural formula (B) or (D), or a single bond is preferred. A divalent group represented by the structural formula (B), or a single bond is more preferred.

As n2 in the structural formula (B), 1 or 2 is preferred, and 1 is more preferred.

Preferred examples of the triarylamine compound III are shown in FIGS. 30 to 33, but the triarylamine compounds III are not limited to these compounds. D represents a deuterium atom.

Figure 34:
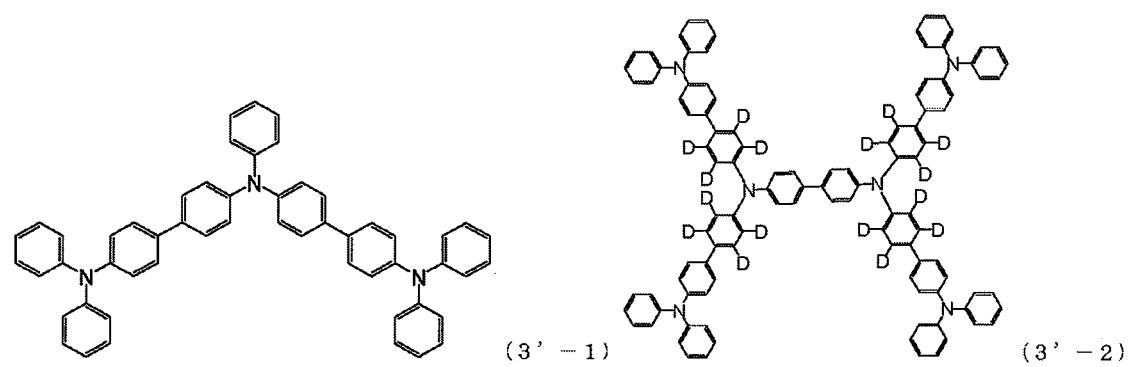
FIG. 34 is a view showing the structural formulas of triarylamine compounds having 3 to 6 triarylamine structures which are other than triarylamine compounds III.

Of the triarylamine compounds having 3 to 6 triarylamine structures in the molecule, which are preferably used in the organic EL device of the present invention, preferred examples of the triarylamine compounds other than the triarylamine compounds III are shown in FIG. 34. However, the triarylamine compounds are not limited to these compounds. D represents a deuterium atom.

The triarylamine compound III can be synthesized in accordance with a publicly known method (see Patent Documents 7 to 9).

Triarylamine Compound IV Represented by the Following General Formula (4):

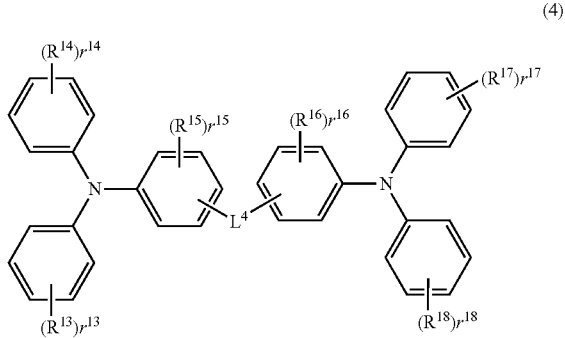

(4)

($R^{13}$ to $R^{18}$)

$R^{13}$ to $R^{18}$ may be identical or different, and each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxyl group. The alkyl group having 1 to 6 carbon atoms, the alkenyl group having 2 to 6 carbon atoms, and the alkyloxy group having 1 to 6 carbon atoms may be a straight-chain or branched.

The alkyl group having 1 to 6 carbon atoms, the cycloalkyl group having 5 to 10 carbon atoms, or the alkenyl group having 2 to 6 carbon atoms, represented by $R^{13}$ to $R^{18}$, can be exemplified by the same as that shown as the alkyl group having 1 to 6 carbon atoms, the cycloalkyl group having 5 to 10 carbon atoms, or the alkenyl group having 2 to 6 carbon atoms, represented by $R^1$ to $R^{12}$ in the general formula (3).

These groups may be unsubstituted or may have a substituent. Examples of the substituent are the same as those shown as the substituents that may be possessed by the alkyl group having 1 to 6 carbon atoms, the cycloalkyl group having 5 to 10 carbon atoms, or the alkenyl group having 2 to 6 carbon atoms, represented by $R^1$ to $R^{12}$ in the general formula (3). The same holds true of the embodiments that the substituents can adopt.

The alkyloxy group having 1 to 6 carbon atoms or the cycloalkyloxy group having 5 to 10 carbon atoms, represented by $R^{13}$ to $R^{18}$, can be exemplified by the same as that shown as the alkyloxy group having 1 to 6 carbon atoms or the cycloalkyloxy group having 5 to 10 carbon atoms, represented by $R^1$ to $R^{12}$ in the general formula (3).

These groups may be unsubstituted or may have a substituent. Examples of the substituent are the same as those shown as the substituents that may be possessed by the alkyl group having 1 to 6 carbon atoms, the cycloalkyl group having 5 to 10 carbon atoms, or the alkenyl group having 2 to 6 carbon atoms, represented by $R^1$ to $R^{12}$ in the general formula (3). The same holds true of the forms that the substituents can take.

The aromatic hydrocarbon group, the aromatic heterocyclic group, or the condensed polycyclic aromatic group, represented by $R^{13}$ to $R^{18}$, can be the same as that shown as the aromatic hydrocarbon group, the aromatic heterocyclic group, or the condensed polycyclic aromatic group represented by $Ar^1$ to $Ar^4$ in the aforementioned general formula (1).

These groups may be unsubstituted or may have a substituent. The substituent can be exemplified by the same ones as those shown as the substituents that may be possessed by the aromatic hydrocarbon group, the aromatic heterocyclic group, or the condensed polycyclic aromatic group represented by $Ar^1$ to $Ar^4$ in the general formula (1). The same holds true of the forms that the substituents can take.

The aryloxy group represented by $R^{13}$ to $R^{18}$ can be exemplified by the same as that shown as the aryloxy group represented by $R^1$ to $R^{12}$ in the general formula (3).

The aryloxy group may be unsubstituted or may have a substituent. The substituent can be exemplified by the same ones as those shown as the substituents that may be possessed by the aromatic hydrocarbon group, the aromatic heterocyclic group, or the condensed polycyclic aromatic group, represented by $Ar^1$ to $Ar^4$ in the general formula (1). The same holds true of the forms that the substituents can take.

($r^{13}$ to $r^{18}$)

$r^{13}$ to $r^{18}$ each shows the number of the groups $R^{13}$s to $R^{18}$s bound to the aromatic ring. $r^{13}$, $r^{14}$, $r^{17}$ and $r^{18}$ each denotes an integer of 0 to 5. $r^{15}$ and $r^{16}$ each denotes an integer of 0 to 4. $r^{13}$ to $r^{18}$ being 0 means that none of $R^{13}$ to $R^{18}$ is present on the aromatic rings. That is, the benzene rings are not substituted by the groups represented by $R^{13}$ to $R^{18}$.

If $r^{13}$, $r^{14}$, $r^{17}$ and $r^{18}$ each is an integer of 2 to 5, or if $r^{15}$ and $r^{16}$ each is an integer of 2 to 4, a plurality of $R^{13}$s to $R^{18}$s are bound to the same aromatic ring. In this case, the bound groups may be identical or different. Moreover, they may be present independently of each other without forming a ring, but may bind to each other via a single bond, a substituted or unsubstituted methylene group, an oxygen atom, or a sulfur atom to form a ring. In Compounds 4-13 and 4-14 of FIG. 36, for example, a plurality of substituents (2 vinyl groups) are bound together via a single bond to form a naphthalene ring.

($L^4$)

In the general formula (4), $L^4$ is a bridge group linking the two triarylamine structures. $L^4$ represents a single bond, or a divalent group represented by any of the aforementioned structural formulas (C) to (G).

(Preferred Embodiments of Triarylamine Compound IV)

Preferred embodiments of the triarylamine compound IV will be described below. In the description of the preferred embodiments, the groups without the designation of "substituted" or "unsubstituted" may have a substituent or may be unsubstituted.

Figure 36:
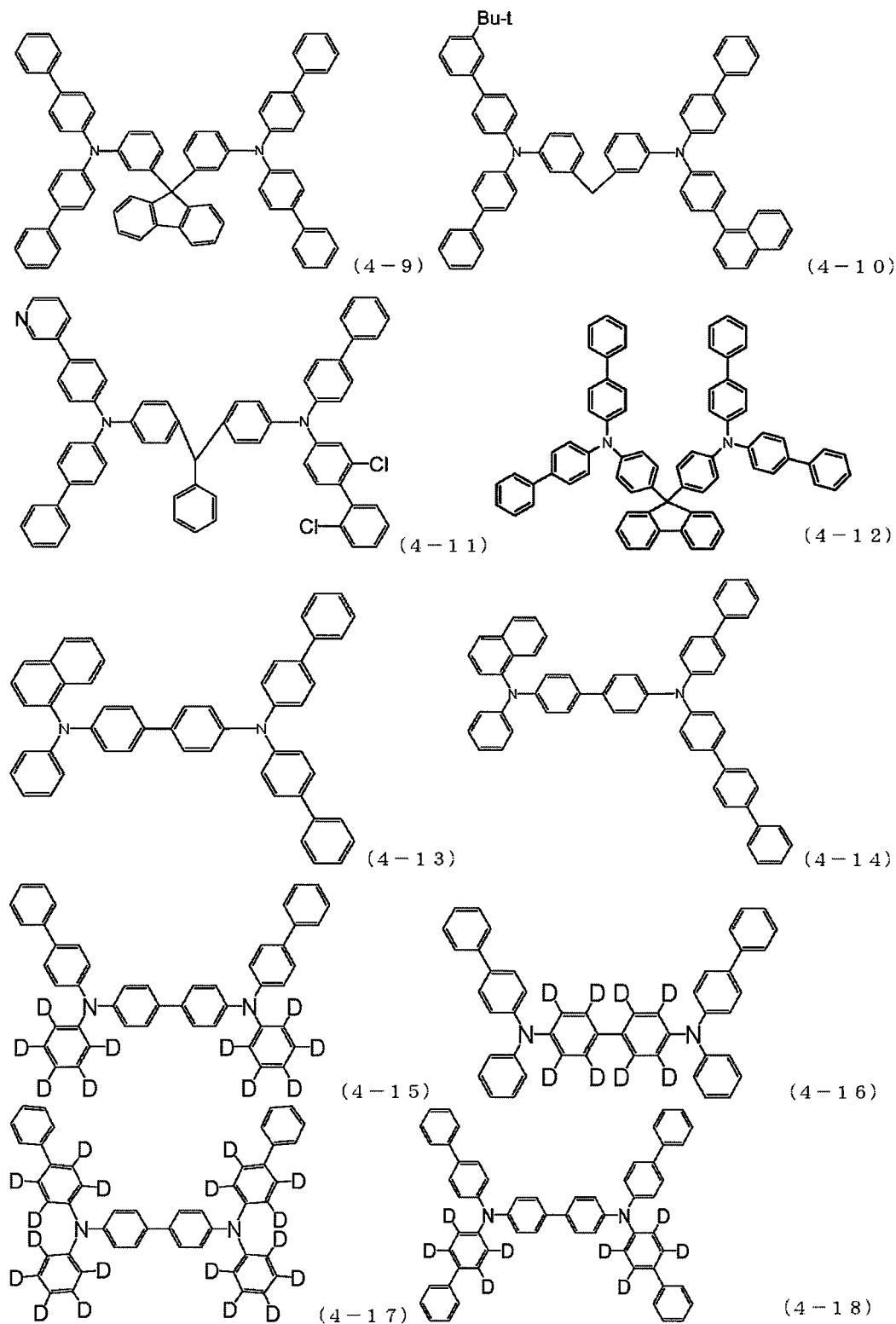
FIG. 36 is a view showing the structural formulas of Compounds 4-9 to 4-18 which are triarylamine compounds IV.

As $R^{13}$ to $R^{18}$, a deuterium atom, a chlorine atom, an alkyl group having 1 to 6 carbon atoms, an alkenyl group having 2 to 6 carbon atoms, an aromatic hydrocarbon group, a nitrogen-containing aromatic heterocyclic group, or a condensed polycyclic aromatic group is preferred, and a deuterium atom, a phenyl group, a biphenylyl group, a naphthyl group, or a vinyl group is more preferred. Formation of a condensed aromatic ring upon binding of these groups via a single bond, as in Compounds 4-13 and 4-14 of FIG. 36, is also preferred. A deuterium atom, a phenyl group, or a biphenylyl group is preferred in particular.

As $r^{13}$ to $r^{18}$, an integer of 0 to 3 is preferred, and an integer of 0 to 2 is more preferred.

As $L^4$, a divalent group represented by the structural formula (D) or (G), or a single bond is preferred.

Figure 35:
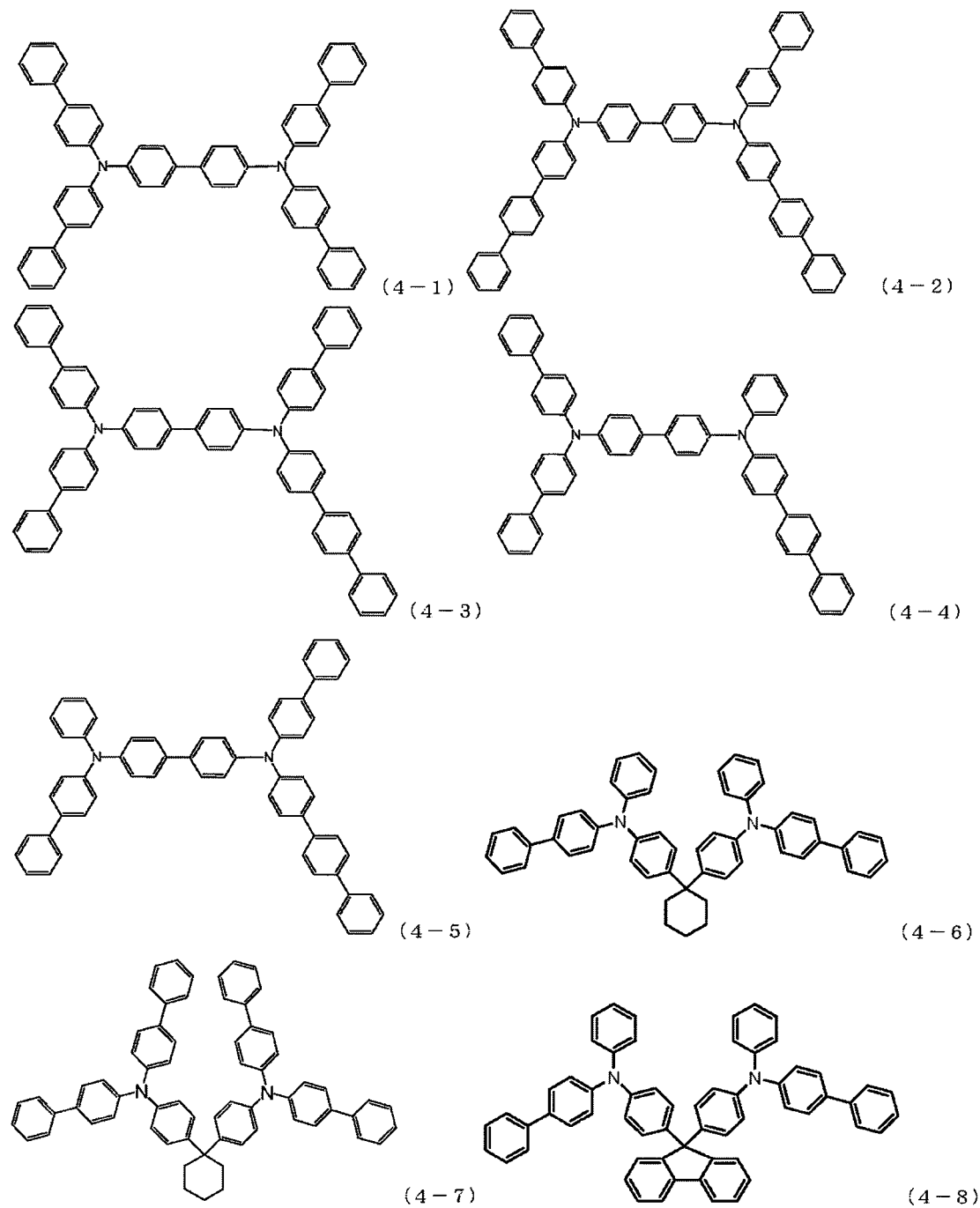
FIG. 35 is a view showing the structural formulas of Compounds 4-1 to 4-8 which are triarylamine compounds IV.
Figure 37:
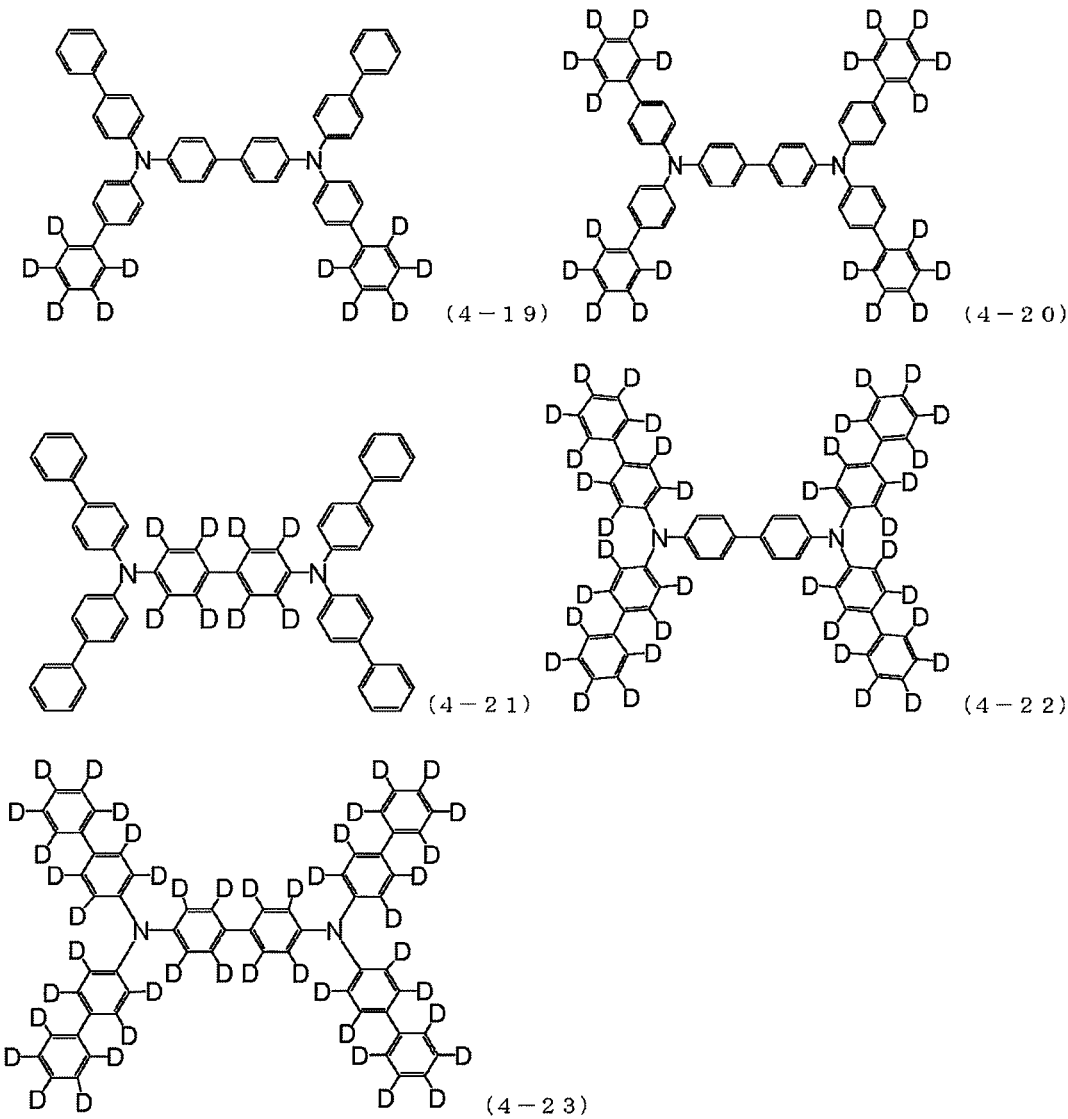
FIG. 37 is a view showing the structural formulas of Compounds 4-19 to 4-23 which are triarylamine compounds IV.

Preferred examples of the triarylamine compound IV are shown in FIGS. 35 to 37, but the triarylamine compounds IV are not limited to these compounds. D represents a deuterium atom.

Of the triarylamine compounds having 2 triarylamine structures, which are preferably used in the organic EL device of the present invention, examples of the triarylamine compounds other than the triarylamine compounds IV are shown in FIG. 38. However, the triarylamine compounds are not limited to these compounds.

The triarylamine compound IV can be synthesized in accordance with a publicly known method (see Patent Documents 7 to 9).

The above-mentioned materials may be subjected singly to film formation, or any of which may be mixed with other of them and subjected to film formation. The first hole transport layer 4 may have a structure in which layers each formed from any one of these materials are stacked; a structure in which layers each formed from a mixture of these materials are stacked; or a structure in which a layer of a single material and a layer of a mixture thereof are stacked.

For the first hole transport layer 4, the material usually used for the layer can be further p-doped with tris(bromophenyl)aminium hexachloroantimonate or a radialene derivative (see, for example, WO2014/009310), or a polymeric compound containing the structure of a benzidine derivative such as TPD in its partial structure can be used.

In forming the hole injection layer 3 concurrently serving as the first hole transport layer 4, a coating type polymeric material such as poly(3,4-ethylenedioxythiophene) (PEDOT)/poly(styrene sulfonate) (PSS) can be used.

<Second Hole Transport Layer 5>

In the organic EL device of the present invention, the second hole transport layer 5 is provided between the first hole transport layer 4 and the luminous layer 6, and the arylamine compound I is used for such a second hole transport layer 5. For the second hole transport layer 5, a publicly known material with hole transport properties may be used concurrently, as long as this material does not impair the effects of the present invention. Examples of the publicly known material with hole transport properties include the same ones as those illustrated in connection with the first hole transport layer 4. These materials may be subjected singly to film formation, or any of them may be mixed with other of them and subjected to film formation. The second hole transport layer 5 may have a structure in which layers each formed from any one of these materials are stacked; a structure in which layers each formed from a mixture of these materials are stacked; or a structure in which a layer of a single material and a layer of a mixture thereof are stacked.

<Electron Blocking Layer>

In the organic EL device of the present invention, an electron blocking layer can be provided between the second hole transport layer 5 and the luminous layer 6, although this is not shown in FIG. 1. For the electron blocking layer, the aforementioned arylamine compound I can be used from the viewpoint of its high electron blocking performance. If the arylamine compound I is used in the electron blocking layer, however, the composition of the electron blocking layer and the aforementioned composition of the second hole transport layer 5 have to be different. Alternatively, the triarylamine compound III or IV can be used.

Furthermore, a publicly known compound having electron blocking action can be used. Examples of the publicly known compound having electron blocking action include the following:

Carbazole derivatives, for example,
4,4',4''-tri(N-carbazolyl)triphenylamine (TCTA),
9,9-bis[4-(carbazol-9-yl)phenyl]fluorene,
1,3-bis(carbazol-9-yl)benzene (mCP), and
2,2-bis(4-carbazol-9-ylphenyl)adamantane (Ad-Cz); and Compounds having a triphenylsilyl group and a triarylamine structure, for example,
9-[4-(carbazol-9-yl)phenyl]-9-[4-(triphenylsilyl)phenyl]-9H-fluorene.

These materials may be subjected singly to film formation, or any of them may be mixed with other of them and subjected to film formation. The electron blocking layer may have a structure in which layers each formed from any one of these materials are stacked; a structure in which layers each formed from a mixture of these materials are stacked; or a structure in which a layer of a single material and a layer of a mixture thereof are stacked.

<Luminous Layer 6>

The luminous layer 6 is formed on the second hole transport layer 5 (or electron blocking layer). For the luminous layer 6, there can be used metal complexes of quinolinol derivatives including $Alq_3$; various metal complexes; anthracene derivatives; bisstyrylbenzene derivatives; pyrene derivatives; oxazole derivatives; and polyparaphenylenevinylene derivatives.

The luminous layer 6 may be composed of a host material and a dopant material.

A preferred example of the host material is an anthracene derivative. Other examples usable include the above luminescent materials; heterocyclic compounds having an indole ring as a partial structure of a condensed ring; heterocyclic compounds having a carbazole ring as a partial structure of a condensed ring; carbazole derivatives; thiazole derivatives; benzimidazole derivatives; and polydialkylfluorene derivatives.

As the dopant material, there can be preferably used blue light emitting dopants such as pyrene derivatives; and amine derivatives having a fluorene ring as a partial structure of a condensed ring. Other materials usable include quinacridone, coumarin, rubrene, perylene, and derivatives thereof; benzopyran derivatives; indenophenanthrene derivatives; rhodamine derivatives; and aminostyryl derivatives.

These materials may be subjected singly to film formation, but any of them may be mixed with other of them and subjected to film formation. The electron blocking layer may have a structure in which layers each formed from any one of these materials are stacked; a structure in which layers each formed from a mixture of these materials are stacked; or a structure in which a layer of a single material and a layer of a mixture thereof are stacked.

Furthermore, a phosphorescent luminous substance can be used as the luminescent material. As the phosphorescent luminous substance, a phosphorescent luminous substance in the form of a metal complex containing iridium, platinum or the like can be used. Concretely, a green phosphorescent luminous substance such as $Ir(ppy)_3$; a blue phosphorescent luminous substance such as FIrpic or $FIr_6$; or a red phosphorescent luminous substance such as $Btp_2Ir(acac)$ may be used.

As the host material in this case, the following hole injecting/transporting host material, for example, can be used:

A carbazole derivative, for example,
4,4'-di(N-carbazolyl)biphenyl (CBP), TCTA, or mCP.

The following electron transporting host material, for example, is also usable:
p-bis(triphenylsilyl)benzene (UGH2), or
2,2',2"-(1,3,5-phenylene)-tris(1-phenyl-1H-benzimidazole) (TPBI).

By using such a host material, a high performance organic EL device can be prepared.

Doping of the host material with the phosphorescent luminous substance is preferably performed by codeposition in a range of 1 to 30% by weight based on the entire luminous layer in order to avoid concentration quenching.

Moreover, a material which emits delayed fluorescence, such as a CDCB derivative, for example, PIC-TRZ, CC2TA, PXZ-TRZ, or 4CzIPN, can be used as the luminescent material.

<Hole Blocking Layer>

A hole blocking layer (not shown) can be provided between the luminous layer 6 and the electron transport layer 7. For the hole blocking layer, a publicly known compound having hole blocking action can be used. Examples of the publicly known compound having hole blocking action include the following:

Phenanthroline derivatives, e.g., bathocuproine (BCP);
Metal complexes of quinolinol derivatives, e.g., aluminum(III) bis(2-methyl-8-quinolinolato)-4-phenylphenolate (BAlq);
Various rare earth complexes;
Triazole derivatives;
Triazine derivatives; and
Oxadiazole derivatives.

These materials may also concurrently serve as the materials for the electron transport layer 7. These materials may be subjected singly to film formation, but any of them may be mixed with other of them and subjected to film formation. The hole blocking layer may have a structure in which layers each formed from any one of these materials are stacked; a structure in which layers each formed from a mixture of these materials are stacked; or a structure in which a layer of a single material and a layer of a mixture thereof are stacked.

<Electron Transport Layer 7>

In the present invention, the aforementioned pyrimidine derivative II is used for the electron transport layer 7. As the pyrimidine derivative II, the one represented by the general formula (2a) or (2b) is preferred, and the one represented by the general formula (2a) is more preferred.

For the electron transport layer 7, a publicly known material with electron transport properties may be used concurrently, as long as this material does not impair the effects of the present invention. Examples of the publicly known material with electron transport properties include metal complexes of quinolinol derivatives including $Alq_3$ and BAlq; various metal complexes; triazole derivatives; triazine derivatives; oxadiazole derivatives; pyridine derivatives; pyrimidine derivatives; benzimidazole derivatives; thiadiazole derivatives; anthracene derivatives; carbodiimide derivatives; quinoxaline derivatives; pyridoindole derivatives; phenanthroline derivatives; and silole derivatives. These materials may be subjected singly to film formation, but any of them may be mixed with other of them and subjected to film formation. The hole blocking layer may have a structure in which layers each formed from any one of these materials are stacked; a structure in which layers each formed from a mixture of these materials are stacked; or a structure in which a layer of a single material and a layer of a mixture thereof are stacked.

<Electron Injection Layer 8>

For the electron injection layer 8, there can be used an alkali metal salt such as lithium fluoride or cesium fluoride; an alkaline earth metal salt such as magnesium fluoride; or a metal oxide such as aluminum oxide. However, these materials can be omitted in the suitable selection of the electron transport layer and the cathode.

<Cathode 9>

For the cathode 9, an electrode material with a low work function such as aluminum, or an alloy having a lower work function, such as a magnesium-silver alloy, a magnesium-indium alloy, or an aluminum-magnesium alloy, is used as an electrode material.

EXAMPLES

The embodiments of the present invention will now be described more specifically by the following Examples, but the present invention is in no way limited to these Examples.

Synthesis Example 1: Compound 1-34

Synthesis of 4,4"-bis{(9,9-dimethyl-9H-fluoren-2-yl)-phenylamino}-1,1': 3',1"-terphenyl

| | |
|---|---|
| A nitrogen-purged reaction vessel was charged with 4,4"-dibromo-1,1':3',1"-terphenyl | 8.81 g, |
| 2-(phenylamino)-9,9-dimethyl-9H-fluorene | 13.6 g, |
| tert-butoxysodium | 5.12 g, |
| tris(dibenzylideneacetone)dipalladium | 0.33 g, |
| a 50% (w/v) toluene solution of tri-tert-butylphosphine and | 0.63 ml, |
| toluene | 150 ml. |

The charged contents were heated, refluxed for 2 hours by stirring, and allowed to cool to prepare a reaction liquid. Then, methanol was added to the reaction liquid, and the resulting precipitate was collected by filtration. The precipitate was dissolved by heating in chlorobenzene, and the solution was subjected to adsorption purification using silica gel. Then, adsorption purification using activated clay was performed whereafter crystallization using a chlorobenzene/methanol mixed solvent was carried out. Then, reflux cleaning using methanol was performed. As a result, 16.25 g (yield 90%) of Compound 1-34 was obtained as a white powder.

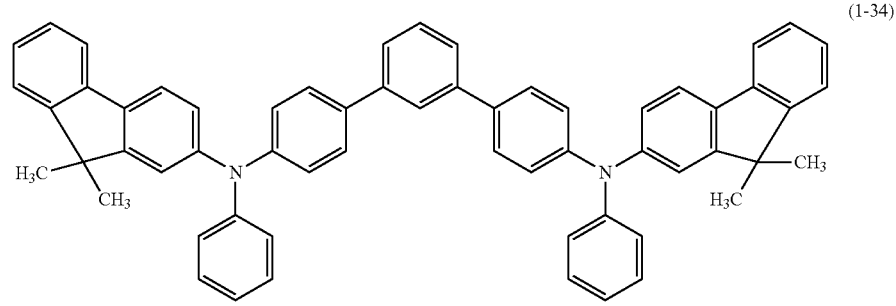 [SMILES: CC1(C)c2ccccc2-c2ccc(N(c3ccccc3)c3ccc(-c4cccc(-c5ccc(N(c6ccccc6)c6ccc7c(c6)C(C)(C)c6ccccc6-7)cc5)c4)cc3)cc21]

(1-34)

For the resulting white powder, its structure was identified using NMR. In $^1$H-NMR (CDCl$_3$), the following signals of 48 hydrogens were detected.
δ (ppm)=7.84 (1H)
7.70-7.03 (35H)
1.48 (12H)

Synthesis Example 2: Compound 1-88

Synthesis of 4,4''-bis{(triphenylen-2-yl)-phenylamino}-1,1';4',1''-terphenyl

Reactions were performed under the same conditions as in Synthesis Example 1, except that
4,4''-diiodo-1,1';4',1''-terphenyl
was used instead of
4,4''-dibromo-1,1':3',1''-terphenyl, and
(triphenylen-2-yl)-phenylamine
was used instead of
2-(phenylamino)-9,9-dimethyl-9H-fluorene.
As a result, 11.4 g (yield 74%) of Compound 1-88 was obtained as a white powder.

Synthesis Example 3: Compound 1-92

Synthesis of 4,4''-bis{N-(2-phenyl-biphenyl-4-yl)-N-phenylamino}-1,1':4',1''-terphenyl

| | |
|---|---|
| A nitrogen-purged reaction vessel was charged with N-(2-phenyl-biphenyl-4-yl)-N-phenylamine | 13.1 g, |
| 4,4''-diiodo-1,1':4',1''-terphenyl | 20.0 g, |
| copper powder | 0.18 g, |
| potassium carbonate | 11.3 g, |
| 3,5-di-tert-butylsalicylic acid | 0.70 g, |
| sodium bisulfite | 0.86 g, |
| and | |
| dodecylbenzene | 30 ml. |

The charged contents were heated, stirred for 24 hours at 210° C., and allowed to cool, thereby obtaining a mixture. To the mixture, 30 ml of xylene and 60 ml of methanol were

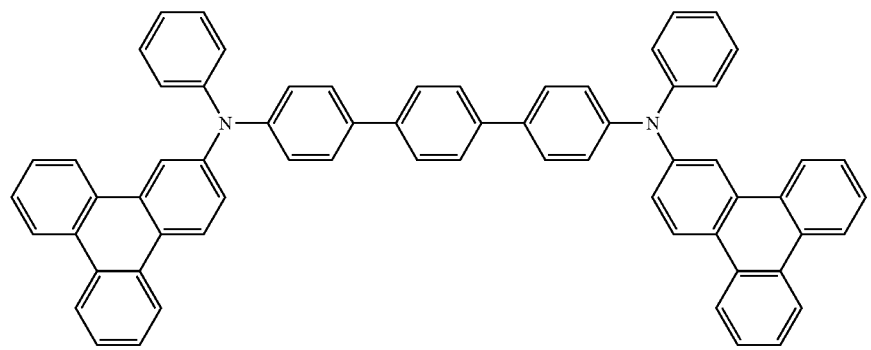

(1-88)

For the resulting white powder, its structure was identified using NMR. In $^1$H-NMR (THF-d$_8$), the following signals of 44 hydrogens were detected.
δ (ppm)=8.72-8.62 (8H)
8.45 (2H)
8.36 (2H)
7.75 (4H)
7.70-7.21 (26H)
7.09 (2H)

added, whereafter precipitated solids were collected by filtration. The resulting solids were dissolved in toluene, and the solution was subjected to adsorption purification using silica gel. Then, crystallization using ethyl acetate, and crystallization using methanol were performed. Then, purification by recrystallization using chlorobenzene was performed. Further, reflux cleaning using 200 ml of methanol was performed. As a result, 17.0 g (yield 72%) of Compound 1-92 was obtained as a yellowish white powder.

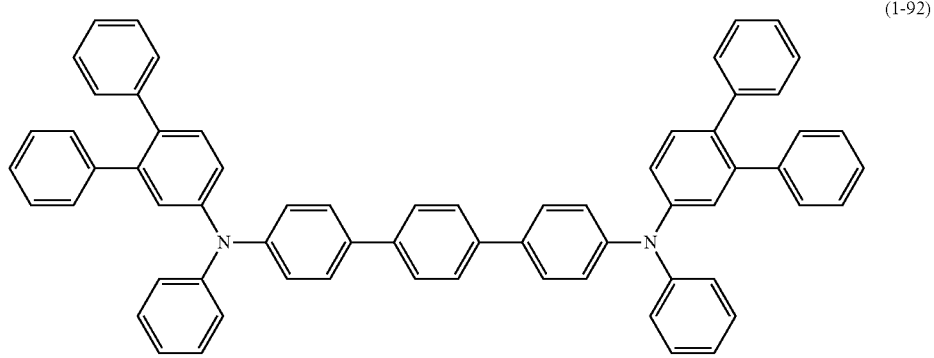 [SMILES: c1ccc(-c2ccc(N(c3ccccc3)c3ccc(-c4ccc(-c5ccc(N(c6ccccc6)c6ccc(-c7ccccc7)c(-c7ccccc7)c6)cc5)cc4)cc3)cc2-c2ccccc2)cc1]

(1-92)

For the resulting yellowish white powder, its structure was identified using NMR. In $^1$H-NMR (CDCl$_3$), the following signals of 48 hydrogens were detected.

δ (ppm)=7.68 (4H)
7.62-7.55 (4H)
7.38-7.09 (40H)

Synthesis Example 4: Compound 1-93

Synthesis of 4,4''-bis{(biphenyl-4-yl)-phenylamino}-1,1':4',1'':4'',1'''-quaterphenyl

| | |
|---|---|
| A nitrogen-purged reaction vessel was charged with N-phenyl-N-{4-(4,4,5,5-tetramethyl-1,3,2-dioxaborolan-2-yl)phenyl}-(1,1'-biphenyl-4-yl)amine | 18.2 g, |
| 4,4'-diiodobiphenyl | 7.5 g, |
| a 2M aqueous solution of potassium carbonate | 46 ml, |
| toluene | 60 ml, |
| and | |
| ethanol | 15 ml. |

A nitrogen gas was passed through the charged contents for 1 hour to obtain a mixture. To the mixture, 1.1 g of tetrakis(triphenylphosphine)palladium was added to obtain a reaction liquid. The reaction liquid was heated and stirred for 10 hours at 72° C. The reaction liquid after stirring was cooled to room temperature, and 60 ml of methanol was added thereto. Precipitated solids were collected by filtration, and washed with 100 ml of a methanol/water (5/1, v/v) mixed solution. Then, 100 ml of 1,2-dichlorobenzene was added to the solids after washing, and the solids were dissolved upon heating. After insolubles were removed by filtration, the solution was allowed to cool and, upon addition of 200 ml of methanol, a crude product was precipitated. The precipitated crude product was collected by filtration. The crude product was subjected to reflux cleaning using 100 ml of methanol. As a result, 11.8 g (yield 81%) of Compound 1-93 was obtained as a pale yellow powder.

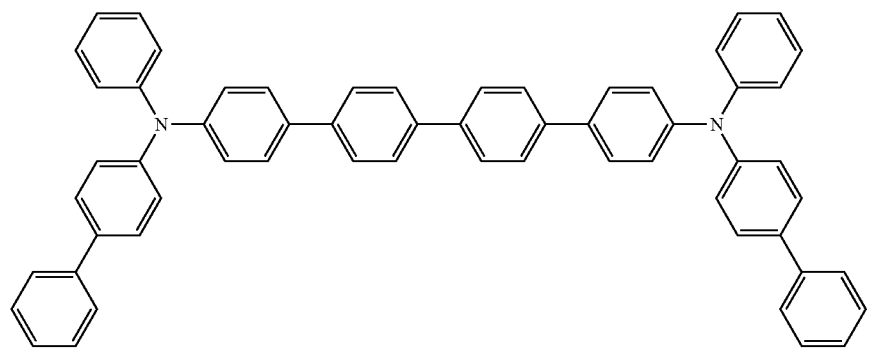

(1-93)

For the resulting pale yellow powder, its structure was identified using NMR. In $^1$H-NMR (CDCl$_3$), the following signals of 44 hydrogens were detected.

δ (ppm)=7.66-7.77 (8H)
7.50-7.64 (12H)
7.42-7.50 (4H)
7.28-7.38 (6H)
7.20-7.26 (12H)
7.08 (2H)

Synthesis Example 5: Compound 1-114

Synthesis of 4,4''-bis{(naphthalen-1-yl)-phenylamino}-1,1':3',1'':3'',1'''-quaterphenyl Reactions were performed under the same conditions as in Synthesis Example 4, except that
3,3'-dibromobiphenyl
was used instead of
4,4'-diiodobiphenyl, and
N-phenyl-N-{4-(4,4,5,5-tetramethyl-1,3,2-dioxaborolan-2-yl)phenyl}-(naphthalen-1-yl)amine
was used instead of
N-phenyl-N-{4-(4,4,5,5-tetramethyl-1,3,2-dioxaborolan-2-yl)phenyl}-(1,1'-biphenyl-4-yl)amine.
As a result, 4.00 g (yield 26%) of Compound 1-114 was obtained as a pale yellow powder.

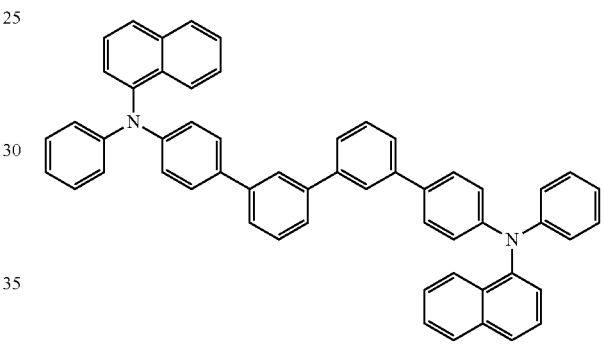

(1-114)

For the resulting pale yellow powder, its structure was identified using NMR. In $^1$H-NMR (CDCl$_3$), the following signals of 40 hydrogens were detected.

δ (ppm)=7.99 (2H)
7.92 (2H)
7.78-7.85 (4H)
7.35-7.61 (18H)
7.19-7.28 (4H)
7.06-7.15 (8H)
6.98 (2H)

Synthesis Example 6: Compound 1-130

Synthesis of 4,4''-bis{(biphenyl-4-yl)-phenylamino}-1,1':3',1'':4'',1'''-quaterphenyl

| | |
|---|---|
| A nitrogen-purged reaction vessel was charged with N-phenyl-N-{4-(4,4,5,5-tetramethyl-1,3,2-dioxaborolan-2-yl)phenyl}-(1,1'-biphenyl-4-yl)amine | 18.2 g, |
| 3,4'-dibromobiphenyl | 7.5 g, |
| a 2M aqueous solution of potassium carbonate | 46 ml, |
| toluene | 60 ml, |
| and ethanol | 15 ml. |

A nitrogen gas was passed through the charged contents for 1 hour to obtain a mixture. To the mixture, 1.1 g of tetrakis(triphenylphosphine)palladium was added to prepare a reaction liquid. The reaction liquid was heated and stirred for 10 hours at 72° C. The reaction liquid after stirring was cooled to room temperature, and 60 ml of methanol was added thereto. Precipitated solids were collected by filtration, and washed with 100 ml of a methanol/water (5/1, v/v) mixed solution. Then, 100 ml of 1,2-dichlorobenzene was added to the solids, and the mixture was heated until the solids were dissolved. Insolubles were removed by filtration. Then, the solution was allowed to cool and, upon addition of 200 ml of methanol, a crude product was precipitated. The precipitated crude product was collected by filtration. The crude product was subjected to reflux cleaning using 100 ml of methanol. As a result, 14.0 g (yield 84%) of Compound 1-130 was obtained as a pale yellow powder.

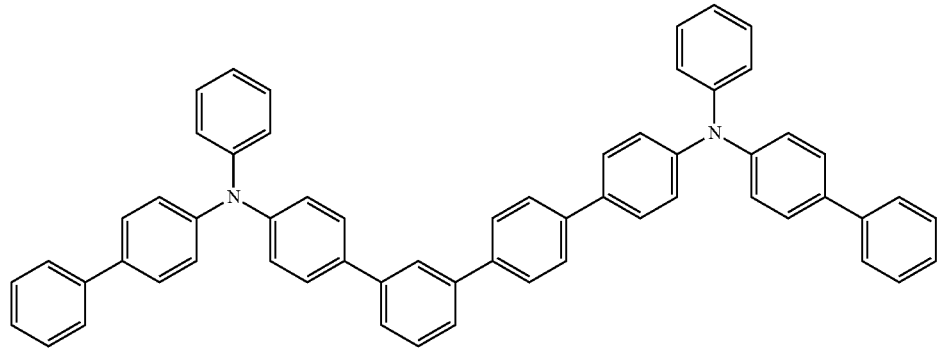

(1-130)

For the resulting pale yellow powder, its structure was identified using NMR. In $^1$H-NMR (CDCl$_3$), the following signals of 44 hydrogens were detected.

δ (ppm)=7.00-8.00 (44H)

The glass transition points of the compounds obtained in the Synthesis Examples were measured by a high sensitivity differential scanning calorimeter (DSC3100S, produced by Bruker AXS GmbH).

| | Glass transition point (° C.) |
|---|---|
| Compound 1-34 of Synthesis Example 1 | 124 |
| Compound 1-88 of Synthesis Example 2 | 163 |
| Compound 1-92 of Synthesis Example 3 | 124 |
| Compound 1-93 of Synthesis Example 4 | 119 |
| Compound 1-114 of Synthesis Example 5 | 112 |
| Compound 1-130 of Synthesis Example 6 | 117 |

The arylamine compound I had a glass transition point of 100° C. or higher, demonstrating that it was stable in a thin film state.

Using each of the compounds obtained in the Synthesis Examples, a vapor deposited film with a film thickness of 100 nm was prepared on an ITO substrate, and its work function was measured using an ionization potential measuring device (PYS-202, produced by Sumitomo Heavy Industries, Ltd.).

| | Work function (eV) |
|---|---|
| Compound 1-34 of Synthesis Example 1 | 5.65 |
| Compound 1-88 of Synthesis Example 2 | 5.62 |
| Compound 1-92 of Synthesis Example 3 | 5.67 |
| Compound 1-93 of Synthesis Example 4 | 5.68 |
| Compound 1-114 of Synthesis Example 5 | 5.81 |
| Compound 1-130 of Synthesis Example 6 | 5.74 |

The arylamine compound I showed a suitable energy level as compared with a work function of 5.5 eV of an ordinary hole transport material such as NPD or TPD, and thus, it was found to have satisfactory hole transport capability.

Synthesis Example 7: Compound 2-1

Synthesis of 2-(biphenyl-4-yl)-4-phenyl-6-{4'-(pyridin-3-yl)biphenyl-4-yl}pyrimidine

| | |
|---|---|
| A nitrogen-purged reaction vessel was charged with 2-chloro-4-phenyl-6-{4'-(pyridin-3-yl)biphenyl-4-yl}pyrimidine | 8.0 g, |
| 4-biphenylboronic acid | 3.8 g, |
| tetrakistriphenylphosphine | 0.44 g, |
| potassium carbonate | 7.9 g, |
| toluene | 80 ml, |
| tetrahydrofuran | 80 ml, |
| and water | 40 ml. |

The charged contents were heated, and stirred for 12 hours at 80° C. to obtain a reaction liquid. The reaction liquid was cooled to room temperature, and an organic layer was collected by a liquid separating operation. The collected organic layer was concentrated under reduced pressure to obtain a crude product. The crude product was purified by column chromatography (carrier: silica gel, eluting solution: ethyl acetate/heptane), and then purified by recrystallization using a tetrahydrofuran/acetone mixed solvent. As a result, 3.0 g (yield 30%) of Compound 2-1 was obtained as a white powder.

(2-1)

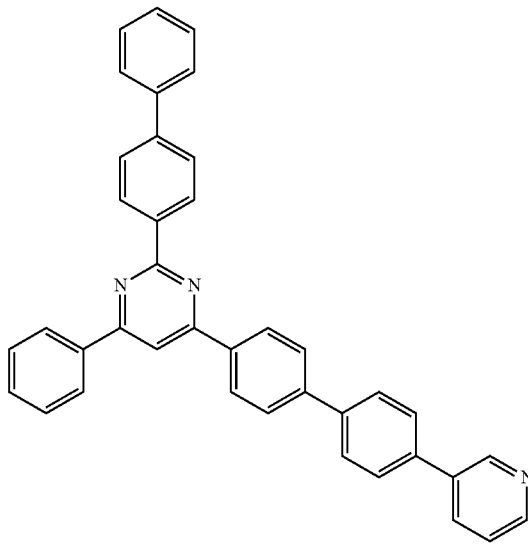

For the resulting white powder, its structure was identified using NMR. In $^1$H-NMR (CDCl$_3$), the following signals of 27 hydrogens were detected.

δ (ppm)=8.94 (1H)

8.83 (2H)

8.64 (1H)

8.43-8.32 (4H)

8.07 (1H)

7.97-7.35 (18H)

Synthesis Example 8: Compound 2-2

Synthesis of 2-{4-(naphthalen-1-yl)phenyl}-4-phenyl-6-{4'-(pyridin-3-yl)biphenyl-4-yl}pyrimidine Reactions were performed under the same conditions as in Synthesis Example 7, except that {4-(naphthalen-1-yl)phenyl}boronic acid was used instead of 4-biphenylboronic acid.

As a result, 1.6 g (yield 15%) of Compound 2-2 was obtained as a white powder.

(2-2)

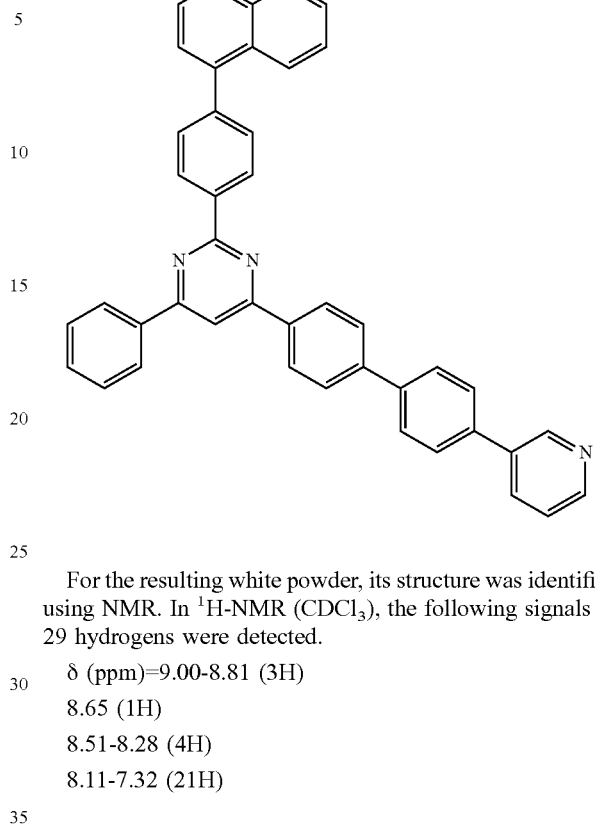

For the resulting white powder, its structure was identified using NMR. In $^1$H-NMR (CDCl$_3$), the following signals of 29 hydrogens were detected.

δ (ppm)=9.00-8.81 (3H)

8.65 (1H)

8.51-8.28 (4H)

8.11-7.32 (21H)

Synthesis Example 9: Compound 2-16

Synthesis of 2-{4-(naphthalen-1-yl)phenyl}-4-(naphthyl-1-yl)-6-{4'-(pyridin-3-yl)biphenyl-4-yl}pyrimidine

| | |
|---|---|
| A nitrogen-purged reaction vessel was charged with | 4.5 g, |
| 2-chloro-4-(naphthyl-1-yl)-6-{4'-(pyridin-3-yl)biphenyl-4-yl}pyrimidine | |
| {4-(naphthalen-1-yl)phenyl}boronic acid | 2.61 g, |
| tetrakistriphenylphosphine | 0.22 g, |
| potassium carbonate | 3.97 g, |
| toluene | 45 ml, |
| ethanol | 11.3 ml, |
| and | |
| water | 14.4 ml. |

The charged contents were heated, and stirred for 12 hours at 70° C. to obtain a reaction liquid. The reaction liquid was cooled to room temperature, and an organic stratum was collected by a liquid separating operation. The collected organic stratum was concentrated under reduced pressure to obtain a crude product. The crude product was purified by column chromatography (carrier: silica gel, eluting solution: ethyl acetate/heptane), and then purified by recrystallization using a toluene/acetone mixed solvent. As a result, 3.0 g (yield 49.2%) of Compound 2-16 was obtained as a white powder.

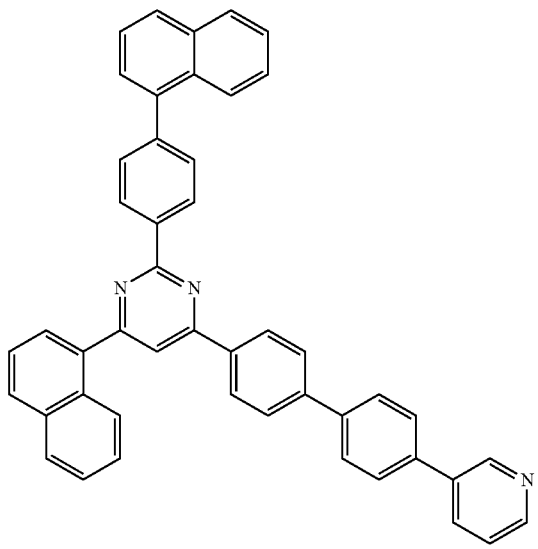

(2-16)

For the resulting white powder, its structure was identified using NMR. In $^1$H-NMR (CDCl$_3$), the following signals of 31 hydrogens were detected.

δ (ppm)=9.00-8.81 (2H)
8.65 (1H)
8.51-8.28 (2H)
8.20-7.35 (26H)

The glass transition points of the pyrimidine derivatives obtained in the Synthesis Examples were measured by a high sensitivity differential scanning calorimeter (DSC3100S, produced by Bruker AXS GmbH).

|  | Glass transition point (° C.) |
|---|---|
| Compound 2-2 of Synthesis Example 8 | 104 |
| Compound 2-16 of Synthesis Example 9 | 115 |

The pyrimidine derivative II had a glass transition point of 100° C. or higher, demonstrating that it was stable in a thin film state.

Using each of the pyrimidine derivatives obtained in the Synthesis Examples, a vapor deposited film with a film thickness of 100 nm was prepared on an ITO substrate, and its work function was measured using an ionization potential measuring device (PYS-202, produced by Sumitomo Heavy Industries, Ltd.).

|  | Work function (eV) |
|---|---|
| Compound 2-1 of Synthesis Example 7 | 6.61 |
| Compound 2-2 of Synthesis Example 8 | 6.56 |
| Compound 2-16 of Synthesis Example 9 | 6.56 |

The pyrimidine derivative II showed a greater value than a work function of 5.5 eV which an ordinary hole transport material such as NPD or TPD has. Thus, it was found to have high hole blocking capability.

<Device Example 1>

The hole injection layer 3, the first hole transport layer 4, the second hole transport layer 5, the luminous layer 6, the electron transport layer 7, the electron injection layer 8, and the cathode (aluminum electrode) 9 were vapor-deposited in this order on an ITO electrode formed beforehand as the transparent anode 2 on the glass substrate 1, thereby preparing an organic EL device as shown in FIG. 1.

Concretely, the glass substrate 1 having a 150 nm thick ITO film formed thereon was ultrasonically cleaned in isopropyl alcohol for 20 minutes, and dried for 10 minutes on a hot plate heated at 200° C. Then, the glass substrate with the film was treated with UV ozone for 15 minutes, and mounted within a vacuum deposition machine. Then, the pressure inside the vacuum deposition machine was reduced to 0.001 Pa or lower.

Then, the hole injection layer 3 was formed. Concretely, HIM-1 of the following structural formula was vapor-deposited so as to cover the transparent anode 2, thereby forming the hole injection layer 3 with a film thickness of 5 nm.

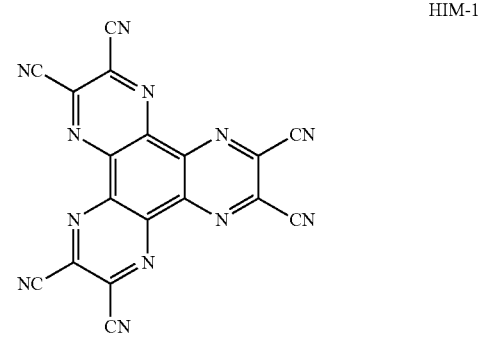 [SMILES: N#Cc1nc2c3nc(C#N)c(C#N)nc3c3nc(C#N)c(C#N)nc3c2nc1C#N]

HIM-1

Then, the first hole transport layer 4 was formed. Concretely, Compound 4-1 represented by the following structural formula was vapor-deposited on the hole injection layer 3 to form the first hole transport layer 4 with a film thickness of 60 nm.

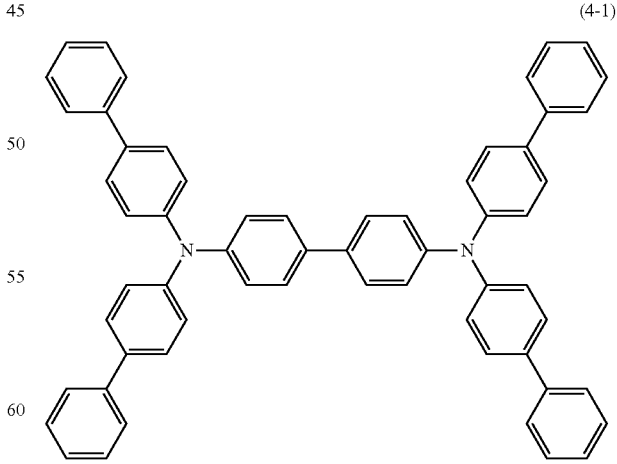

(4-1)

Then, the second hole transport layer 5 was formed. Concretely, Compound 1-92 of Synthesis Example 3 was vapor-deposited on the first hole transport layer 4 to form the second hole transport layer 5 with a film thickness of 5 nm.

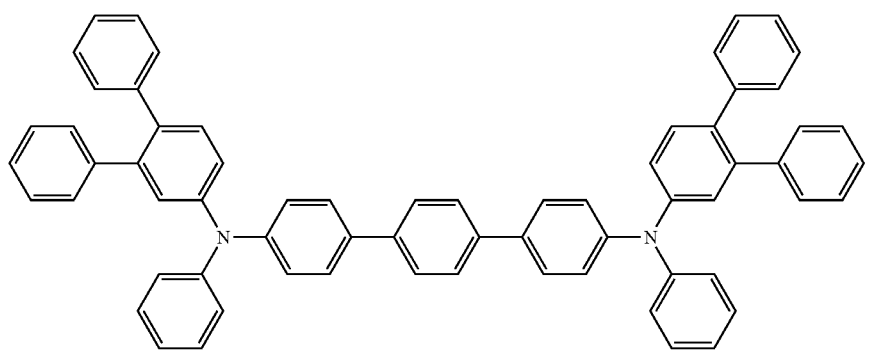

(1-92)

Then, the luminous layer 6 was formed. Concretely, a compound EMD-1 of the following structural formula and a compound EMH-1 of the following structural formula were binary vapor deposited on the second hole transport layer 5 at a vapor deposition rate for providing EMD-1:EMH-1=5:95, whereby the luminous layer 6 with a film thickness of 20 nm was formed.

Then, the electron transport layer 7 was formed.

Concretely, the pyrimidine derivative 2-16 of Synthesis Example 9 and the compound ETM-1 of the following structural formula were binary vapor deposited on the luminous layer 6 at a vapor deposition rate for providing Compound 2-16:ETM-1=50:50, whereby the electron transport layer 7 with a film thickness of 30 nm was formed.

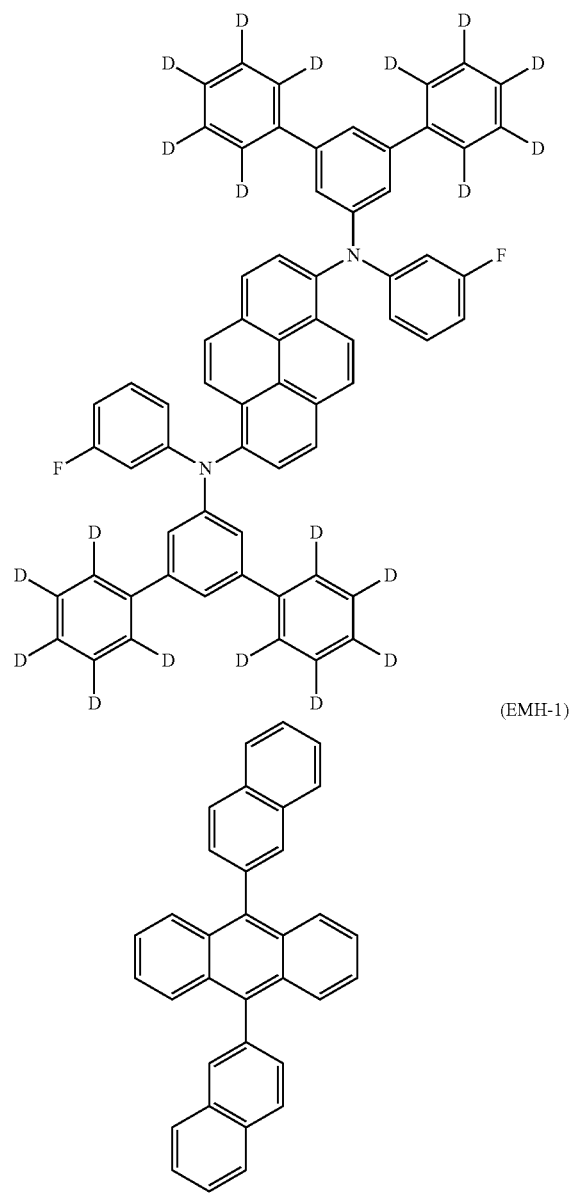

(EMD-1)

(EMH-1)

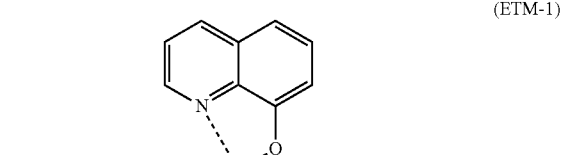

(2-16)

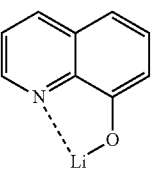

(ETM-1)

Then, the electron injection layer 8 was obtained. Concretely, lithium fluoride was vapor deposited on the electron transport layer 7 to form the electron injection layer 8 with a film thickness of 1 nm.

Finally, aluminum was vapor deposited to a film thickness of 100 nm to form the cathode 9.

<Device Example 2>

An organic EL device was prepared under the same conditions as in Device Example 1, except that Compound 1-130 of Synthesis Example 6 was used, instead of Compound 1-92 of Synthesis Example 3, as the material for the second hole transport layer 5. For the resulting organic EL device, the light emission characteristics at the time of applying a direct current voltage at normal temperature in the atmosphere was measured. The results of the measurement are summarized in Table 1.

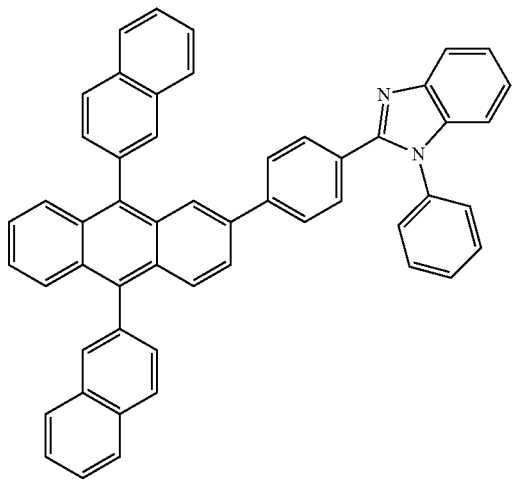

(ETM-2)

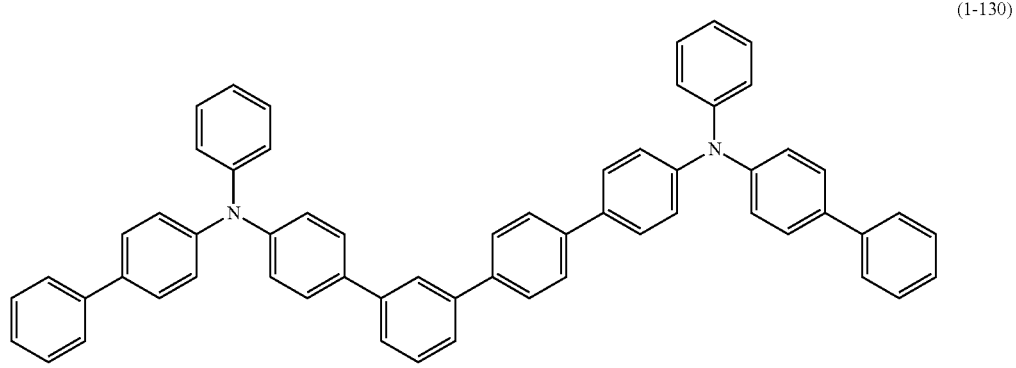 [SMILES: c1ccc(-c2ccc(N(c3ccccc3)c3ccc(-c4ccc(-c5cccc(-c6ccc(N(c7ccccc7)c7ccc(-c8ccccc8)cc7)cc6)c5)cc4)cc3)cc2)cc1]

(1-130)

<Device Comparative Example 1>

An organic EL device was prepared under the same conditions as in Device Example 1, except that the aforementioned Compound 4-1 was used, instead of Compound 1-92 of Synthesis Example 3, as the material for the second hole transport layer 5. In this case, the first hole transport layer 4 and the second hole transport layer 5 functioned as an integral hole transport layer (film thickness 65 nm).

<Device Comparative Example 2>

An organic EL device was prepared under the same conditions as in Device Example 1, except that the aforementioned Compound 4-1 was used as the material for the second hole transport layer 5 instead of Compound 1-92 of Synthesis Example 3, an anthracene derivative ETM-2 (see WO2003/060956) of the following structural formula was used as the material for the electron transport layer 7 instead of the pyrimidine derivative 2-16 of Synthesis Example 9, and that ETM-2 and ETM-1 were binary vapor deposited at a vapor deposition rate for providing ETM-2:ETM-1=50:50.

For each of the organic EL devices prepared in Device Examples 1 to 2 and Device Comparative Examples 1 to 2, the light emission characteristics at the time of applying a direct current voltage at normal temperature in the atmosphere were measured. The results of the measurements are shown in Table 1.

For each of the organic EL devices prepared in Device Examples 1 to 2 and Device Comparative Examples 1 to 2, the device lifetime was measured. Concretely, the device lifetime was measured as the period of time required for the emission luminance to attenuate to 1900 cd/m$^2$ (corresponding to 95% relative to the initial luminance taken as 100%: 95% attenuation) when constant current driving was performed, with the emission luminance at the start of light emission (initial luminance) being set at 2000 cd/m$^2$. The results are shown in Table 1.

TABLE 1

| | First hole transport layer | Second hole transport layer | Electron transport layer | Voltage [V] (@10 mA/cm²) | Luminance [cd/m²] (@10 mA/cm²) | Luminous efficiency [cd/A] (@10 mA/cm²) | Power efficiency [lm/W] (@10 mA/cm²) | Device lifetime (hrs) 95% atten. |
|---|---|---|---|---|---|---|---|---|
| Ex. 1 | Comp. 4-1 | Comp. 1-92 | Comp. 2-16/ ETM-1 | 3.73 | 976 | 9.76 | 8.24 | 150 |
| Ex. 2 | Comp. 4-1 | Comp. 1-130 | Comp. 2-16/ ETM-1 | 3.74 | 985 | 9.85 | 8.26 | 116 |
| Comp. Ex. 1 | Comp. 4-1 | Comp. 4-1 | Comp. 2-16/ ETM-1 | 3.76 | 795 | 7.95 | 6.65 | 83 |
| Comp. Ex. 2 | Comp. 4-1 | Comp. 4-1 | ETM-2/ ETM-1 | 3.84 | 635 | 6.35 | 5.20 | 55 |

Ex. = Device Example
Comp. Ex. = Device Comparative Example
Comp. = Compound
atten. = attenuation The luminous efficiency upon passage of a current at a current density of 10 mA/cm² was 6.35 cd/A in Device Comparative Example 2 using a publicly known electron transport material, while it was 7.95 cd/A, i.e., the efficiency was higher in Device Comparative Example 1 using the pyrimidine derivative II. In Device Examples 1 to 2 using the arylamine compound I as the material for the second hole transport layer, the luminous efficiency was 9.76 to 9.85 cd/A, i.e., the efficiencies were much higher.

The power efficiency was 5.20 lm/W in Device Comparative Example 2 using a publicly known electron transport material, while it was 6.65 lm/W, i.e., the efficiency was higher in Device Comparative Example 1 using the pyrimidine derivative II. In Device Examples 1 to 2 using the arylamine compound I as the material for the second hole transport layer, the power efficiency was 8.24 to 8.26 lm/W, i.e., the efficiencies were much higher.

The device lifetime was 55 hours for the organic EL device of Device Comparative Example 2 using a publicly known electron transport material, while it was 83 hours, i.e., the lifetime was extended in Device Comparative Example 1 using the pyrimidine derivative II. In Device Examples 1 to 2 using the arylamine compound I as the material for the second hole transport layer, the device lifetime was 116 to 150 hours, i.e., the lifetimes were further extended.

The organic EL device of the present invention comprises a combination of the arylamine compound I having a specific structure and the pyrimidine derivative II having a specific structure so that holes and electrons can be efficiently injected into and transported to the luminous layer, thereby making it possible to realize an organic EL device with a high luminous efficiency and a long lifetime. By using the triarylamine compound III or IV having a specific structure as the material for the first hole transport layer, moreover, the material for the first hole transport layer and the material for the second hole transport layer provide a combination capable of injecting and transporting holes into the luminous layer more efficiently, namely, a combination of the materials with a more elaborate carrier balance. Hence, the organic EL device of the present invention has a higher luminous efficiency and a longer lifetime than conventional organic EL devices.

INDUSTRIAL APPLICABILITY

The organic EL device of the present invention, as described above, is increased in luminous efficiency, and greatly improved in durability. Thus, the organic EL device of the present invention can be put to uses such as domestic electrical appliances and illumination.

DESCRIPTION OF REFERENCE NUMERALS

1 Glass substrate
2 Transparent anode
3 Hole injection layer
4 First hole transport layer
5 Second hole transport layer
6 Luminous layer
7 Electron transport layer
8 Electron injection layer
9 Cathode

The invention claimed is:
1. An organic electroluminescent device having at least an anode, a first hole transport layer, a second hole transport layer, a luminous layer, an electron transport layer, and a cathode in this order, wherein
the second hole transport layer contains an arylamine compound represented by the following general formula (1), and
the electron transport layer contains a pyrimidine derivative represented by the following general formula (2):

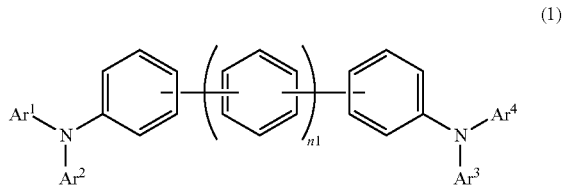

(1)

where
$Ar^1$ to $Ar^4$ may be identical or different, and each represents an aromatic hydrocarbon group, an aromatic heterocyclic group, or a condensed polycyclic aromatic group, and
n1 denotes an integer of 1 to 4;

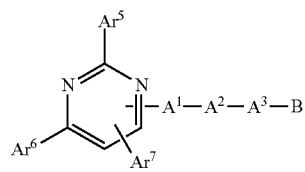

(2)

where
- Ar$^5$ and Ar$^6$ may be identical or different, and each represents an aromatic hydrocarbon group, an aromatic heterocyclic group, or a condensed polycyclic aromatic group, and Ar$^7$ represents a hydrogen atom, an aromatic hydrocarbon group, an aromatic heterocyclic group, or a condensed polycyclic aromatic group,
    wherein the aromatic hydrocarbon group, the aromatic heterocyclic group, or the condensed polycyclic aromatic group represented by Ar$^5$ to Ar$^7$ may be unsubstituted or may have a substituent selected from the group consisting of
    a deuterium atom, a cyano group, a nitro group, a fluorine atom, a chlorine atom, a bromine atom, an iodine atom, a straight-chain or branched alkyl group having 1 to 6 carbon atoms, a straight-chain or branched alkyloxy group having 1 to 6 carbon atoms, a straight-chain or branched alkenyl group, an aryloxy group, an arylalkyloxy group, a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a spirobifluorenyl group, an acenaphthenyl group, a pyridyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a carbolinyl group, an azaspirobifluorenyl group, a diazaspirobifluorenyl group, an arylvinyl group, and an acyl group;
- A$^1$ and A$^2$ may be identical or different, and each represents a divalent group formed by removing two hydrogen atoms from benzene or naphthalene,
- A$^3$ represents a single bond, and
- B represents an aromatic heterocyclic group, which is at least one substituted or unsubstituted group selected from the group consisting of a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzimidazolyl group, a pyrazolyl group, a dibenzofuranyl group, a dibenzothienyl group, an azafluorenyl group, a diazafluorenyl group, a naphthyridinyl group, a phenanthrolinyl group, an acridinyl group, a carbolinyl group, an azaspirobifluorenyl group, a diazaspirobifluorenyl group, a bipyridyl group, a terpyridyl group, a pyrazinyl group, an imidazolyl group, a quinazolinyl group, a benzotriazolyl group, a benzothiadiazolyl group, a pyridopyrrolyl group, a pyridoimidazolyl group, a pyridotriazolyl group, a phenazinyl group, a phenoxazinyl group, and a phenothiazinyl group.

2. The organic electroluminescent device according to claim 1, wherein the first hole transport layer contains a hole transporting arylamine compound.

3. The organic electroluminescent device according to claim 2, wherein the first hole transport layer contains a triarylamine compound having 2 triarylamine structures in a molecule thereof, the triarylamine structures being linked together by a single bond or a heteroatom-free divalent group.

4. The organic electroluminescent device according to claim 3, wherein the triarylamine compound having 2 triarylamine structures in the molecule is represented by the following general formula (4):

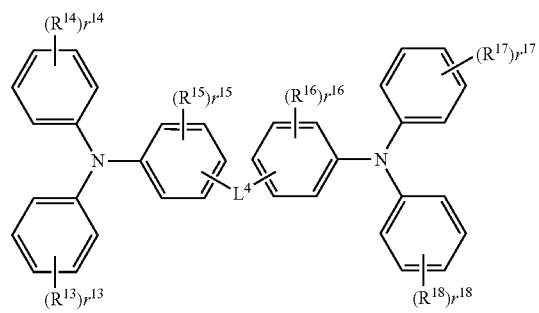

(4)

where
- $r^{13}$, $r^{14}$, $r^{17}$ and $r^{18}$ each denotes an integer of 0 to 5, while $r^{15}$ and $r^{16}$ each denotes an integer of 0 to 4,
- $R^{13}$ to $R^{18}$ may be identical or different, and each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxyl group and, if a plurality of these groups are bound to the same aromatic ring, the plurality of groups bound may be identical or different, and may bind to each other via a single bond, a methylene group, an oxygen atom, or a sulfur atom to form a ring, and
- L$^4$ represents a divalent group represented by any of the following structural formulas (C) to (G), or a single bond;

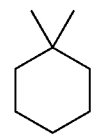

(C)

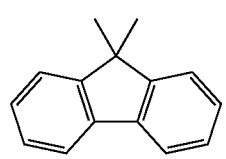

(D)

—CH$_2$— (E)

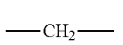  (F)

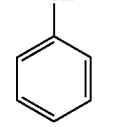  (G)

5. The organic electroluminescent device according to claim 2, wherein the first hole transport layer contains a triarylamine compound having 3 to 6 triarylamine structures in a molecule thereof, the triarylamine structures being linked together by a single bond or a heteroatom-free divalent group.

6. The organic electroluminescent device according to claim 5, wherein the triarylamine compound having 3 to 6 triarylamine structures in the molecule is a triarylamine compound having 4 triarylamine structures in a molecule thereof, the triarylamine compound being represented by the following general formula (3):

each other via a single bond, a methylene group, an oxygen atom, or a sulfur atom to form a ring, and
L$^1$ to L$^3$ may be identical or different, and each represents a divalent group represented by any of the following structural formulas (B) to (G), or a single bond;

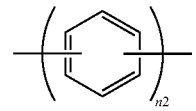  (B)

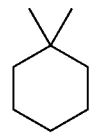  (C)

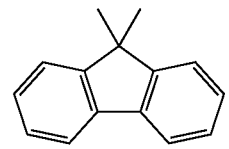  (D)

—CH$_2$—  (E)

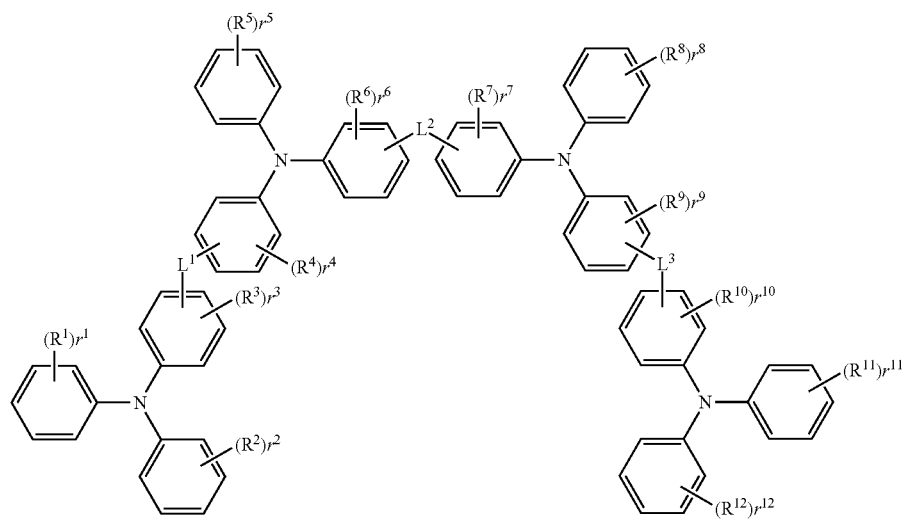 (3)

where
r$^1$, r$^2$, r$^5$, r$^8$, r$^{11}$ and r$^{12}$ each denotes an integer of 0 to 5, r$^3$, r$^4$, r$^6$, r$^7$, r$^9$ and r$^{10}$ each denotes an integer of 0 to 4,
R$^1$ to R$^{12}$ may be identical or different, and each represents a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, an aromatic hydrocarbon group, an aromatic heterocyclic group, a condensed polycyclic aromatic group, or an aryloxyl group and, if a plurality of these groups are bound to the same aromatic ring, the bound groups may be identical or different, and may bind to -continued

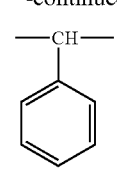  (F)

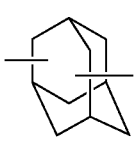  (G)

where n2 denotes an integer of 1 to 3.

7. The organic electroluminescent device according to claim 1, wherein the pyrimidine derivative is represented by the following general formula (2a):

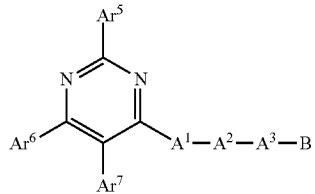

(2a)

where

Ar$^5$ to Ar$^7$, A$^1$ to A$^3$, and B are as defined in the general formula (2).

8. The organic electroluminescent device according to claim 1, wherein the pyrimidine derivative is represented by the following general formula (2b):

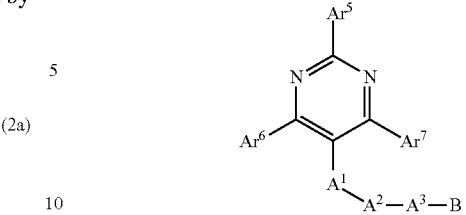

(2b)

where

Ar$^5$ to Ar$^7$, A$^1$ to A$^3$, and B are as defined in the general formula (2).

9. The organic electroluminescent device according to claim 1, wherein the luminous layer contains a blue light emitting dopant.

10. The organic electroluminescent device according to claim 9, wherein the blue light emitting dopant is a pyrene derivative.

11. The organic electroluminescent device according to claim 1, wherein the luminous layer contains an anthracene derivative.

12. The organic electroluminescent device according to claim 11, wherein the luminous layer contains the anthracene derivative as a host material.

* * * * *